US011130992B2

(12) United States Patent
Makrigiorgos

(10) Patent No.: US 11,130,992 B2
(45) Date of Patent: *Sep. 28, 2021

(54) METHODS AND COMPOSITIONS TO ENABLE MULTIPLEX COLD-PCR

(75) Inventor: Gerassimos Makrigiorgos, Chestnut Hill, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 81 days.

This patent is subject to a terminal disclaimer.

(21) Appl. No.: 14/007,173

(22) PCT Filed: Mar. 30, 2012

(86) PCT No.: PCT/US2012/031527
§ 371 (c)(1),
(2), (4) Date: Oct. 28, 2013

(87) PCT Pub. No.: WO2012/135664
PCT Pub. Date: Oct. 4, 2012

(65) Prior Publication Data
US 2014/0051087 A1   Feb. 20, 2014

Related U.S. Application Data

(60) Provisional application No. 61/470,022, filed on Mar. 31, 2011.

(51) Int. Cl.
| C12Q 1/68 | (2018.01) |
| C12Q 1/6853 | (2018.01) |
| C12Q 1/6858 | (2018.01) |
| C12Q 1/686 | (2018.01) |

(52) U.S. Cl.
CPC .......... *C12Q 1/6853* (2013.01); *C12Q 1/686* (2013.01); *C12Q 1/6858* (2013.01)

(58) Field of Classification Search
None
See application file for complete search history.

(56) References Cited

U.S. PATENT DOCUMENTS

| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 5,045,450 A | 9/1991 | Thilly et al. |
| 5,075,217 A | 12/1991 | Weber |
| 5,256,775 A | 10/1993 | Froehler |
| 5,399,491 A | 3/1995 | Kacian et al. |
| 5,409,818 A | 4/1995 | Davey et al. |
| 5,427,930 A | 6/1995 | Birkenmeyer et al. |
| 5,541,308 A | 7/1996 | Hogan et al. |
| 5,554,527 A | 9/1996 | Fickenscher |
| 5,565,340 A | 10/1996 | Chenchik et al. |
| 5,612,473 A | 3/1997 | Wu et al. |
| 5,618,703 A | 4/1997 | Gelfand et al. |
| 5,631,147 A | 5/1997 | Lohman et al. |
| 5,648,211 A | 7/1997 | Fraiser et al. |
| 5,670,316 A | 9/1997 | Calhoun et al. |
| 5,744,311 A | 4/1998 | Fraiser et al. |
| 5,792,607 A | 8/1998 | Backman et al. |
| 5,846,710 A | 12/1998 | Bajaj |
| 5,849,497 A | 12/1998 | Steinman |
| 5,994,056 A | 11/1999 | Higuchi |
| 6,030,115 A | 2/2000 | Ishiguro et al. |
| 6,174,680 B1 | 1/2001 | Makrigiorgos |
| 6,197,499 B1 | 3/2001 | Hughes et al. |
| 7,618,773 B2 | 11/2009 | Rand et al. |
| 7,635,566 B2 | 12/2009 | Brenner |
| 8,071,338 B2 | 12/2011 | Newton |
| 8,455,190 B2 | 6/2013 | Makrigiorgos |

(Continued)

FOREIGN PATENT DOCUMENTS

| CN | 1650028 A | 8/2005 |
| EP | 0 370 719 A2 | 5/1990 |

(Continued)

OTHER PUBLICATIONS

Milbury et al. Ice-COLD-PCR enables rapid amplification and robust enrichment for low abundance unknown DNA mutations. Nucleic Acids Research, vol. 39(1) e2 1-10, Jan. 2011, published online Oct. 2010.*
Mancini et al. The use of cold-PCR and high-resolution melting analysis improves the limit of detection of KRAS and BRAF mutations in colorectal cancer. J Mol Diagn., vol. 12(5), p. 705-711, 2010.*
Partial Supplementary European Search Report for EP12764286.6 dated Nov. 17, 2014.
Extended European Search Report for EP12764286.6 dated Mar. 18, 2015.
Invitation to Pay Additional Fees for PCT/US2012/031527 dated Aug. 28, 2012.
International Search Report and Written Opinion for PCT/US2012/031527 dated Nov. 5, 2012.
International Preliminary Report on Patentability for PCT/US2012/031527 dated Oct. 10, 2013.

(Continued)

*Primary Examiner* — Suryaprabha Chunduru
(74) *Attorney, Agent, or Firm* — Wolf, Greenfield & Sacks, P.C.

(57) ABSTRACT

The present invention is directed to methods, compositions and reaction mixtures for multiplexing COLD-PCR/ice-COLD-PCR to enrich simultaneously several low abundance alleles (mutant target sequences) from a sample. The invention also involves COLD-PCR/ice-COLD-PCR amplification performed on DNA fragments that have different melting temperatures, and therefore different critical denaturation temperatures, in a graded temperature approach such that mutation enrichment is achieved on all diverse DNA fragments simultaneously (temperature-independent COLD-PCR or TI-COLD-PCR). The invention also involves methods for enabling identification of variant-sequence alleles in the presence of a large excess of non-variant alleles in nucleic acids without the complication of polymerase-introduced errors or other primer-introduced artifacts.

13 Claims, 21 Drawing Sheets

Specification includes a Sequence Listing.

(56) References Cited

U.S. PATENT DOCUMENTS

| | | | |
|---|---|---|---|
| 8,623,603 | B2 | 1/2014 | Makrigiorgos |
| 8,628,924 | B2 | 1/2014 | Kacian et al. |
| 9,133,490 | B2 | 9/2015 | Candau-Cachon |
| 9,957,556 | B2 | 5/2018 | Makrigiorgos |
| 2002/0016680 | A1 | 2/2002 | Wang et al. |
| 2002/0045227 | A1* | 4/2002 | Wagener ............. C12Q 1/6827 435/173.9 |
| 2003/0008286 | A1 | 1/2003 | Zou et al. |
| 2003/0092021 | A1* | 5/2003 | Thilly ................. C12Q 1/6827 435/6.11 |
| 2004/0023207 | A1 | 2/2004 | Polansky |
| 2004/0033518 | A1 | 2/2004 | Wittwer et al. |
| 2004/0166519 | A1 | 8/2004 | Cargill et al. |
| 2005/0089984 | A1 | 4/2005 | Ginns et al. |
| 2006/0057569 | A1 | 3/2006 | Charle |
| 2006/0063175 | A1 | 3/2006 | Xu et al. |
| 2007/0020672 | A1 | 1/2007 | Wittwer et al. |
| 2007/0154892 | A1 | 7/2007 | Wain-Hobson et al. |
| 2008/0269068 | A1* | 10/2008 | Church ................ C12Q 1/6874 506/9 |
| 2009/0053698 | A1 | 2/2009 | Hayashida |
| 2010/0173311 | A1 | 7/2010 | Grow et al. |
| 2010/0203532 | A1 | 8/2010 | Makrigiorgos |
| 2010/0233683 | A1 | 9/2010 | Molloy et al. |
| 2011/0217714 | A1 | 9/2011 | Makrigiorgos |
| 2012/0225421 | A1 | 9/2012 | Richardson et al. |
| 2013/0309724 | A1 | 11/2013 | Candau-Cachon |
| 2014/0106362 | A1 | 4/2014 | Makrigiorgos |
| 2014/0315726 | A1 | 10/2014 | Beatty et al. |
| 2015/0147760 | A1 | 5/2015 | Gupta et al. |
| 2016/0186237 | A1 | 6/2016 | Makrigiorgos et al. |
| 2018/0282798 | A1 | 10/2018 | Makrigiorgos |

FOREIGN PATENT DOCUMENTS

| | | |
|---|---|---|
| EP | 2 004 852 B1 | 12/2010 |
| GB | 2 293 238 A | 3/1996 |
| JP | 6-510201 | 11/1994 |
| JP | 2005-536983 | 12/2005 |
| JP | 2012-165755 | 9/2012 |
| WO | WO 90/11369 A1 | 10/1990 |
| WO | WO 90/13668 A1 | 11/1990 |
| WO | WO 91/14003 A2 | 9/1991 |
| WO | WO 97/19193 A2 | 5/1997 |
| WO | WO 99/14226 A2 | 3/1999 |
| WO | WO 99/61661 A1 | 12/1999 |
| WO | WO 01/068900 A2 | 9/2001 |
| WO | WO 02/018659 A2 | 3/2002 |
| WO | WO 02/086155 A2 | 10/2002 |
| WO | WO 03/072809 A1 | 9/2003 |
| WO | WO 2005/093101 A1 | 10/2005 |
| WO | WO 2007/047572 A2 | 4/2007 |
| WO | WO 2007/087310 A2 | 8/2007 |
| WO | WO 2007/106534 A2 | 9/2007 |
| WO | WO 2009/017784 A2 | 2/2009 |
| WO | WO 2009/019008 A1 | 2/2009 |
| WO | WO 2009017784 A2 * 2/2009 ........... C12Q 1/6848 |
| WO | WO 2010/065626 A1 | 6/2010 |
| WO | WO 2011/112534 A1 | 9/2011 |
| WO | WO 2012/129363 A2 | 9/2012 |
| WO | WO 2012/135664 A2 | 10/2012 |
| WO | WO 2012/159089 A1 | 11/2012 |
| WO | WO 2014/142261 A1 | 9/2014 |

OTHER PUBLICATIONS

International Search Report and Written Opinion for PCT/US2014/047373 dated Nov. 12, 2014.
International Preliminary Report on Patentability for PCT/EP2008/006476 dated Feb. 9, 2010.
International Search Report and Written Opinion for PCT/US2008/009248 dated Jan. 6, 2009.
International Preliminary Report on Patentability for PCT/US2008/009248 dated Feb. 2, 2010.
International Search Report and Written Opinion for PCT/US2011/027473 dated Jun. 28, 2011.
International Preliminary Report on Patentability for PCT/US2011/027473 dated Sep. 20, 2012.
[No Author Listed] BioMath Calculators: Tm Calculation for Oligos. Last accessed Oct. 27, 2014 from https://www.promega.com/techserv/tools/biomath/calc11.htm.
[No Author Listed] COLD-PCR: Very High Sensitivity Mutation Detection. Transgenomic. Jul. 1, 2010: 31 pages. Last accessed at <http://www.transgenomic.com/files/literature/48227300.pdf> on Oct. 25, 2014.
[No Author Listed] User Guide for the REVEAL Kit KRAS Exon 2. A Mutation Enrichment Assay Powered by ICE COLD-PCR. Transgenomic, Inc 2012.
Ahrendt et al., p53 mutations and survival in stage I non-small-cell lung cancer: results of a prospective study. J Natl Cancer Inst. Jul. 2, 2003;95(13):961-70.
Altschul et al., Gapped BLAST and PSI-BLAST: a new generation of protein database search programs. Nucleic Acids Res. Sep. 1, 1997;25(17):3389-402.
Amicarelli et al., FLAG assay as a novel method for real-time signal generation during PCR: application to detection and genotyping of KRAS codon 12 mutations. Nucleic Acids Res. 2007;35(19):e131. Epub Oct. 11, 2007.
Aoki et al., Liposome-mediated in vivo gene transfer of antisense K-ras construct inhibits pancreatic tumor dissemination in the murine peritoneal cavity. Cancer Res. Sep. 1, 1995;55(17):3810-6.
Belinsky et al., Gene promoter methylation in plasma and sputum increases with lung cancer risk. Clin Cancer Res. Sep. 15, 2005;11(18):6505-11.
Bi et al., Detection of known mutation by proof-reading PCR. Nucleic Acids Res. Jun. 15, 1998;26(12):3073-5.
Blake et al., Thermal stability of DNA. Nucleic Acids Res. Jul. 15, 1998;26(14):3323-32.
Boisselier et al., COLD PCR HRM: a highly sensitive detection method for IDH1 mutations. Hum Mutat. Dec. 2010;31(12):1360-5. doi: 10.1002/humu.21365. Epub Nov. 9, 2010.
Botstein et al., Construction of a genetic linkage map in man using restriction fragment length polymorphisms. Am J Hum Genet. May 1980;32(3):314-31.
Candau et al., Very High Sensitivity Detection of K-RAS Exon 2 Mutations Using Fast COLD-PCR. AACR 2010 Poster Presentation.
Castellanos-Rizaldos et al., Temperature-tolerant COLD-PCR reduces temperature stringency and enables robust mutation enrichment. Clin Chem. Jul. 2012;58(7):1130-8. doi: 10.1373/clinchem.2012.183095. Epub May 15, 2012.
Chakrabarti et al., Highly selective isolation of unknown mutations in diverse DNA fragments: toward new multiplex screening in cancer. Cancer Res. Jul. 15, 2000;60(14):3732-7.
Chen et al., Fetal DNA analyzed in plasma from a mother's three consecutive pregnancies to detect paternally inherited aneuploidy. Clin Chem. May 2001;47(5):937-9.
Chiu et al., Hypermethylation of RASSF1A in human and rhesus placentas. Am J Pathol. Mar. 2007;170(3):941-50.
Chou et al., A comparison of high-resolution melting analysis with denaturing high-performance liquid chromatography for mutation scanning: cystic fibrosis transmembrane conductance regulator gene as a model. Am J Clin Pathol. Sep. 2005;124(3):330-8.
Chow et al., Mass spectrometric detection of an SNP panel as an internal positive control for fetal DNA analysis in maternal plasma. Clin Chem. Jan. 2007;53(1):141-2.
Däbritz et al., Detection of Ki-ras mutations in tissue and plasma samples of patients with pancreatic cancer using PNA-mediated PCR clamping and hybridisation probes. Br J Cancer. Jan. 31, 2005;92(2):405-12.
Delaney et al., GNAS1 mutations occur more commonly than previously thought in intramuscular myxoma. Mod Pathol. May 2009;22(5):718-24. doi: 10.1038/modpathol.2009.32. Epub Mar. 13, 2009.

(56) References Cited

OTHER PUBLICATIONS

Di Fiore et al., Clinical relevance of KRAS mutation detection in metastatic colorectal cancer treated by Cetuximab plus chemotherapy. Br J Cancer. Apr. 23, 2007;96(8):1166-9. Epub Mar. 20, 2007.
Diehl et al., BEAMing: single-molecule PCR on microparticles in water-in-oil emulsions. Nat Methods. Jul. 2006;3(7):551-9.
Diehl et al., Circulating mutant DNA to assess tumor dynamics. Nat Med. Sep. 2008;14(9):985-90. doi:10.1038/nm.1789. Epub Jul. 31, 2007.
Diehl et al., Detection and quantification of mutations in the plasma of patients with colorectal tumors. Proc Natl Acad Sci U S A. Nov. 8, 2005;102(45):16368-73. Epub Oct. 28, 2005.
Dominguez et al., Wild-type blocking polymerase chain reaction for detection of single nucleotide minority mutations from clinical specimens. Oncogene. Oct. 13, 2005;24(45):6830-4. Erratum in: Oncogene. Jan. 26, 2006;25(4):656.
Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Eberhard et al., Mutations in the epidermal growth factor receptor and in KRAS are predictive and prognostic indicators in patients with non-small-cell lung cancer treated with chemotherapy alone and in combination with erlotinib. J Clin Oncol. Sep. 1, 2005;23(25):5900-9. Epub Jul. 25, 2005.
Engelman et al., Allelic dilution obscures detection of a biologically significant resistance mutation in EGIR-amplified lung cancer. J Clin Invest. Oct. 2006;116(10):2695-706. Epub Aug. 10, 2006.
Fan et al., A versatile assay for high-throughput gene expression profiling on universal array matrices. Genome Res. May 2004;14(5):878-85.
Frommer et al., A genomic sequencing protocol that yields a positive display of 5-methylcytosine residues in individual DNA strands. Proc Natl Acad Sci U S A. Mar. 1, 1992;89(5):1827-31.
Fuery et al., Detection of rare mutant alleles by restriction endonuclease-mediated selective-PCR: assay design and optimization. Clin Chem. May 2000;46(5):620-4.
Galbiati et al., Novel use of Full COLD-PCR protocol for noninvasive prenatal diagnosis of genetic diseases. Clin Chem. Jan. 2011;57(1):136-8. doi: 10.1373/clinchem.2010.155671. Epub Oct. 25, 2010.
Giesendorf et al., Molecular beacons: a new approach for semiautomated mutation analysis. Clin Chem. Mar. 1998;44(3):482-6.
Gonzalez et al., Microsatellite alterations and TP53 mutations in plasma DNA of small-cell lung cancer patients: follow-up study and prognostic significance. Ann Oncol. Sep. 2000;11(9):1097-104.
Gray, Cancer: Genomics of metastasis. Nature. Apr. 15, 2010;464(7291):989-90. doi:10.1038/464989a.
Guatelli et al., Isothermal, in vitro amplification of nucleic acids by a multienzyme reaction modeled after retroviral replication. Proc Natl Acad Sci U S A. Mar. 1990;87(5):1874-8. Erratum in: Proc Natl Acad Sci U S A Oct. 1990;87(19):7797.
Gundry et al., Amplicon melting analysis with labeled primers: a closed-tube method for differentiating homozygotes and heterozygotes. Clin Chem. Mar. 2003;49(3):396-406.
Gyllensten et al., Generation of single-stranded DNA by the polymerase chain reaction and its application to direct sequencing of the HLA-DQA locus. Proc Natl Acad Sci U S A. Oct. 1988;85(20):7652-6.
Henikoff et al., Amino acid substitution matrices from protein blocks. Proc Natl Acad Sci U S A. Nov. 15, 1992;89(22):10915-9.
Hibi et al., Molecular detection of genetic alterations in the serum of colorectal cancer patients. Cancer Res. Apr. 1, 1998;58(7):1405-7.
Huang et al., Mutations in exon 7 and 8 of p53 as poor prognostic factors in patients with nonsmall cell lung cancer. Oncogene. May 14, 1998;16(19):2469-77.

Jackson et al., Specific p53 mutations detected in plasma and tumors of hepatocellular carcinoma patients by electrospray ionization mass spectrometry. Cancer Res. Jan. 1, 2001;61(1):33-5.
Jänne et al., A rapid and sensitive enzymatic method for epidermal growth factor receptor mutation screening. Clin Cancer Res. Feb. 1, 2006;12(3 Pt 1):751-8.
Jeffreys et al., DNA enrichment by allele-specific hybridization (DEASH): a novel method for haplotyping and for detecting low-frequency base substitutional variants and recombinant DNA molecules. Genome Res. Oct. 2003;13(10):2316-24.
Kanehisa, Use of statistical criteria for screening potential homologies in nucleic acid sequences. Nucleic Acids Res. Jan. 11, 1984;12(1 Pt 1):203-13.
Karlin et al., Applications and statistics for multiple high-scoring segments in molecular sequences. Proc Natl Acad Sci U S A. Jun. 15, 1993;90(12):5873-7.
Khrapko et al., Constant denaturant capillary electrophoresis (CDCE): a high resolution approach to mutational analysis. Nucleic Acids Res. Feb. 11, 1994;22(3):364-9.
Kimura et al., Mutant DNA in plasma of lung cancer patients: potential for monitoring response to therapy. Ann N Y Acad Sci. Jun. 2004;1022:55-60.
Kopreski et al., Somatic mutation screening: identification of individuals harboring K-ras mutations with the use of plasma DNA. J Natl Cancer Inst. Jun. 7, 2000;92(11):918-23.
Kosaka et al., Mutations of the epidermal growth factor receptor gene in lung cancer: biological and clinical implications. Cancer Res. Dec. 15, 2004;64(24):8919-23.
Kuliński et al., Comparative calorimetric studies on the dynamic conformation of plant 5S rRNA: II. Structural interpretation of the thermal unfolding patterns for lupin seeds and wheat germ. Nucleic Acids Res. May 11, 1991;19(9):2449-55.
Kwoh et al., Transcription-based amplification system and detection of amplified human immunodeficiency virus type 1 with a bead-based sandwich hybridization format. Proc Natl Acad Sci U S A. Feb. 1989;86(4):1173-7.
Kwok, Finding a needle in a haystack: detection and quantification of rare mutant alleles are coming of age. Clin Chem. May 2000;46(5):593-4.
Lander et al., Mapping mendelian factors underlying quantitative traits using RFLP linkage maps. Genetics. Jan. 1989;121(1):185-99. Erratum in: Genetics Feb. 1994;136(2):705.
Li et al., BEAMing up for detection and quantification of rare sequence variants. Nat Methods. Feb. 2006;3(2):95-7.
Li et al., Coamplification at lower denaturation temperature-PCR increases mutation-detection selectivity of TaqMan-based real-time PCR. Clin Chem. Apr. 2009;55(4):748-56. doi:10.1373/clinchem.2008.113381. Epub Feb. 20, 2009.
Li et al., COLD-PCR: a new platform for highly improved mutation detection in cancer and genetic testing. Biochem Soc Trans. Apr. 2009;37(Pt 2):427-32. doi: 10.1042/BST0370427.
Li et al., Multiplex padlock targeted sequencing reveals human hypermutable CpG variations. Genome Res. Sep. 2009;19(9):1606-15. doi: 10.1101/gr.092213.109. Epub Jun. 12, 2009.
Li et al., Replacing PCR with COLD-PCR enriches variant DNA sequences and redefines the sensitivity of genetic testing. Nat Med. May 2008;14(5):579-84. doi: 10.1038/nml708. Epub Apr. 13, 2008.
Li et al., s-RT-MELT for rapid mutation scanning using enzymatic selection and real time DNA-melting: new potential for multiplex genetic analysis. Nucleic Acids Res. 2007;35(12):e84. Epub Jun. 1, 2007.
Li et al., Two-round coamplification at lower denaturation temperature-PCR (COLD-PCR)-based sanger sequencing identifies a novel spectrum of low-level mutations in lung adenocarcinoma. Hum Mutat. Nov. 2009;30(11):1583-90. doi: 10.1002/humu.21112.
Liew et al., Genotyping of single-nucleotide polymorphisms by high-resolution melting of small amplicons. Clin Chem. Jul. 2004;50(7):1156-64.
Lipsky et al., DNA melting analysis for detection of single nucleotide polymorphisms. Clin Chem. Apr. 2001;47(4):635-44.
Li-Sucholeiki et al., A sensitive scanning technology for low frequency nuclear point mutations in human genomic DNA. Nucleic Acids Res. May 1, 2000;28(9):E44.

(56) References Cited

OTHER PUBLICATIONS

Liu et al., Denaturing high performance liquid chromatography (DHPLC) used in the detection of germline and somatic mutations. Nucleic Acids Res. Mar. 15, 1998;26(6):1396-400.

Liu et al., Inverse PCR-based RFLP scanning identifies low-level mutation signatures in colon cells and tumors. Cancer Res. Apr. 1, 2004;64(7):2544-51.

Luo et al., Detection of rare mutant K-ras DNA in a single-tube reaction using peptide nucleic acid as both PCR clamp and sensor probe. Nucleic Acids Res. Jan. 23, 2006;34(2):e12.

Luthra et al., COLD-PCR finds hot application in mutation analysis. Clin Chem. Dec. 2009;55(12):2077-8. doi: 10.1373/clinchem.2009.136143. Epub Oct. 15, 2009.

Mamon et al., Preferential amplification of apoptotic DNA from plasma: potential for enhancing detection of minor DNA alterations in circulating DNA. Clin Chem. Sep. 2008;54(9):1582-4. doi: 10.1373/clinchem.2008.104612.

Mancini et al., The use of COLD-PCR and high-resolution melting analysis improves the limit of detection of KRAS and BRAF mutations in colorectal cancer. J Mol Diagn. Sep. 2010;12(5):705-11. doi: 10.2353/jmoldx.2010.100018. Epub Jul. 8, 2010.

Maulik et al., Novel non-isotopic detection of MutY enzyme-recognized mismatches in DNA via ultrasensitive detection of aldehydes. Nucleic Acids Res. Mar. 1, 1999;27(5):1316-22.

Mayall et al., Mutations of p53 gene can be detected in the plasma of patients with large bowel carcinoma. J Clin Pathol.Aug. 1998;51(8):611-3.

Milbury et al., COLD-PCR-enhanced high-resolution melting enables rapid and selective identification of low-level unknown mutations. Clin Chem. Dec. 2009;55(12):2130-43. doi: 10.1373/clinchem.2009.131029. Epub Oct. 8, 2009.

Milbury et al., Ice-COLD-PCR enables rapid amplification and robust enrichment for low-abundance unknown DNA mutations. Nucleic Acids Res. Jan. 2011;39(1):e2. doi: 10.1093/nar/gkq899. Epub Oct. 11, 2010.

Milbury et al., Multiplex amplification coupled with COLD-PCR and high resolution melting enables identification of low-abundance mutations in cancer samples with low DNA content. J Mol Diagn. Mar. 2011;13(2):220-32. doi: 10.1016/j.jmoldx.2010.10.008.

Milbury et al., PCR-based methods for the enrichment of minority alleles and mutations. Clin Chem. Apr. 2009;55(4):632-40. doi: 10.1373/clinchem.2008.113035. Epub Feb. 6, 2009.

Mitra et al., Digital genotyping and haplotyping with polymerase colonies. Proc Natl Acad Sci U S A. May 13, 2003;100(10):5926-31. Epub May 2, 2003.

Mitra et al., Fluorescent in situ sequencing on polymerase colonies. Anal Biochem. Sep. 1, 2003;320(1):55-65. Erratum in: Anal Biochem. May 15, 2004;328(2):245.

Mitsudomi et al., Prognostic significance of p53 alterations in patients with non-small cell lung cancer: a meta-analysis. Clin Cancer Res. Oct. 2000;6(10):4055-63.

Murakami et al., p53 gene mutations are associated with shortened survival in patients with advanced non-small cell lung cancer: an analysis of medically managed patients. Clin Cancer Res. Feb. 2000;6(2):526-30.

Nagai et al., Development of a microchamber array for picoliter PCR. Anal Chem. Mar. 1, 2001;73(5):1043-7.

Nagai et al., High-throughput PCR in silicon based microchamber array. Biosens Bioelectron. Dec. 2001;16(9-12):1015-9.

Nollau et al., Methods for detection of point mutations: performance and quality assessment. IFCC Scientific Division, Committee on Molecular Biology Techniques. Clin Chem. Jul. 1997;43(7):1114-28.

Obika et al., Stability and structural features of the duplexes containing nucleoside analogues with a fixed N-type conformation, 2'-O,4'-C-methyleneribonucleosides. Tetrahedron Lett. 1998;39:5401-4.

Ogino et al., Sensitive sequencing method for KRAS mutation detection by Pyrosequencing. J Mol Diagn. Aug. 2005;7(3):413-21.

Oldenburg et al., Selective amplification of rare mutations using locked nucleic acid oligonucleotides that competitively inhibit primer binding to wild-type DNA. J Invest Dermatol. Feb. 2008;128(2):398-402. Epub Jun. 21, 2007.

Orum et al., Single base pair mutation analysis by PNA directed PCR clamping. Nucleic Acids Res. Nov. 25, 1993;21(23):5332-6.

Paez et al., EGFR mutations in lung cancer: correlation with clinical response to gefitinib therapy. Science. Jun. 4, 2004;304(5676):1497-500. Epub Apr. 29, 2004.

Pearson et al., Improved tools for biological sequence comparison. Proc Natl Acad Sci U S A. Apr. 1988;85(8):2444-8.

Petrie et al., Deep sequencing analysis of mutations resulting from the incorporation of dNTP analogs. Nucleic Acids Res. Dec. 2010;38(22):8095-104. doi:10.1093/nar/gkq685. Epub Aug. 6, 2010.

Pinzani et al., BRAFV600E detection in melanoma is highly improved by COLD-PCR. Clin Chim Acta. May 12, 2011;412(11-12):901-5. doi: 10.1016/j.cca.2011.01.014. Epub Jan. 22, 2011.

Porreca et al., Polony DNA sequencing. Curr Protoc Mol Biol. Nov. 2006;Chapter 7:Unit 7.8. doi: 10.1002/0471142727.mb0708s76.

Qin et al., Ultra deep sequencing detects a low rate of mosaic mutations in tuberous sclerosis complex. Hum Genet. Mar. 2010;127(5):573-82. doi: 10.1007/s00439-010-0801-z. Epub Feb. 18, 2010.

Raja et al., Temperature-controlled primer limit for multiplexing of rapid, quantitative reverse transcription-PCR assays: application to intraoperative cancer diagnostics. Clin Chem. Aug. 2002;48(8):1329-37.

Reed et al., Sensitivity and specificity of single-nucleotide polymorphism scanning by high-resolution melting analysis. Clin Chem. Oct. 2004;50(10):1748-54. Epub Aug. 12, 2004.

Sanchez et al., Two-temperature LATE-PCR endpoint genotyping. BMC Biotechnol. Dec. 4, 2006;6:44.

Saunders et al., Interlaboratory study on thermal cycler performance in controlled PCR and random amplified polymorphic DNA analyses. Clin Chem. Jan. 2001;47(1):47-55.

Seyama et al., A novel blocker-PCR method for detection of rare mutant alleles in the presence of an excess amount of normal DNA. Nucleic Acids Res. May 25, 1992;20(10):2493-6.

Shah et al., Mutational evolution in a lobular breast tumour profiled at single nucleotide resolution. Nature. Oct. 8, 2009;461(7265):809-13. doi: 10.1038/nature08489.

Shao et al., p53 mutation in plasma DNA and its prognostic value in breast cancer patients. Clin Cancer Res. Aug. 2001;7(8):2222-7. Retraction in: Shao ZM, Wu J, Shen ZZ, Nguyen M. Clin Cancer Res. Sep. 2002;8(9):3027.

Shi et al., Ultra-sensitive detection of BRAF V600E and G469A mutations by ICE COLD-PCR and BLOCKer sequencing. Sep. 2011 Poster.

Shi et al., Use of BLOCker Sequencing (BLocking Oligonucleotide Cycle Sequencing) after Ice COLD-PCR for detection of K-RAS and BRAF mutations. May 2011 Poster.

Shigematsu et al., Clinical and biological features associated with epidermal growth factor receptor gene mutations in lung cancers. J Natl Cancer Inst. Mar. 2, 2005;97(5):339-46.

Silva et al., Tumor DNA in plasma at diagnosis of breast cancer patients is a valuable predictor of disease-free survival. Clin Cancer Res. Dec. 2002;8(12):3761-6.

Steger, Thermal denaturation of double-stranded nucleic acids: prediction of temperatures critical for gradient gel electrophoresis and polymerase chain reaction. Nucleic Acids Res. Jul. 25, 1994;22(14):2760-8.

Sun et al., Detection of tumor mutations in the presence of excess amounts of normal DNA. Nat Biotechnol. Feb. 2002;20(2):186-9.

Suspène et al., Inversing the natural hydrogen bonding rule to selectively amplify GC-rich ADAR-edited RNAs. Nucleic Acids Res. Jul. 2008;36(12):e72. doi: 10.1093/nar/gkn295. Epub May 30, 2008.

Tang et al., Characterization of mitochondrial DNA heteroplasmy using a parallel sequencing system. Biotechniques. Apr. 2010;48(4):287-96. doi:10.2144/000113389.

Thomas et al., High-throughput oncogene mutation profiling in human cancer. Nat Genet. Mar. 2007;39(3):347-51. Epub Feb. 11,

(56) References Cited

OTHER PUBLICATIONS

2007. Erratum in: Nat Genet. Apr. 2007;39(4):567. Macconnaill, Laura E [corrected to MacConaill, Laura].
Thomas et al., Sensitive mutation detection in heterogeneous cancer specimens by massively parallel picoliter reactor sequencing. Nat Med. Jul. 2006;12(7):852-5. Epub Jun. 25, 2006. Erratum in: Nat Med. Oct. 2006;12(10):1220.
Till et al., High-throughput discovery of rare human nucleotide polymorphisms by Ecotilling. Nucleic Acids Res. Aug. 7, 2006;34(13):e99. Erratum in: Nucleic Acids Res. 2006;34(18):5352.
Vestheim et al., Blocking primers to enhance PCR amplification of rare sequences in mixed samples—a case study on prey DNA in Antarctic krill stomachs. Front Zool. Jul. 20, 2008;5:12. doi: 10.1186/1742-9994-5-12.
Wagner et al., Challenges for biomarkers in cancer detection. Ann N Y Acad Sci. Jun. 2004;1022:9-16.
Walker et al., Strand displacement amplification—an isothermal, in vitro DNA amplification technique. Nucleic Acids Res. Apr. 11, 1992;20(7):1691-6.
Wetmur, DNA probes: applications of the principles of nucleic acid hybridization. Crit Rev Biochem Mol Biol. 1991;26(3-4):227-59.
Wittwer et al., High-resolution genotyping by amplicon melting analysis using LCGreen. Clin Chem. Jun. 2003;49(6 Pt 1):853-60.
Worm et al., In-tube DNA methylation profiling by fluorescence melting curve analysis. Clin Chem. 2001;47(7):1183-9.
Xu et al., Dual primer emulsion PCR for next-generation DNA sequencing. Biotechniques. May 2010;48(5):409-12. doi: 10.2144/000113423.
Yeung et al., Enzymatic mutation detection technologies. Biotechniques. May 2005;38(5):749-58.
Zhou et al., Closed-tube genotyping with unlabeled oligonucleotide probes and a saturating DNA dye. Clin Chem. Aug. 2004;50(8):1328-35. Epub May 27, 2004.
Zuo et al., Application of COLD-PCR for improved detection of KRAS mutations in clinical samples. Mod Pathol. Aug. 2009;22(8):1023-31. doi:10.1038/modpathol.2009.59. Epub May 8, 2009.
Ahmadian et al., Pyrosequencing: history, biochemistry and future. Clin Chim Acta. Jan. 2006;363(1-2):83-94. Epub Sep. 13, 2005.
Armour et al., Recent advances in minisatellite biology. FEBS Lett. Jul. 27, 1992;307(1):113-5.
Beaucage et al., Deoxynucleoside phosphoramidites—A new class of key intermediates for deoxypolynucleotide synthesis. Tetrahedron Letters. 1981;22(20):1859-62. doi: 10.1016/S00404039(01)90461-7.
Braasch et al., Locked nucleic acid (LNA): fine-tuning the recognition of DNA and RNA. Chem Biol. Jan. 2001;8(1):1-7.
Compton, Nucleic acid sequence-based amplification. Nature. Mar. 7, 1991;350(6313):91-2.
Coutelle, New DNA-analysis techniques (minireview). Biomed Biochim Acta. 1991;50(1):3-10.
Dif-Couvreux et al., [Evaluation of conventional hemi nested PCR analysis for fetal RHD determination in maternal plasma]. J Gynecol Obstet Biol Reprod (Paris). Nov. 2006;35(7):658-64. French.
Greenman et al., Patterns of somatic mutation in human cancer genomes. Nature. Mar. 8, 2007;446(7132):153-8.
Grossi et al., Prognostic significance of K-ras, p53, bcl-2, PCNA, CD34 in radically resected non-small cell lung cancers. Eur J Cancer. Jun. 2003;39(9):1242-50.
Huang et al., Mutations of p53 and K-ras genes as prognostic factors for non-small cell lung cancer. Int J Oncol. Mar. 1998;12(3):553-63.
Koshkin et al., LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron. 1998;54(14):3607-30. doi: 10.1016/s00404020(98)00094-5.
Kwok, High-throughput genotyping assay approaches. Pharmacogenomics. Feb. 2000;1(1):95-100.
Latorra et al., Enhanced allele-specific PCR discrimination in SNP genotyping using 3' locked nucleic acid (LNA) primers. Hum Mutat. Jul. 2003;22(1):79-85.
Lázaro et al., Mutation analysis of genetic diseases by asymmetric-PCR SSCP and ethidium bromide staining: application to neurofibromatosis and cystic fibrosis. Mol Cell Probes. Oct. 1992;6(5):357-9.
Liu et al., Detection of hotspot mutations and polymorphisms using an enhanced PCR-RFLP approach. Hum Mutat. May 2003;21(5):535-41.
Makrigiorgos, PCR-based detection of minority point mutations. Hum Mutat. May 2004;23(5):406-12.
Mao et al., Synthesis of radioactive single-stranded DNA probes using asymmetrical PCR and oligonucleotide random priming. Biotechniques. Oct. 1999;27(4):674-6, 678.
Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120. Ho, Chun He [corrected to Ho, Chun Heen].
Montgomery et al., Simultaneous mutation scanning and genotyping by high-resolution DNA melting analysis. Nat Protoc. 2007;2(1):59-66.
Nickerson et al., Random mutagenesis-PCR to introduce alterations into defined DNA sequences for validation of SNP and mutation detection methods. Hum Mutat. Mar. 2001;17(3):210-9.
Orita et al., Rapid and sensitive detection of point mutations and DNA polymorphisms using the polymerase chain reaction. Genomics. Nov. 1989;5(4):874-9.
Paner et al., Analysis of melting transitions of the DNA hairpins formed from the oligomer sequences d[GGATAC(X)4GTATCC] (X=A, T, G, C). Biopolymers. Dec. 1990;29(14):1715-34.
Persson et al., Four-color multiplex reverse transcription polymerase chain reaction—overcoming its limitations. Anal Biochem. Sep. 1, 2005;344(1):33-42.
Pomp et al., Organic solvents as facilitators of polymerase chain reaction. Biotechniques. Jan. 1991;10(1):58-9.
Rehbein et al., Comparison of different methods to produce single-strand DNA for identification of canned tuna by single-strand conformation polymorphism analysis. Electrophoresis. Jun. 1998;19(8-9):1381-4.
Saiki et al., Enzymatic amplification of beta-globin genomic sequences and restriction site analysis for diagnosis of sickle cell anemia. Science. Dec. 20, 1985;230(4732): 1350-4.
Smith et al., Comparison of biosequences. Adv Appl Math. Dec. 1981;2(4):482-9. doi: 10.1016/01968858(81)90046-4.
Tong et al., Diagnostic developments involving cell-free (circulating) nucleic acids. Clin Chim Acta. Jan. 2006;363(1-2):187-96. Epub Aug. 26, 2005.
Tsang et al., Circulating nucleic acids in plasma/serum. Pathology. Apr. 2007;39(2):197-207.
Vámosi et al., The helix-coil transition of DNA duplexes and hairpins observed by multiple fluorescence parameters. Biochemistry. Oct. 6, 1998;37(40):14300-16.
Völker et al., High-resolution calorimetric and optical melting profiles of DNA plasmids: resolving contributions from intrinsic melting domains and specifically designed inserts. Biopolymers. Sep. 1999;50(3):303-18. Erratum in: Biopolymers Jan. 2000;53(1):112.
Wang et al., Determination of human beta(2)-adrenoceptor haplotypes by denaturation selective amplification and subtractive genotyping. Am J Pharmacogenomics. 2001;1(4):315-22.
Wittwer et al., The LightCycler: a microvolume multisample fluorimeter with rapid temperature control. Biotechniques. Jan. 1997;22(1):176-81.
Zhang et al., An amplification and ligation-based method to scan for unknown mutations in DNA. Hum Mutat. Aug. 2002;20(2):139-47.
Zhao et al., p53 gene mutations in non-small cell lung cancer detected by polymerase chain reaction single-strand conformation polymorphism analysis. Chin Med Sci J. Sep. 1999;14(3):134-7.
International Preliminary Report on Patentability for PCT/US2014/047373 dated Feb. 4, 2016.

(56) References Cited

OTHER PUBLICATIONS

[No Author Listed] Integrated DNA Technologies Molecular Facts and Figures [online] [retrieved on Feb. 17, 2015] retrieved from https://www.idtdna.com/pages/docs/educational-resources/molecular-facts-and-figures.pdf?sfvrsn=4.

Beau-Faller et al., Detection of K-Ras mutations in tumour samples of patients with non-small cell lung cancer using PNA-mediated PCR clamping. Br J Cancer. Mar. 24, 2009;100(6):985-92. doi:10.1038/sj.bjc.6604925.

Behn et al., Simple and reliable factor V genotyping by PNA-mediated PCR clamping. Thromb Haemost. Apr. 1998;79(4):773-7.

Genbank Accession No. L32764.1—Human coagulation factor v gene, exon 10 (GI: 488093, submitted Nov. 10, 1994, retrieved on Feb. 16, 2015 from http://www.ncbi.nlm.nih.gov/nuccore/L32764.1).

Igloi, Variability in the stability of DNA-peptide nucleic acid (PNA) single-base mismatched duplexes: real-time hybridization during affinity electrophoresis in PNA-containing gels. Proc Natl Acad Sci U S A. Jul. 21, 1998;95(15):8562-7.

Orum, PCR clamping. Curr Issues Mol Biol. Jan. 2000;2(1):27-30.

Schuermann et al., PNA clamping techniques for the determination of oncogene mutations. Methods Mol Biol. 2002;208:165-79.

Schuermann, Detection of K-ras and p53 mutations by "mutant-enriched" PCR-RFLP. Methods Mol Med. 2003;75:325-33.

Canadian Office Action for Application No. 2,830,361 dated Feb. 19, 2018.

Corless et al., Allele-specific polymerase chain reaction for the imatinib-resistant KIT D816V and D816F mutations in mastocytosis and acute myelogenous leukemia. J Mol Diag Nov. 2006;8(5):604-612.

Makrigiorgos et al., Multiplex Amplification Coupled with COLD-PCR and High Resolution Melting Enables Identification of Low-Abundance Mutations in Cancer Samples with Low DNA Content. J. of Molecular Diagnostics. Mar. 2, 2011;13(2):220-32.

Extended European Search Report for EP 17196718.5 dated May 14, 2018.

Bunyan et al., Different denaturation rates between methylated and non-methylated genomic DNA can result in allele-specific PCR amplification. Open J. Gen. Sep. 2011;1:13-14.

Riesewijk et al., Monoallelic expression of human PEG1/MEST is paralleled by parent-specific methylation in fetuses. Genomics. Jun. 1, 1997;42(2):236-44.

Walsh et al., Preferential PCR amplification of alleles: mechanisms and solutions. PCR Methods Appl. May 1992;1(4):241-50.

Ladas et al. Multiplexed Elimination of Wild-Type DNA and High-Resolution Melting Prior to Targeted Resequencing of Liquid Biopsies. Clin Chem. 2017;63(10):1605-1613. doi:10.1373/clinchem.2017.272849.

Owczarzy et al., Predicting stability of DNA duplexes in solutions containing magnesium and monovalent cations. Biochemistry. May 13, 2008;47(19):5336-53. doi: 10.1021/bi702363u. Epub Apr. 19, 2008.

* cited by examiner

Design of ice-COLD-PCR-solid support (bead)

Prior to ice-COLD-PCR: mutant target sequence is in minority relative to wild-type target sequence During ice-COLD-PCR on solid support (bead) within emulsion: the proximity of target sequences to wild-type sequences facilitates efficient hybridization and hetero-duplex formation

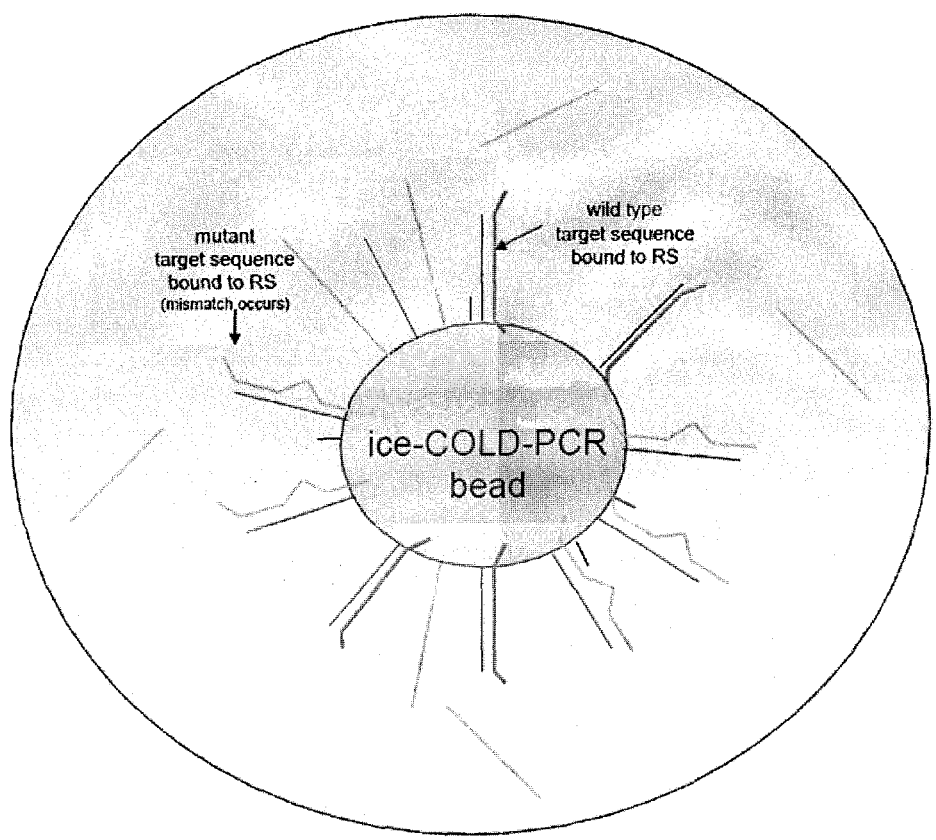

Fig. 4

- Following ice-COLD-PCR: amplified mutant target sequences are now in majority relative to wild-type target sequences
  - Some mutant sequences are bound to the bead, while others are free-floating
  - Most primers are consumed during synthesis

Heteroduplexes denature first and re-associate last

Capture and isolation of mutation (or DNA damage)-enriched single stranded sequences by primer extension

Capture and isolation of mutation (or DNA damage)-enriched single stranded sequences by hybridization to excess biotinylated reference

Capture and selective biotinylation of single-stranded sequences via selective ligation at critical temperature

Kras double mutation CC>AA
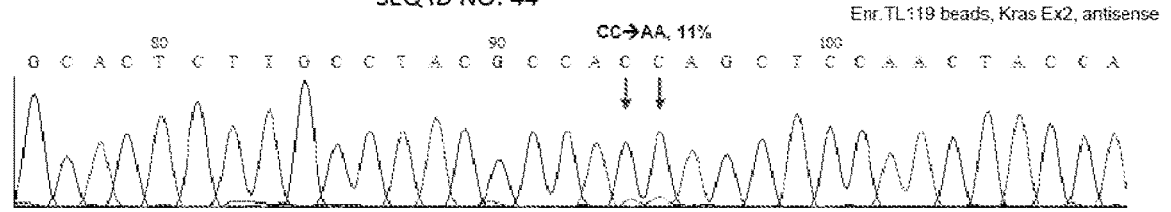
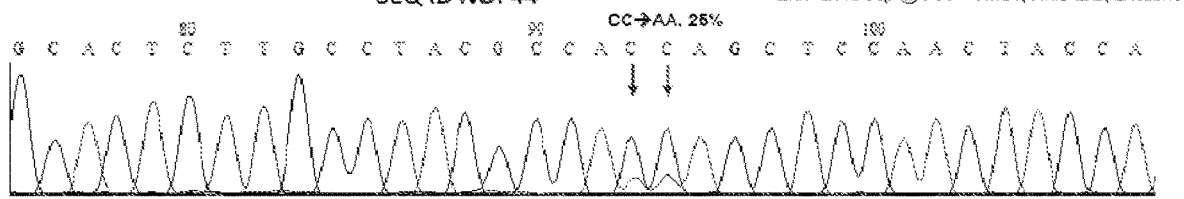
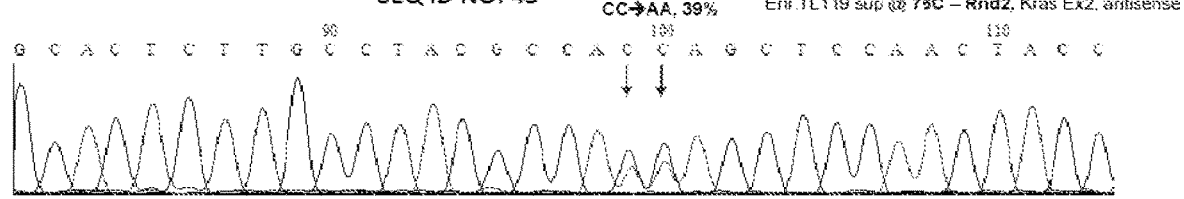
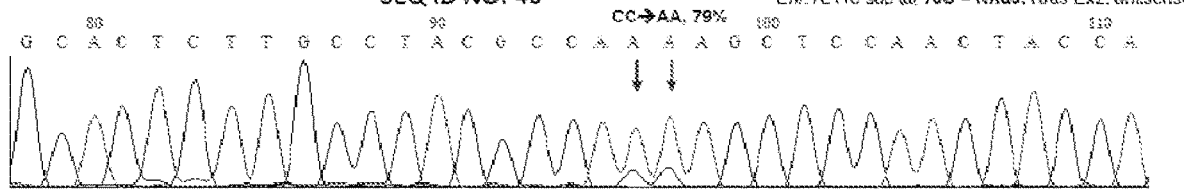
Fig. 17

Bead purification of KRAS double mutation (CC>AA) from TL119 patients

Enrichment of KRAS single point mutation (C>A) from SW480 mutant DNA mixtures

Enrichment of KRAS Single point mutant (C>T) at various denaturation temperatures

METHODS AND COMPOSITIONS TO ENABLE MULTIPLEX COLD-PCR

RELATED APPLICATIONS

This application is a national stage filing under 35 U.S.C. § 371 of international application PCT/US2012/031527, filed Mar. 30, 2012, which was published under PCT Article 21(2) in English, which claims the benefit under 35 U.S.C. § 119(e) of U.S. provisional application Ser. No. 61/470,022, filed Mar. 31, 2011, the disclosure of each referenced application is incorporated by reference herein in its entirety.

FEDERALLY SPONSORED RESEARCH

This invention was made with government support under grants CA138280, R21 CA175542, R21 CA155615, and R21 CA151164 awarded by the National Institutes of Health. The government has certain rights in the invention.

BACKGROUND OF THE INVENTION

There is an increasing demand for rapid and sensitive molecular assays to screen a panel of critical cancer gene mutations for personalized diagnosis and treatment. Of particular interest are certain mutations which sensitize tumors to drug treatment, predict a lack of response or predict emergence of resistance. The co-occurrence of mutations can complicate matters. An example is provided in reference to lung cancer. Mutations in the ATP binding domain of EGFR predict response to the small tyrosine kinase inhibitor drugs erlotinib and gefitinib. Such mutations, however, do not tell a complete story. Co-occurring mutations in codons 12 and 13 of KRAS predict resistance to anti-EGFR agents, even in the presence of mutations in the ATP binding domain of EGFR. Furthermore, secondary EGFR mutations, especially the mutation T790M (which is present in low frequency), limit the benefit of EGFR targeted therapy due to drug resistance upon prolonged treatment. Similar co-occurring cancer gene mutations have been identified in other cancer types as well. Accordingly, it is desirable to profile individual tumors for potential mutations in several genes simultaneously.

Another major challenge in molecular diagnosis of human cancer is the remarkable heterogeneity of tumor samples that are to be screened. Human cancer is known to harbor a wide range of chromosomal rearrangements including large deletions, insertions, and translocations, as well as large numbers of somatic mutations. Excluding clonal mutations, most somatic mutations are random and present in only a small fraction of the cancer cells in a tumor. However, these low-level mutations could contribute to tumor progression, and in clinical settings, rapid emergence of resistance to treatment. Contamination of tumor cells with excess normal cells further complicates mutation detection. While reliable high throughput screening methods for germline or high-prevalence somatic mutations have been described (Thomas, R. K., et al. (2007) Nat Genet, 39, 347-351; Chou, L. S., et al. (2005) Am J Clin Pathol, 124; 330-338; Thomas, R. K., et al. (2006) Nat Med, 12; 852-855) detection of low-prevalence somatic mutations in tumors with heterogeneity, stromal contamination or in bodily fluids is still problematic, and there is a great need for effective techniques to identify a low percent of variant DNA sequences ('target sequences') in the presence of a large excess of non-variant sequences ('reference sequences).

To tackle the problems of detecting low level mutations in clinical samples, new forms of PCR (co-amplification at lower denaturation temperature or COLD-PCR and improved and complete enrichment COLD PCR or ice-COLD-PCR) that amplify preferentially mutation-containing sequences over wild-type alleles have been recently described (Li J, Wang L, Mamon H, Kulke M H, Berbeco R, Makrigiorgos G M. Replacing PCR with COLD-PCR enriches variant DNA sequences and redefines the sensitivity of genetic testing. Nat Med 2008; 14:579-84; Milbury C A, Li J, Makrigiorgos G M. Ice-COLD-PCR enables rapid amplification and robust enrichment for low-abundance unknown DNA mutations. Nucleic Acids Res; 39:e2). It has been demonstrated that the detection limit of several downstream mutation detection and mutation scanning techniques including sequencing, pyrosequencing, dHPLC, high resolution melting and genotyping can be highly improved via COLD-PCR (Li J, Milbury C A, Li C, Makrigiorgos G M. Two-round coamplification at lower denaturation temperature-PCR(COLD-PCR)-based sanger sequencing identifies a novel spectrum of low-level mutations in lung adenocarcinoma. Hum Mutat 2009; 30:1583-90; Milbury C A, Li J, Makrigiorgos G M. COLD-PCR-enhanced high-resolution melting enables rapid and selective identification of low-level unknown mutations. Clin Chem 2009; 55:2130-43; Mancini I, Santucci C, Sestini R, Simi L, Pratesi N, Cianchi F, et al. The use of COLD-PCR and high-resolution melting analysis improves the limit of detection of KRAS and BRAF mutations in colorectal cancer. J Mol Diagn; 12:705-11; Boisselier B, Marie Y, Labussiere M, Ciccarino P, Desestret V, Wang X, et al. COLD PCR HRM: a highly sensitive detection method for IDH1 mutations. Hum Mutat; 31:1360-5).

COLD-PCR differentiates between mutant and wild type sequences by preferentially amplifying those amplicons that have a lower melting temperature. Thus, the cycling conditions applied during COLD-PCR induce the formation of mutant:wild-type heteroduplexes during amplification and then denature selectively these heteroduplexes at a critical denaturation temperature, Tc, that favors denaturation of heteroduplexes over homoduplexes, (full-COLD-PCR). Successful enrichment during COLD-PCR is dependant upon the critical denaturation temperature Tc applied for a given amplicon. At the Tc, the target-reference sequence duplexes are substantially denatured, whereas the target-target duplexes and the reference-reference sequence duplexes are substantially undenatured. The value of Tc for a given amplicon is usually just below the value of the melting temperature Tm of the amplicon. To a first approximation, Tc is empirically determined from the melting temperature Tm of an amplicon according to the formula Tc=Tm−1 (Li J, Makrigiorgos G M. COLD-PCR: a new platform for highly improved mutation detection in cancer and genetic testing. Biochem Soc Trans 2009; 37:427-32). For a more precise determination of the optimal Tc, an experimental procedure can be followed to titrate the denaturation temperature over many reactions and determine the optimal Tc as described herein.

SUMMARY OF THE INVENTION

Multiplexing COLD-PCR to enrich mutations over multiple amplicons would be of great value as it would enable the simultaneous screening of a panel of DNA regions and would ensure identification of low-level mutations. However, this is technically difficult, due to the fact that different amplicons possess different melting properties, and therefore a different Tc. To amplify via COLD-PCR several DNA fragments simultaneously and achieve substantial mutation enrichment on all of them at the same time, the Tm and/or Tc of all the DNA fragments needs to be regulated to be substantially the same, e.g., to within ~0.2° C. of each other. The formation of primer-dimers, whenever more than one set of primers are included, is another problem which is common to multiplex PCR applications.

The present invention, is directed to methods, and compositions for multiplexing COLD-PCR/ice-COLD-PCR to enrich simultaneously several low abundance alleles (mutant target sequences) from a sample. The present invention, in one aspect, relates to multiplex COLD-PCR/ice-COLD-PCR amplification performed in a space-constrained manner (e.g. in microdroplets, micro-chambers, in pico-litter volumes emulsion, on micro-beads, on glass, or on alternative solid supports). In some embodiments, a population of DNA fragments having substantially the same melting temperature (iso-Tm DNA amplicons) are simultaneously prepared prior to initiating COLD-PCR/ice-COLD-PCR. The iso-Tm DNA amplicons, in the event there exist both mutant and wild-type sequences present, will typically generate mutant: wild-type heteroduplexes that have substantially the same critical denaturation temperature (iso-Tc DNA amplicons). In some embodiments, the primers are designed such that a population of DNA amplicons, in the event there exist both mutant and wild-type sequences present, having substantially the same critical denaturation temperature (iso-Tc DNA amplicons) are simultaneously prepared prior to initiating COLD-PCR/ice-COLD-PCR. In some embodiments, COLD-PCR/ice-COLD-PCR amplification is performed on DNA fragments that have different melting temperatures, and therefore different critical denaturation temperatures, in a graded temperature approach such that mutation enrichment is achieved on all diverse DNA fragments simultaneously (temperature-independent COLD-PCR or TI-COLD-PCR).

In one aspect of the invention, methods and products are provided for preparing iso-Tm and/or iso-Tc amplicons from a host's nucleic acids.

One method concerns preparing nucleic acids for subsequent processing. The subsequent processing, for example, may be next generation sequencing. The method involves contacting a host's nucleic acids with at least two pairs of nucleic acid primers, each pair of primers binding to the nucleic acids and generating under nucleic acid amplification conditions an amplicon that is a copy of a region of interest of the nucleic acids, wherein the amplicon generated by one pair of primers is different from the amplicon generated from each other pair of primers. The primers are selected such that the amplicons generated by different pairs of primers have substantially the same Tm and/or substantially the same Tc. Nucleic acid amplification conditions are applied to form the amplicons having substantially the same Tm and/or Tc from the primers and nucleic acids. The nucleic acid amplification conditions are applied for at least 3 cycles of amplification, whereby the presence of the regions of interest are enriched relative to non-amplified genomic DNA regions. More typically, the nucleic acid amplification conditions are applied for at least 5, at least 6, at least 7, at least 8, at least 9 or at least 10 cycles of amplification, whereby the presence of the regions of interest are enriched. In this manner, numerous copies of amplicons representing nucleic acid regions of interest are provided, the amplicons having the same Tm and/or Tc.

In some embodiment, the at least two pairs of nucleic acid primers is at least 5, 10, 15, 20, 30, 40, 50, 100, 200, 500, 1,000, 5,000, 10,000 or 30,000 pairs of primers. In this manner, the amplicons represent at least 10, 15, 20, 30, 40, 50, 100, 200, 500, 1,000, 5,000, 10,000 or 30,000 different regions of interest, all of the amplicons having substantially the same Tm and/or Tc. In some embodiments, the regions of interest comprise a sequence known to be present if disease exists, known to be predictive of the development of disease or known to be predictive of successful treatment of disease with a drug. Only as examples, the disease can be cancer, cardiovascular disease, diabetes, obesity, neurological disorders, or diseases screened-for in maternal blood for prenatal diagnosis.

In some embodiments, the iso-Tm and/or iso-Tc amplicons, once prepared, can then be used in COLD-PCR or ice-COLD-PCR procedures, followed by sequencing. In one embodiment, the COLD-PCR or ice-COLD-PCR procedure is carried out in a space constrained fluid or at a space constrained site on a solid surface. In one embodiment, the procedure is carried out in micro-droplets, each micro-droplet containing only a single pair of primers specific for generating amplicons of a single region of interest. The droplet also contains at least the target sequence to which the pair of primers bind. As will be described in greater detail below, the droplet may be produced in any number of ways. Many droplets can be prepared, different droplets containing different pairs of primers, but all the primers, as described above, generating amplicons that are iso-Tm and/or iso-Tc. COLD-PCR or ice-COLD-PCR then can be performed on hundreds, thousands, or even millions of such droplets simultaneously.

In some embodiments, the method further involves enriching nucleic acids for regions of interest. This can be done in some embodiments prior to carrying out a method of preparing iso-Tm and/or iso-Tc amplicons. This can be done in some embodiments after carrying out a method for preparing iso-Tm and/or iso-Tc amplicons. In one embodiment, nucleic acid regions of interest are enriched by contacting the nucleic acids with a plurality of capture oligonucleotides that bind to different regions of interest, permitting binding of the capture oligonucleotides to the regions of interest, and isolating the capture oligonucleotides with the regions of interest bound thereto from remaining nucleic acids. In some embodiments, the capture oligonucleotides are biotinylated at one end. In some embodiments, the capture oligonucleotides are attached to beads. In some embodiments, the capture oligonucleotides are attached as a microarray to a surface.

In some embodiments, the method further comprises enriching the nucleic acids for regions of interest by contacting the nucleic acids with molecular inversion probes, circularizing the molecular inversion probes such that they encompass the regions of interest, removing non-circularized DNA, and amplifying the regions of interest from the circularized, isolated molecular inversion probes.

According to another aspect of the invention, a method for enriching for target sequences is provided. The method comprises:
capturing mutant sequences and wild type sequences within a plurality of droplets, exposing the mutant sequences and wild type sequences within the droplets to a reaction mixture containing pairs of nucleic acid primers, each pair of primers generating under nucleic acid amplification conditions an amplicon that is a copy of a target sequence, wherein the amplicon generated by one pair of primers is different from the amplicon generated from each other pair of primers, wherein the amplicons have substantially the same Tm and/or Tc, and wherein each droplet is exposed to only one pair of primers, subjecting the mutant sequences and wild type sequences in the reaction mixture to a first denaturing temperature that is above the melting temperature of the mutant sequences and wild type sequences, reducing the temperature of the reaction mixture to permit the formation of a mutant strand/wild type strand duplexes, subjecting the duplexes in the reaction mixture to a critical denaturation temperature Tc that is below the Tm of the duplex formed by wild-type target sequences, to permit selective denaturation of the duplexes containing mutant sequences, without denaturation of the duplexes formed by wild-type target sequences, reducing the temperature of the reaction mixture in the presence of pairs of nucleic acid primers and permitting the primers to anneal to the mutant sequences, and extending the primers to enrich the mutant sequences.

According to another aspect of the invention, a method for enriching for mutant target sequences is provided. The method comprises:

capturing target sequences within a plurality of droplets in such a manner that each droplet contains only copies of a single reference sequence plus only copies of the corresponding target sequence, exposing the target and reference sequences within the droplets to a reaction mixture containing pairs of nucleic acid primers corresponding to the target captured within each droplet and each pair of primers generating under nucleic acid amplification conditions an amplicon that is a copy of a target sequence, wherein the amplicon generated by one pair of primers is different from the amplicon generated from each other pair of primers, wherein the amplicons have substantially the same Tm and/or Tc, and wherein each droplet is exposed to only one pair of primers, only the corresponding region of interest and only the reference sequence corresponding to the region of interest, subjecting the target sequences and the reference sequences in the reaction mixture to a first denaturing temperature that is above the melting temperature of the target sequences and the reference sequences, reducing the temperature of the reaction mixture to permit the formation of a target strand/reference strand duplexes, subjecting the duplexes in the reaction mixture to a critical denaturation temperature Tc that is below the Tm of the duplex formed by wild-type target sequences and the reference sequences, to permit selective denaturation of the duplexes containing sequence variants, without denaturation of the duplexes formed by wild-type target sequences with the reference sequences, reducing the temperature of the reaction mixture in the presence of pairs of nucleic acid primers and permitting the primers to anneal to the target sequences, and extending the primers to enrich the mutant target sequences.

The reference sequence is synthetically formed and corresponds to the target sequence. In embodiments, the reference sequence is a copy of at least a portion of the wild-type target sequence. In some embodiments, the reference sequence is the same as the sequence of the target wild-type sequence.

Having described certain methods of the invention, it should be apparent that there are novel products that are useful in practicing the invention as well as novel reaction mixtures produced in the course of practicing the invention.

In one aspect of the invention, a kit is provided. The kit is a package containing at least two pairs of nucleic acid primers. Each pair of primers binds to a host's nucleic acids and generates under nucleic acid amplification conditions an amplicon that is a copy of a region of interest of the host's genome, wherein the amplicon generated by one pair of primers is different from the amplicon generated from each other pair of primers, and wherein the amplicons have substantially the same Tm and/or Tc In some embodiments, each amplicon is at least 40 nucleotides in length. In some embodiments, the host is a human and each region of interest is known to have or is suspected of having a sequence variation among humans. In some embodiments, the host is a human and at least one region of interest is known to have or is suspected of having a variation at a single nucleotide position within the region of interest. In some embodiments, the host is a bacteria, parasite or virus and each region of interest is known to have or is suspected of having a sequence variation.

In some embodiments, one primer of each pair of primers is attached to a solid substrate, e.g., a bead. In other embodiments, both primers of each pair of primers are attached to a substrate. In some embodiments, the host is a human and the regions of interest comprise a sequence known to be present when there is disease, known to be predictive of disease or known to be predictive of successful treatment of disease with a drug. In some embodiments, one or both primers from each pair of primers have 5'-terminal ends that do not bind the region of interest, wherein the terminal ends of forward primers have the same sequence and the terminal ends of reverse primers have the same sequence. In some embodiments, the at least two pairs of nucleic acid primers is at least 5, 10, 15, 20, 30, 40, 50, 100, 200, 500, 1,000, 5,000, 10,000 or 30,000 pairs of primers. In some embodiments, the kit further comprises a polymerase. In some embodiments, the kit further comprises at least two capture oligonucleotides that bind to different regions of interest. In some embodiments, the kit further comprises beads.

In some embodiments, the kit further comprises at least two different reference oligonucleotides, each different reference oligonucleotide having a sequence identical to a portion of, or the whole of, a strand of a corresponding amplicon. Each different reference oligonucleotide can exclude the sequence occurring at the ends of the strand of its corresponding amplicon, and each different reference oligonucleotide can be substantially non-overlapping with the pair of primers that generate its corresponding amplicon. In some embodiments, each reference oligonucleotide is biotinylated at one end. In any of the foregoing embodiments, the reference sequence can be a capture sequence. In some embodiments, the kit further comprises streptavidin coated beads.

In some embodiments, one pair of each pair of primers is attached to a bead and the kit further comprises at least two different reference oligonucleotides, each different reference oligonucleotide having a sequence identical to a portion of a strand of a corresponding amplicon. Each different reference oligonucleotide can exclude the sequence occurring at the ends of the strand of its corresponding amplicon. Each different reference oligonucleotide can be substantially non-overlapping with the pair of primers that generate its corresponding amplicon. In some embodiment, each reference oligonucleotide is biotinylated at one end. In some embodiments, the beads are streptavidin coated.

Finally, it is also known that some genomic regions can be polymorphic (i.e. contain Single Nucleotide Polymorphisms, SNPs, and thus there may be at least two different versions of each region of interest in human genomic DNA). Accordingly, in some embodiment there can be at least two different versions of each reference oligonucleotide, each version representing the different polymorphisms known to exist for a region of interest in genomic DNA, e.g. one version having a G and another having an A for a G/A SNP, and so forth).

According to one aspect of the invention, a kit comprising a pair of nucleic acid primers, and a reference oligonucleotide is provided. The pair of primers binds to a host's nucleic acids and generates under nucleic acid amplification conditions an amplicon that is a copy of a region of interest of the host's genome. The reference oligonucleotide has a sequence identical to a portion of a strand of the amplicon. The reference oligonucleotide can exclude the sequence occurring at the ends of the strand of the amplicon. The reference oligonucleotide can be substantially non-overlapping with either primer. In some embodiments, the reference oligonucleotide is biotinylated at one end. In some embodiments, the kit further comprises steptavidin coated beads.

According to one aspect of the invention, a composition of matter comprising, a bead, a reference oligonucleotide attached to the bead, and a corresponding primer attached to the bead is provided. The reference oligonucleotide attached to the bead has a sequence that is a portion of a strand of an amplicon derived from a host's nucleic acids. The reference oligonucleotide can exclude the sequence which is at the ends of the strand of the amplicon. The corresponding primer attached to the bead is the complement of the sequence at one end of the strand of the amplicon and does not overlap substantially with the reference sequence. In some embodiments, the reference oligonucleotide is a plurality of reference oligonucleotides having different sequences, and wherein the primer is the complement of the sequence at one end of the strand of only a single amplicon, and wherein the amplicon corresponds to the capture oligonucleotide bound to the bead. Finally, in another embodiment, both primers for amplifying a given region of interest can be attached to the bead.

According to an aspect of the invention, a reaction mixture comprising at least two pairs of nucleic acid primers is provided. Each pair of primers binds to a host's nucleic acids and generates under nucleic acid amplification conditions an amplicon that is a copy of a region of interest of the host's genome, wherein the amplicon generated by one pair of primers is different from the amplicon generated from each other pair of primers, and wherein the amplicons have substantially the same Tm and/or Tc In some embodiments, each amplicon is at least 40 nucleotides in length. In some embodiments, the host is a human and each region of interest is known to have or is suspected of having a sequence variation among humans. In some embodiments, the host is a human and at least one region of interest is known to have or is suspected of having a variation at a single nucleotide position within the region of interest. In some embodiments, the host is a bacteria, parasite or virus and each region of interest is known to have or is suspected of having a sequence variation.

In some embodiments, one primer of each pair of primers is attached to a substrate, e.g., a bead. In some embodiments, both primers of each pair of primers are attached to a substrate. In some embodiments, the host is a human and the regions of interest comprise a sequence known to be associated with a disease, known to be predictive of a disease or known to be predictive of successful treatment with a drug. In some embodiments, the pairs of primers have terminal ends that that do not bind the region of interest, wherein the terminal ends of the forward primers have the same sequence and the terminal ends of the reverse primers have the same sequence. In some embodiments, the at least two pairs of nucleic acid primers is at least 5, 10, 15, 20, 30, 40, 50, 100, 200, 500, 1,000, 5,000, 10,000 or 30,000 pairs of primers. In some embodiments, the reaction mixture further comprises a polymerase.

In some embodiments, the reaction mixture comprises the iso-Tm and/or iso-Tc amplicons generated by the pairs of primers.

According to one aspect of the invention, a reaction mixture comprising at least five different amplicons is provided. Each amplicon is a copy of a different region of interest of a host's genome, wherein each amplicon is present in at least 10 copies, and wherein the amplicons have substantially the same Tm and/or Tc. In some embodiments, substantially all the amplicons in the reaction mixture have substantially the same Tm and/or Tc.

In some embodiments, the host is a human and each region of interest is known to have or is suspected of having a sequence variation among humans. In some embodiments, the host is a human and at least one region of interest is known to have or is suspected of having a variation at a single nucleotide position within the region of interest. In some embodiments, the host is a bacteria, parasite or virus and each region of interest is known to have or is suspected of having a sequence variation.

In some embodiments, the reaction mixture further comprises a bead to which is attached a nucleic acid having a reference sequence at least in part identical to a strand of an amplicon. In some embodiments, the host is a human and the regions of interest comprise a sequence known to be associated with cancer, known to be predictive of disease or known to be predictive of successful treatment with a drug. In some embodiments, the at least 5 different amplicons is at least 10, 15, 20, 30, 40, 50, 100, 200, 500, 1,000, 5,000, 10,000 or 30,000 different amplicons. In some embodiments, the reaction mixture further comprises pairs of nucleic acid primers, each pair of primers generating under nucleic acid amplification conditions one of the at least 5 amplicons. In some embodiments, the reaction mixture further comprises heteroduplexes, wherein the heteroduplexes are formed of amplicons having substantially the same sequence.

According to another aspect of the invention, a method for enriching for mutant target sequences is provided. The method comprises (a) exposing a plurality of target sequences to a reaction mixture containing pairs of nucleic acid primers, each pair of primers generating under nucleic acid amplification conditions an amplicon that is a copy of a target sequence, wherein the amplicon generated by one pair of primers is that of a different target from the amplicon generated from each other pair of primers, (b) subjecting the target sequences in the reaction mixture to a denaturing temperature that is above the melting temperature of wild-type target sequences, (c) reducing the temperature of the reaction mixture to permit the formation of mutant:wild-type target strand heteroduplexes, (d) subjecting the heteroduplexes in the reaction mixture to a first critical denaturation temperature Tc that is below the lowest Tm of the duplex formed by wild-type target sequences, to permit selective denaturation of the heteroduplexes containing sequence variants, without denaturation of the duplexes formed by wild-type target sequences, (e) reducing the temperature of the reaction mixture in the presence of pairs of nucleic acid primers and permitting the primers to anneal to the mutant target sequences, (f) extending the primers to enrich the mutant target sequences, and (g) repeating steps (d) to (f) at least once at a second critical denaturation temperature which is above the first critical denaturation temperature to permit amplification of mutant target sequences having wild-type:mutant Tc at the second critical denaturation temperature.

In some embodiments, the reaction mixture comprises a reference sequence that is the same as the wild-type target sequence.

In some embodiments, steps (d) to (f) are repeated at least 2, 3, 4, 5, 10, 15, 20, 25, 30, 35, 40, 45, or 50 times at successively increasing critical denaturation temperatures. In some embodiment, at each critical denaturation temperature, steps (d) to (f) are repeated for two or more cycles. In some embodiments, at each critical denaturation temperature, steps (d) to (f) are repeated for 5-40 cycles. In some embodiments, at each critical denaturation temperature, steps (d) to (f) are repeated for 10-30 cycles.

According to another aspect of the invention, a method for enriching for mutant target sequences is provided. The method comprises (a) exposing the target sequences and reference sequences to a reaction mixture containing pairs of nucleic acid primers, each pair of primers generating under nucleic acid amplification conditions an amplicon that is a copy of a target sequence, wherein the amplicon generated by one pair of primers is that of a different target from the amplicon generated from each other pair of primers, (b) subjecting the target sequences and the reference sequences in the reaction mixture to a denaturing temperature that is above the melting temperature of the target sequences and the reference sequences, (c) reducing the temperature of the reaction mixture to permit the formation of a target strand/reference strand duplexes, (d) subjecting the duplexes in the reaction mixture to a first critical denaturation temperature Tc that is below the lowest Tm of the duplex formed by wild-type target sequences and the reference sequences, to permit selective denaturation of the duplexes containing sequence variants, without denaturation of the duplexes formed by wild-type target sequences with the reference sequences, (e) reducing the temperature of the reaction mixture in the presence of pairs of nucleic acid primers and permitting the primers to anneal to the target sequences, (f) extending the primers to enrich the target sequences, (g) repeating steps (d) to (f) at least once at a second critical denaturation temperature which is above the first critical denaturation temperature to ensure amplification of all target sequences over references sequences.

In some embodiments, the reference sequence is the same as the wild-type target sequence.

In some embodiments, steps (d) to (f) are repeated at least 2, 3, 4, 5, 10, 15, 20, 25, 30, 35, 40, 45, or 50 times at successively increasing critical denaturation temperatures. In some embodiments, at each critical denaturation temperature, steps (d) to (f) are repeated for two or more cycles. In some embodiments, at each critical denaturation temperature, steps (d) to (f) are repeated for 5-40 cycles. In some embodiments, at each critical denaturation temperature, steps (d) to (f) are repeated for 10-30 cycles.

According to another aspect of the invention, a method for enriching for target sequences is provided. The method comprises (a) exposing the target sequences and reference sequences to a reaction mixture containing pairs of nucleic acid primers, each pair of primers generating under nucleic acid amplification conditions an amplicon that is a copy of a target sequence and a reference sequence, wherein the amplicon generated by one pair of primers is to a different target sequence from the amplicon generated from each other pair of primers, (b) subjecting the target sequences and the reference sequences in the reaction mixture to a denaturing temperature that is above the melting temperature of the target sequences and the reference sequences, (c) reducing the temperature of the reaction mixture in the presence of pairs of nucleic acid primers and permitting the primers to anneal to the target sequences, (d) extending the primers to enrich the target sequences, (e) subjecting the duplexes in the reaction mixture to a first critical denaturation temperature Tc that is below the lowest Tm of the duplex formed by wild-type target sequences and the reference sequences, to permit selective denaturation of the duplexes containing sequence variants, without denaturation of the duplexes formed by wild-type target sequences with the reference sequences (g) repeating steps (c) to (e) at least once at a second critical denaturation temperature which is above the first critical denaturation temperature to ensure selective amplification of all target sequences that contain sequence variants over wild type sequences.

In some embodiments, the reference sequence is the same as the wild-type target sequence.

According to another aspect of the invention, a method for preparing a single stranded mutant target sequence from a mixture of target sequences suspected of containing both the mutant target sequence and a wild type target sequence is provided. The method comprises:

(i) subjecting the target sequences to a denaturing temperature that is above the melting temperature of the target sequences, thereby forming a mixture containing the single stranded mutant sequence and single stranded wild type sequences, the mixture characterized by a ratio of single stranded mutant sequences relative to single stranded wild type sequences, (ii) contacting the mixture with an excess of a reference sequence complementary to the wild type sequence, (iii) reducing the temperature to permit formation of target strand/reference strand duplexes, wherein the duplexes include mutant strand/reference strand duplexes and wild type strand/reference strand duplexes, (iv) subjecting the target strand/reference strand duplexes to a critical denaturation temperature Tc that is below the melting temperature of the wild type strand/reference strand duplexes, to permit selective denaturation of mutant strand/reference strand duplexes, whereby the ratio of single stranded mutant target sequences relative to single stranded wild type target sequences is increased.

In some embodiments, the method for preparing a single stranded mutant target sequence further comprises (v) reducing the temperature to a critical hybridization temperature that permits selective formation of wild-type target sequence/reference sequence duplexes relative to formation of mutant sequence/reference sequence duplexes. In some embodiments, (iv) and (v) are repeated at least 1, 2, 3, 5, 10, 50, 75, 100, 200, 300, 400, 500, 600, 700, 800, 900, or 1000 times to further enrich for the single stranded mutant target sequences.

In some embodiments, the method for preparing a single stranded mutant target sequence further comprises (vi) after (iv), removing wild type strand/reference strand duplexes, (vii) repeating (iii), (iv) and (vi) at least 1, 2, 3, 5, 10, 50, 75, 100, 200, 300, 400, 500, 600, 700, 800, 900, or 1000 times to further enrich for the single stranded mutant target sequences.

In some embodiments, the method for preparing a single stranded mutant target sequence further comprises
(viii) after (iv), removing reference sequences,
(ix) adding additional excess of reference sequence,
(x) repeating (iii), (iv), (viii) and (ix) at least 1, 2, 3, 5, 10, 50, 75, 100, 200, 300, 400, 500, 600, 700, 800, 900, or 1000 times to further enrich for the single stranded mutant target sequences.

In any of the foregoing embodiments of the method for preparing a single stranded mutant target sequence, the reference sequences may be attached to particles. In any of the foregoing embodiments of the method for preparing a single stranded mutant target sequence, the reference sequences are attached to magnetic particles. In some embodiments, the target sequences in (i) are contacted with an excess of at least two different reference sequences, each different reference sequence being complementary to a different wild-type target sequence, and the duplexes formed by the wild type sequences/reference sequences having substantially the same melting temperature, or substantially the same critical denaturation temperature (Tc). In some embodiments, the target sequences in (i) are contacted with an excess of at least 10, 15, 20, 30, 40, 50, 100, 200, 500, or 1000 different reference sequences.

In any of the foregoing embodiments of the method for preparing a single stranded mutant target sequence, the method further comprises detecting the single stranded mutant target sequences. In any of the foregoing embodiments of the method for preparing a single stranded mutant target sequence, the method further comprises isolating the single stranded mutant target sequences.

In some embodiments, the single stranded mutant target sequences are isolated by:
contacting the single stranded mutant target sequences with primers,
reducing the temperature to permit binding of the primers to single stranded mutant target sequences,
enzymatically extending the primers using biotinylated nucleotides,
capturing the biotinylated sequences on a streptavidin-coated solid surface, and removing any unbound sequences, and
releasing the single-stranded mutant target sequences from the solid surface.

In some embodiments, the single stranded mutant target sequences are isolated by:
adding an excess of biotinylated reference sequences,
rapidly reducing the temperature below 50-55° C. to permit formation of single stranded mutant target sequence/biotinylated reference sequence duplexes,
treating with exonuclease I to eliminate excess reference sequence,
capturing the biotinylated sequences on a streptavidin-coated solid surface, and removing any unbound sequences, and
releasing the single-stranded mutant target sequences from the solid surface.

In some embodiments, the single stranded mutant target sequences are isolated by:
contacting the formed duplexes with an excess of non-biotinylated adaptor and thermostable ligase at critical hybridization temperature to permit selective ligation of the non-biotinylated adaptor to the duplexes formed by wild-type target sequences with the reference sequences,
adding an excess of biotinylated adaptor and thermostable ligase,
reducing the temperature to permit formation of mutant target strand/reference strand duplexes, followed by binding of biotinylated adaptor to the formed duplexes,
capturing the biotinylated sequences on a streptavidin-coated solid surface, and removing any unbound sequences, and
releasing the single-stranded mutant target sequences from the solid surface.

In some embodiments, the single stranded mutant target sequences are isolated by:
using biotinylated reference sequences, and the duplexes formed by wild type sequence/biotinylated reference sequence are removed by capture on steptavidin-coated solid surface, thereby leaving an enriched population of single-stranded mutant target sequences.

In some embodiments, the single stranded mutant target sequences are isolated by:
attaching the reference sequences to magnetic beads and the duplexes formed by wild type sequence/reference sequence are removed by removing the magnetic beads.

In any of the foregoing embodiments, the target sequences are pre-amplified using asymmetric PCR prior to contacting with the reference sequences.

In any of the foregoing embodiments, the target sequences are contacted to the reference sequences in the presence of an organic solvent.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

FIG. 1A shows that massively parallel COLD-PCR is enabled by the RainDance™ microfluidics, to extract a selected portion of the genome while simultaneously enriching the mutations. The mutation-enriched genome is then screened via Second Generation Sequencing (SGS). FIG. 1B shows the tracing (or identification plus tracing) of tumor fingerprint in blood using plasma circulating DNA and the combined COLD-PCR-RainDance technology. FIG. 1C shows the principle of droplet formation by RainDance: Genomic DNA in droplets is merged with droplets containing primers for specific regions. Millions of nano-droplets are then PCR-amplified in a single tube, followed by massively parallel sequencing. PCR can be replaced by COLD-PCR to greatly facilitate low-abundance mutation detection via second generation sequencing (SGS). FIG. 1D shows the principle of COLD-PCR: mutant-WT heteroduplexes are formed at an intermediate temperature during PCR, following which the heteroduplexes are selectively denatured and preferentially amplified.

FIG. 4 shows an emulsion containing ice-COLD-PCR bead, captured target sequences, free forward primer and PCR ingredients (polymerase, dNTP, etc.) after ice-COLD-PCR amplification.

FIG. 17 shows RE.SE.CT enrichment for a KRAS double mutation CC>AA. At each round, the mutated sequence was enriched.

DETAILED DESCRIPTION OF THE INVENTION

Figure 1:
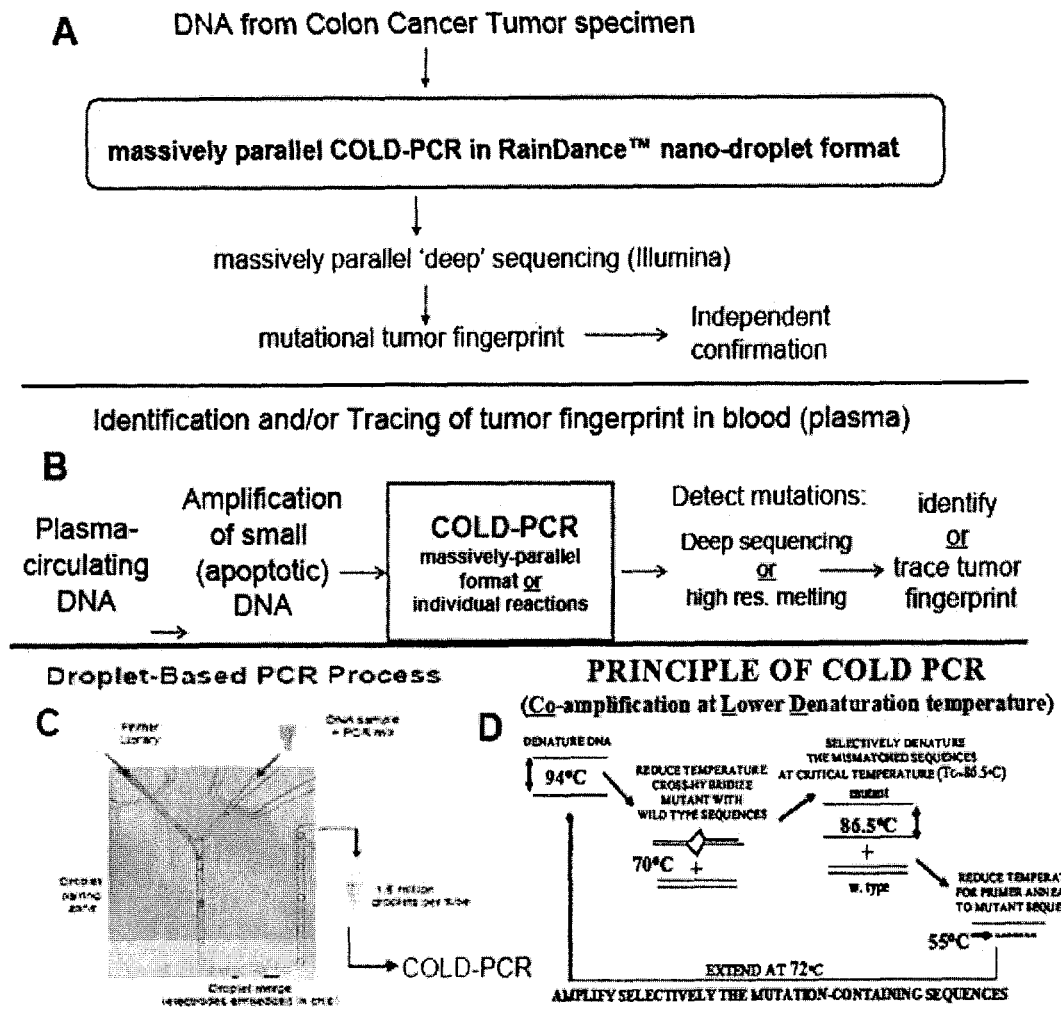
FIG. 1 shows the identification and tracing of tumor fingerprints using COLD-PCR RAINDANCE™.

A 'target region' or 'target sequence', used interchangeably herein, embraces both the mutant sequence and the wild-type sequence. In certain contexts, it may refer to one or the other. As used herein, a 'region of interest' in genomic DNA is a 'target region'. Target sequences do not necessarily need to have an exact size, i.e. one may even do a random fragmentation of the genome, or portion thereof, or some other form of restriction digestion prior to hybridization with reference sequence. The target portion that is complementary to the reference sequence will be interrogated for mutations, irrespective of what happens outside the reference sequence portion. This makes things easier, e.g. there is no need for a PCR pre-amplification step to enrich for target sequences from genomic DNA, which may introduce errors. However, if random fragmentation is used, the average fragment size should be at least 10-fold bigger than the target sequences (e.g. large fragments of 1 kb or larger can be interrogated on beads with a reference sequence of 100 bp).

'Enriching a mutant target sequence' refers to increasing the amount of a mutant target sequence and/or increasing the ratio of mutant target sequence relative to the corresponding wild type sequence in a sample. For example, where the ratio of mutant sequence to wild type sequence is initially 5% to 95% in a sample, the mutant sequence may be preferentially amplified in an amplification reaction so as to produce a ratio of 70% mutant sequence to 30% wild type sequence. Thus, there is a 14 fold enrichment of the mutant sequence relative to the wild type sequence in this hypothetical example. Generally, enrichment of a mutant target sequence results in a 2× to 200× increase in the mutant target sequence relative to the wild type sequence prior to enrichment. The enrichment of the mutant target sequence is at least a 2×, 3×, 4×, 5×, 6×, 7×, 8×, 9×, 10×, 15×, 20×, 25×, 30×, 35×, 40×, 45×, 50×, 60×, 70×, 80×, 90× 100×, 150×, 200× or more fold enrichment. Enrichment of a mutant target sequence results in a sample having 10%, 15%, 20%, 25%, 30%, 35%, 40%, 45%, 50%, 55%, 60%, 65%, 70%, 80%, 90%, 95% or more, mutant target sequence compared to wild type sequence (e.g., 10% mutant target sequence: 90% wild type sequence to 95% mutant target sequence: 5% wild type sequence).

'Mutant Target sequence' refers to a nucleic acid that is less prevalent in a nucleic acid sample than a corresponding wild type sequence. The mutant target sequence typically makes-up less than 50% of the total amount of wild type sequence+mutant sequence in a sample. The mutant target sequence may be expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the wild type sequence. For example, a sample (e.g., blood sample) may contain numerous normal cells and few cancerous cells. The normal cells contain non-mutant or wild-type alleles, while the small number of cancerous cells contain somatic mutations. In another embodiment, the invention is directed to detecting fetal DNA in a nucleic acid sample obtained from a mother. In this embodiment, the mutant target sequence is present in the fetal DNA while the more prevalent mother DNA contains the wild type sequence. As used herein, a mutant target sequence is meant to include fetal DNA obtained from a pregnant mother. In another embodiment, the invention is directed to detecting one or more methylated alleles in the presence of a large excess of unmethylated alleles, or vice versa in epigenetic analysis.

The mutant target sequence is about 17-2000 nucleotides long. In one embodiment the mutant target sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Mutant target sequences share at least 50%, 60%, 70%, 80%, 85%, 90%, 91%, 92%, 93%, 94%, 95%, 96%, 97%, 98%, 99% or more homology to the corresponding wild type sequence, but differs by at least one nucleotide from the wild type sequence. Mutant target sequences according to the invention can be amplified via PCR with the same pair of primers as those used for the wild type sequence.

'Wild type target sequence' refers to a nucleic acid that is more prevalent in a nucleic acid sample than a corresponding mutant target sequence (e.g, same region of gene but different nucleic acid sequence). The wild type sequence makes-up over 50% of the total wild type sequence+mutant target sequence in a sample. The wild type sequence can be expressed at the RNA and/or DNA level 10×, 15×, 20×, 25×, 30×, 35×, 40×, 45×, 50×, 60×, 70×, 80×, 90× 100×, 150×, 200× or more than the mutant sequence. For example, a sample (e.g., blood sample) may contain numerous normal cells and few cancerous cells. The normal cells contain non-mutant or wild-type alleles, while the small number of cancerous cells contain somatic mutations. As used herein, a "wild type strand" refers to a single nucleic acid strand of a wild type sequence. The term 'wild-type' typically refers to the most common polynucleotide sequence or allele for a certain gene in a population. Generally, the wild-type allele will be obtained from normal cells.

The wild type sequence is about 17-2000 nucleotides long. In one embodiment the wild type sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Wild type sequences will share at least 50%, 60%, 70%, 80%, 85%, 90%, 91%, 92%, 93%, 94%, 95%, 96%, 97%, 98%, 99% or more homology to the corresponding mutant target sequence, but will differ by at least one nucleotide from the mutant target sequence. Wild type sequences according to the invention can be amplified by PCR with the same pair of primers as that used for the mutant sequence.

'Allele' refers to alternative forms of a gene, portion thereof or non-coding region of DNA that occupy the same locus or position on homologous chromosomes that have at least one difference in the nucleotide sequence. The term allele can be used to describe DNA from any organism including but not limited to bacteria, viruses, fungi, protozoa, molds, yeasts, plants, humans, non-humans, animals, and archaebacteria. The alleles may be found in a single cell (e.g., two alleles, one inherited from the father and one from the mother) or within a population of cells (e.g., a wild-type allele from normal tissue and a somatic mutant allele from diseased tissue).

An allele can be 17-2000 nucleotides long. In one embodiment the allele is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Alleles will generally share 50%, 60%, 70%, 80%, 85%, 90%, 91%, 92%, 93%, 94%, 95%, 96%, 97%, 98%, 99% or more homology to each other. Alleles according to the invention can be amplified by PCR with the same pair of primers.

In one embodiment, the present invention is used to enrich a polymorphism. Any given gene may have none, one, or many allelic forms (polymorphism). Common mutational changes which give rise to alleles may be the result of natural or artificial (e.g., chemical carcinogens) deletions, additions, or substitutions of nucleotides. Each of these types of changes may occur alone, or in combination with the others, one or more times in a given sequence.

The term 'mutant' refers to a nucleotide change (i.e., a single or multiple nucleotide substitution, deletion, insertion, or methylation) in a nucleic acid sequence. A nucleic acid which bears a mutation has a nucleic acid sequence (mutant allele) that is different in sequence from that of the corresponding wild-type polynucleotide sequence. The methods of the invention are especially useful in selectively enriching several or numerous mutant alleles simultaneously. The mutant alleles can contain between 1 and 500 nucleotide sequence changes. A mutant allele may have 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400 or 500 nucleotide sequence changes compared to a corresponding wild-type allele. Typically, a mutant allele will contain between 1 and 10 nucleotide sequence changes, and more typically between 1 and 5 nucleotide sequence changes. The mutant allele will have 50%, 60%, 70%, 80%, 85%, 90%, 91%, 92%, 93%, 94%, 95%, 96%, 97%, 98%, 99% or more homology to the wild-type allele. Generally, the mutant allele will be obtained from diseased tissues or cells and is associated with a disease state.

As used herein the term 'melting temperature' or 'Tm' refers to the temperature at which a polynucleotide dissociates from its complementary sequence. Generally, the Tm may be defined as the temperature at which one-half of the Watson-Crick base pairs in a duplex nucleic acid molecule are broken or dissociated (i.e., are 'melted') while the other half of the Watson-Crick base pairs remain intact in a double stranded conformation. In other words, the Tm is defined as the temperature at which 50% of the nucleotides of two complementary sequences are annealed (double strands) and 50% of the nucleotides are denatured (single strands). Tm, therefore defines a midpoint in the transition from double-stranded to single-stranded nucleic acid molecules (or, conversely, in the transition from single-stranded to double-stranded nucleic acid molecules).

The Tm can be estimated by a number of methods, for example by a nearest-neighbor calculation as per Wetmur 1991 (Wetmur, J. G. 1991. DNA probes: applications of the principles of nucleic acid hybridization. Crit. Rev Biochem Mol Biol 26: 227-259, hereby incorporated by reference) and by commercial programs including Oligo™ Primer Design and programs available on the internet. Alternatively, the Tm can be determined though actual experimentation. For example, double-stranded DNA binding or intercalating dyes, such as ethidium bromide or SYBR-green (Molecular Probes) can be used in a melting curve assay to determine the actual Tm of the nucleic acid. Additional methods for determining the Tm of a nucleic acid are well known in the art and described herein.

As used herein, the term 'critical denaturation temperature' or 'Tc' refers to a temperature below the Tm of the wild type sequence, at which temperature a duplex of the wild-type sequence and the mutant sequence will melt. (In some instances, this temperature may be one at which a homoduplex of the mutant sequences also melts.) The Tc is applied to preferentially denature the double-stranded sequences that contain mutations, while keeping in duplex form the wild-type sequences, so as to allow the selective enrichment of the sequence containing a mutation during an amplification reaction. The critical denaturing temperature (Tc) is the temperature below which PCR efficiency drops abruptly for a given nucleic acid sequence. For example, a 167 bp p53 homoduplex sequence amplifies well if the PCR denaturing temperature is set at 87° C., amplifies modestly at 86.5° C. and yields no detectable product if PCR denaturation is set at 86° C. or less. Therefore in this example Tc is 86.5° C. The Tc is about 0.1-20° C. below the Tm of the wild-type sequence (and/or reference sequence in certain examples herein). More preferably the Tc is about 0.1-10° C., 0.1-9° C., 0.1-8° C., 0.1-7° C., 0.1-6° C., 0.2° C.-5° C., 0.3° C.-4.5° C., 0.4-4° C., 0.5-3.5° C., 0.5-3° C., 0.5-3° C., 0.5-2.5° C., 0.5-2° C., 0.5-1.5° C., 0.5-1° C. below the Tm of the wild-type sequence. In some embodiments, the Tc is below the Tm of both the wild-type homoduplex and the mutant homoduplex target sequences. For example, the Tc may be about 0.1-10° C., 0.1-9° C., 0.1-8° C., 0.1-7° C., 0.1-6° C., 0.2-5° C., 0.3-4.5° C., 0.4-4° C., 0.5-3.5° C., 0.5-3° C., 0.5-3° C., 0.5-2.5° C., 0.5-2° C., 0.5-1.5° C., 0.5-1° C. below the Tm of both the wild-type homoduplex and the mutant homoduplex target sequences.

One approach to identify the optimal Tc to run a COLD-PCR reaction, is to run a wild-type sequence in a gradient covering several different denaturation temperatures. In parallel, a gradient of mutant sequences and/or heteroduplex mutant:wild-type sequences is run under the same conditions. Once a temperature is identified that enables reproducible generation of robust PCR product for the mutated sequences, but not for the wild-type sequences, this represents the optimal Tc that can be adopted thereafter for the particular region of interest.

In practice we find that in most cases the optimal Tc to run a reaction lies 1 degree below the Tm. Accordingly, an easier approach to identify the Tc of a sequence is to adopt the empirical rule Tc=Tm-1° C. for homoduplexes versus heteroduplexes, where there are only one or a few differences between the wild-type and the mutant sequences. Because there are established experimental methods to identify the Tm of a sequence (e.g. experimentally via melting curve analysis; or theoretically via software prediction), this approach for identifying the Tc is more practical. In most instances, the formula Tc=Tm-1° C. provides the optimal Tc. However, in some embodiments, the formula Tc=Tm-1° C. may not provide the most optimal value of Tc. In such cases the detailed 'gradient-based' method described herein can be used to identify the Tc.

As used herein, the term "critical hybridization temperature" (CHT) refers to the temperature (or range of temperatures) over which the rate of hybridization of a wild type DNA target strand with the (immobilized) wild type complementary strand is higher than the rate of hybridization of a mutant DNA target strand with the (immobilized) wild type complementary strand. When there is a single base pair difference between mutant target sequence and reference sequence, there is a reduction in hybridization efficiency relative to a wild type target sequence hybridizing to a fully matched reference sequence. Thus, at the critical hybridization temperature, there is selective formation of wild-type target sequence/reference sequence duplexes relative to formation of mutant sequence/reference sequence duplexes. The critical hybridization temperature is not the same as the critical denaturation temperature.

Unlike the critical denaturation temperature which generally has a narrow range (typically 0.5-2° C. below Tm), the critical hybridization temperature (CHT) has a broad range. Typically the critical hybridization temperature is several different temperatures below the Tm of the wild type strand, and allows differential hybridization of the mutant and wild type target sequences. In some embodiments, the critical hybridization temperature is 0-20° C. lower than Tm. In some embodiments, the critical hybridization temperature is 1-10° C., 2-8° C., or 3-6° C. lower than the Tm of the wild type strand.

As used herein, 'reaction mixture' is a mixture suspected of containing a mutant sequence duplex that comprises a suitable buffer for allowing the denaturing of a mutant sequence.

The mutant target sequences and wild type sequences are obtained from a biological sample, such as a resected tumor tissue, plasma, and blood. In some embodiments, obtaining mutant target sequences and wild type sequences from a sample involves isolating plasma-circulating DNA from a plasma sample obtained from an individual using the QIAamp MinElute virus spin kit. Obtaining mutant target sequences and wild type sequences from a sample may also involve isolating genomic DNA from the sample followed by fragmentation of the genomic DNA using physico-chemical means or enzyme-driven fragmentation.

As used herein, 'primer pair' refers to two primers that anneal to opposite strands of a mutant target and wild type sequence so as to form an amplification product during a PCR reaction. The primer pair is designed so as to have a Tm lower than the Tc of the reaction.

According to one aspect of the invention, a set of specially-designed primer pairs specific to regions of interest are provided. The primer pairs are designed using available computer programs such that upon amplification the resulting amplicons are predicted to have the same melting temperature (i.e., all resulting amplicons are iso-Tm or iso-Tc). A number of primer design software are available, and can be used to specially design primers, such as Primer3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386), Primer-Blast (NCBI tools), Primer Premier (Premier Biosoft International), and OligoPerfect™ Designer (Invitrogen). In some embodiments, primers are designed that upon amplification generate iso-Tm or iso-Tc DNA amplicons covering a set of genes shown to correlate with response to a specific drug treatment or a DNA repair pathway.

According to some aspects of the invention, a method for multiplexing COLD-PCR/ice-COLD-PCR to enrich simultaneously several low abundance alleles (mutant target sequences) from a sample is provided. The method involves capturing a reaction mixture suspected of having a mutant target sequence and a wild type sequence within a constrained space. As used herein, 'constrained space' includes, for example, droplets, micro-chambers, pico-litter volumes, emulsion, micro-beads, glass chambers, or alternative solid supports such as a glass-surface or a semiconductor surface. COLD-PCR/ice-COLD-PCR includes a cross-hybridization step, during which mutant sequences hybridize to wild-type sequences to form hetero-duplexed molecules that melt preferentially at a critical denaturation temperature that is below the melting temperature of the homo-duplex. Because proximity of DNA molecules increases the hybridization efficiency substantially, it is expected that performing COLD-PCR in space-constrained small volumes, (e.g. in Raindance™ technologies, FIG. 1, or as in Fluidigm technologies) or on solid support (beads, or in BEAM-ing technologies, glass, or on any other nano-platform) increases greatly the mutation enrichment potential. Therefore the methods described herein may be performed either by solution-based COLD-PCR or by space-constrained COLD-PCR to achieve more efficient and multiplexed mutation enrichment.

The mutant and wild type target sequences may be preferentially enriched prior to capturing the reaction mixture within a constrained space. For example, specially-designed biotinylated capture-oligonucleotides may be used to capture selected fractions from fragmented genomic DNA prior to capturing the reaction mixture within a constrained space. In some embodiments, specially designed molecular inversion probes may be used to capture selected fractions from fragmented genomic DNA prior to capturing the reaction mixture within a constrained space (see, e.g. http://world wide web.ncbi.nlm.nih.gov/projects/genome/probe/doc/TechMIP.shtml; Nilsson M et al. Padlock probes: circularizing oligonucleotides for localized DNA detection. Science. 1994 Sep. 30; 265(5181):2085-8). In some embodiments, specially designed microarray-based capture probes may be used to capture selected fractions from fragmented genomic DNA prior to capturing the reaction mixture within a constrained space (Chou et al. DNA sequence capture and enrichment by microarray followed by next-generation sequencing for targeted resquencing: neurofibromatosis type 1 gene as model. Clin. Chem. (2010) 56:1, 62-72). In some embodiments, long-range PCR to selectively amplify the mutant target sequence and the wild type sequence is performed prior to capturing the reaction mixture within a constrained space. In some embodiments, ligation-mediated-PCR of blunted DNA fragments of plasma circulating DNA is performed to preferentially amplify the smaller size apoptotic DNA fragments (FIG. 1B). This type of circulating-DNA amplification increases the proportion of DNA originating from a tumor (Mamon H, Hader C, Li J, et al. Preferential amplification of apoptotic DNA from plasma: potential for enhancing detection of minor DNA alterations in circulating DNA. Clin Chem 2008; 54(9):1582-4).

COLD-PCR/ice-COLD-PCR in Droplets

In some embodiments, the method is performed in droplets (e.g., droplet emulsions). The droplet emulsion may include discontinuous or dispersed regions of a subject fluid (e.g., droplets) in a continuous fluid, with these fluids optionally separated by one or more intermediate fluids. The subject fluid may include, for example, an aqueous solution containing one or more components of interest (e.g., target sequences, beads, fragmented DNA, dNTPs, primers, etc.), and the continuous fluid may be a fluid that is immiscible or slightly miscible with the subject fluid.

The reaction mixture along with PCR reagents is dispensed into droplets. Specially-designed primer pairs specific to the mutant target sequences and the wild type sequences which result in iso-Tm or iso-Tc DNA amplicons upon amplification are also dispensed into microdroplets. The droplets containing the fragmented DNA with PCR reagents are then merged with the droplets containing the specially-designed primers such that every microdroplet contains the reaction mixture, primer pair and PCR reagents. The method then includes subjecting the reaction mixture to conventional PCR using the specially designed primers to allow formation of iso-Tm DNA amplicons within all droplets. A typical conventional PCR thermal cycling protocol comprises 30 cycles of (a) denaturation at a range of 90° C. to 95° C., (b) annealing at a temperature ranging from 50° C. to 68° C., and (c) extension at 68° C. to 75° C. In some embodiments, the conventional PCR thermal cycling protocol comprises 5 cycles, 10 cycles, 15 cycles, 20 cycles, 25 cycles, 30 cycles or 35 cycles.

In some embodiments, instead of using specially-designed primer pairs and PCR amplification to generate iso-Tm or iso-Tc DNA amplicons, anchor oligonucleotides are used. The anchor oligos are designed such that the resulting DNA strands following extension and ligation are iso-Tm or iso-Tc and wherein all the amplicons can be amplified using common primers. Each anchor oligonucleotide comprises a portion that recognises and binds to the target nucleic acid and a portion that does not bind the target (a non-binding tail). All the forward primers have a tail with a common sequence and all the reverse primers have a tail with a common sequence. Upon merging the droplets containing the reaction mixture with droplets containing the anchor oligonucleotides, the anchor oligonucleotides hybridize to the mutant and wild type target sequences. This is followed by primer extension using dNTPs and Taq DNA polymerase and ligation using DNA ligase. The result is iso-Tm or iso-Tc amplicons with common ends formed of the primer tails. The common primer tails enable subsequent COLD amplification of all target DNA sequences in a single reaction, using only a single set of primers which cause the amplification of all the different amplicons.

Next, the method involves performing separate COLD-PCR reactions on millions of droplets in parallel to enrich mutation containing sequences. COLD-PCR reactions can be performed according to the methods described in detail in International Publication No. WO 2009/017784, which is incorporated herein by reference in its entirety for all purposes. Briefly, COLD-PCR is performed as follows:

(i) subjecting the amplified reaction mixture to a first denaturing temperature that is above the melting temperature (Tm) of the amplified wild type sequence so as to permit the denaturation of said mutant sequence and said wild type sequence, wherein said mutant sequence is at least 50% homologous to said wild type sequence and is amplifiable by the same primer pair as said wild type sequence. The first denaturing temperature is set according to standard procedures used in PCR. Thus, the first denaturing temperature should be sufficiently high so as to allow the full denaturation of the mutant and wild type sequences (e.g., 96° C.). In one embodiment, the first denaturing temperature is about 1° C. to 30° C. above the Tm of the wild type sequence, more preferably the first denaturing temperature is about 5° C. to 20° C. above the Tm of the wild type sequence.

(ii) reducing the temperature of the amplification reaction mixture so as to permit formation of a mutant strand/wild type strand duplex. In a preferred embodiment, this hybridization temperature or intermediate temperature (the temperature being below the first denaturing temperature and Tc but above the primer annealing/extension temperature, e.g., about 600 C to 800 C) is above the Tm, of the primer pair, and thus allows the mutant and wild type sequences to hybridize while preventing binding of the primer pair to the mutant and/or wild type sequences. This annealing step results in the formation of hybridization duplexes of double stranded mutant-mutant, wild type-wild type and mutant-wild type sequences.

(iii) subjecting the amplified reaction mixture to a critical denaturation temperature (Tc) that is below the Tm of said wild type sequence so as to permit the preferential denaturation of said duplex of step (ii) to form denatured mutant and wild type strands. The Tc or critical denaturation temperature is below the Tm of the wild type sequence and can be determined by the methods described herein. In one embodiment, the Tc is about 0.3° C.-5° C. below and more preferably about 0.5° C. to 1.5° C. below the Tm of the wild type sequence. Generally, the Tc will be about 70-90° C. The mutant-mutant hybridization duplexes may also be preferentially denatured if the mutant sequence has a nucleotide sequence which results in a lower Tm compared to the wild type sequence. At the Tc, the mutant-wild type sequence duplexes (and mutant-mutant sequence duplexes only if having a lower Tm, than the wild type sequence) are substantially denatured, whereas the mutant-mutant duplexes (if having a Tm equal to or greater than the Tm, of the wild type sequence) and the wild type-wild type sequence duplexes are substantially un-denatured. "Substantially" means at least 60%, preferably at least 70%, more preferably at least 80%, even more preferably at least 90% and most preferably at least 98% in a given denatured or un-denatured form. The Tc is generally applied from about 1 second to 5 minutes, more preferably 2 seconds to 1 minute and most preferably 5 seconds to 30 seconds.

(iv) reducing the temperature of the reaction mixture so as to permit said primer pair to anneal to said mutant and wild type strands, and (v) extending said primer pair so as to enrich said mutant sequence relative to said wild type sequence.

The steps of the method are generally repeated for multiple cycles in order to get sufficient amplification of the mutant and wild type sequences. In one embodiment, the steps of the method are repeated for 5-40 cycles and more preferably 10-30 cycles. The optimal number of cycles can be determined by one of ordinary skill in the art.

Even though much of the description herein includes performing methods involving droplets, it should be understood that the methods can be used in the context of other isolated regions of fluids. For example, in some embodiments, isolated regions of fluid may be in the form of subject fluids positioned in one or more wells or reservoirs (e.g., micro-, nano-, or pico-liter sized wells or reservoirs). Thus, where the description herein concerns "droplets", the description may equally apply to other isolated regions of fluids (e.g., fluids in "wells"). In some cases, the subject fluids, while positioned in one or more wells or reservoirs, are not surrounded by an immiscible or slightly miscible fluid. In other cases, subject fluids in the form of droplets can be combined with a well or reservoir system such that the droplets are positioned in the wells or reservoirs during use. Other configurations of isolated regions of fluid are also possible. Additionally, methods involving isolated (e.g., space constrained) components of interest that do not necessarily involve the use of isolated regions of fluids are also possible. For example, in some embodiments, methods described herein can be performed on solid supports (e.g., on glass, beads, or other supports).

Fluids

With respect to a discontinuous or dispersed region of a subject fluid (e.g., a droplet) in a continuous fluid, these fluids can be selected among essentially any fluids (liquids, gases, and the like) by those of ordinary skill in the art by considering the relationship between the fluids. For example, the subject fluid and the continuous fluid may be selected to be immiscible or slightly miscible within the time frame of formation of the dispersed portions. Where the dispersed portions remain liquid for a significant period of time, the fluids may be significantly immiscible. In other cases, the fluids need not be as immiscible (e.g., they may be slightly miscible). Those of ordinary skill in the art can select suitable immiscible or slightly miscible fluids, using contact angle measurements or the like, to carry out the methods described herein.

Various types of fluids may be used in the embodiments described herein. Typically, a subject fluid containing one or more components of interest (e.g., nucleic acids, dNTPs, primers, etc.) is aqueous, although non-aqueous fluids can be used as subject fluids in certain embodiments. If the subject fluid is in the form of a droplet in a continuous fluid, the continuous fluid may be immiscible or slightly miscible with the subject fluid. Non-limiting examples of suitable continuous fluids include oils (e.g., silicone oil, mineral oil), fluorocarbons, hydrocarbons, and non-polar solvents. Sometimes, a continuous fluid, which may be immiscible with the aqueous fluid defining the droplet, is slightly water soluble. For example, oils such as poly(dimethylsiloxane) (PDMS) and poly(trifluoropropylmethysiloxane) are slightly water soluble. Gases such as air may also be used as continuous fluids.

Droplets

Droplets of varying volumes and sizes may be used in the embodiments described herein. In some cases, a method may involve the use of a plurality of droplets having the same or substantially same volume. In other cases, it may be suitable to generate a plurality of droplets having different volumes for use in a method described herein. Volumes of droplets may be chosen depending on the particular application. Generally, a droplet may have a volume between 10 μL and 1 μL, although other volumes are also possible. In certain embodiments, droplets may have volumes of, for example, less than 1 μL, less than 0.1 μL, less than 10 nL, less than 1 nL, less than 0.1 nL, or less than 10 μL. In other embodiments, droplets may have volumes of, for example, greater than 10 μL, greater than 0.1 nL, greater than 1 nL, greater than 10 nL, greater than 0.1 μL, or greater than 1.0 μL. Other ranges of droplet volumes are also possible.

Generally, a droplet may have a size between 0.1 μm and 1,000 μm, although other sizes are also possible. In some embodiments, a droplet has a largest cross-sectional dimension (e.g., a diameter) of, for example, less than 1,000 μm, less than 750 μm, less than 500 μm, less than 100 μm, less than 75 μm, less than 50 μm, less than 25 μm, less than 10 μm, less than 5 μm, less than 1 μm, or less than 0.1 μm. In other embodiments, a droplet has a largest cross-sectional dimension (e.g., a diameter) of, for example, greater than 0.1 μm, greater than 1 μm, greater than 5 μm, greater than 10 μm, greater than 25 μm, greater than 50 μm, greater than 75 μm, greater than 100 μm, greater than 500 μm, greater than 750 μm, or greater than 1,000 μm. Other sizes are also possible.

In some embodiments, a plurality of droplets is substantially monodisperse in size. A plurality of droplets may have a polydispersity of, for example, less than 5%, less than 4%, less than 3%, less than 2%, less than 1.5%, or less than 1%. In other embodiments, the sizes of a plurality of droplets can vary and the droplets are not substantially monodisperse.

The droplets are typically spherical in shape, but may be non-spherical depending on the droplet's surrounding environment. For example, a droplet placed in a well or a channel may take on the shape of the well or channel in some embodiments.

Droplet Formation

The droplets described herein can be formed using any suitable technique. In some embodiments, the droplets are formed by a flow focusing technique. Flow focusing may involve focusing the flow of a subject fluid by exposing the subject fluid to two separate streams of a continuous fluid, and allowing the two separate streams to join and to completely circumferentially surround the subject fluid stream to form a droplet of the subject fluid. In some cases, droplets are formed by flowing a subject fluid through a nozzle. The subject fluid may protrude from the nozzle, and the protrusion may grow as additional subject fluid is injected. Simultaneously, a continuous fluid may be injected to shear the outer surface of the protruding subject fluid, as they are focused into a channel. When the shear on the subject fluid due to the continuous fluid exceeds the surface tension holding the subject fluid protrusion at the nozzle, a droplet of subject fluid is pinched off and dispersed into the continuous fluid. This process repeats and may form droplets of the same size, or of different sizes, depending on the desired mono- or polydispersity of the droplets. Non-limiting examples of methods for forming droplets are described in more detail in U.S. Pat. No. 7,708,949, filed Dec. 28, 2004, entitled "Method and Apparatus for Fluid Dispersion" [Harvard]; International Publication No. WO/2009/139898, filed May 15, 2009, entitled "Valves and Other Flow Control in Fluidic Systems Including Microfluidic Systems" [Harvard]; and U.S. Pat. No. 6,951,632, filed Nov. 16, 2001, entitled "Microfluidic Devices for Introducing and Dispensing Fluids from Microfluidic Systems", each of which is incorporated herein by reference in its entirety for all purposes.

Components of Interest

As described herein, an isolated region of fluid (e.g., a droplet or a fluid in a well) may contain various components of interest. In some embodiments, the components of interest are specific to performing PCR. In some such embodiments, the components of interest are specific to a particular process, such as a COLD-PCR or an ice-COLD-PCR process as described herein.

Certain methods described herein involve the use of a library of different components of interest, such as a library of primer pairs specific to regions of interest which result in iso-Tm or iso-Tc DNA fragments upon amplification, or a library of beads comprising different specific capture sequences. In some embodiments, different members of the library (e.g., primer pairs, or beads) may be dispensed into the droplets such that each droplet contains one or more different library members. Each droplet may contain various numbers of copies of a component of interest, as described herein. Multiple droplets can form a droplet library of the components. For example, in one set of embodiments, each droplet contains one primer pair specific to a region of interest which results in a DNA fragment that is substantially iso-Tm (and substantially iso-Tc) with respect to other DNA fragments (contained in other droplets) upon amplification. A plurality of such droplets may form a droplet library of specially-designed primer pairs that result in substantially iso-Tm (and substantially iso-Tc) DNA fragments upon amplification. In another set of embodiments, each droplet contains at least one bead having attached thereto a specific capture sequence. Additionally, each droplet may optionally contain a primer pair, one or more components of which may be attached to the bead or in solution. A plurality of such droplets may form a droplet library of beads with specific capture sequences (optionally with the primer pair). Other examples of libraries of components are provided herein. Each droplet may optionally contain other components of interest (e.g., dNTPs, enzymes, buffer components) that may be generic to the other droplets, and are used for amplification.

In some embodiments, a plurality of droplets is provided, each of the droplets including fragmented DNA of different regions of interest. The region of interest in the droplet may be optionally enriched. In some cases, the regions of interest are enriched prior to being included in the droplets. In other cases, the regions of interest are enriched after being in droplet form. In one set of embodiments, a plurality of droplets is provided, each of the droplets including specially-designed biotinylated capture-oligonucleotides which may be used to capture selected fractions from fragmented genomic DNA. In another set of embodiments, a plurality of droplets is provided, each of the droplets including specially designed molecular inversion probes which may be used to capture selected fractions from fragmented genomic DNA. In another set of embodiments, a plurality of droplets is provided, each of the droplets including specially designed microarray-based capture probes which may be used to capture selected fractions from fragmented genomic DNA. In yet another set of embodiments, a plurality of droplets is provided, each of the droplets including amplified regions of interest (e.g., formed by using long-range PCR). In some embodiments, ligation-mediated-PCR of blunted DNA fragments of plasma circulating DNA is performed to preferentially amplify smaller size apoptotic DNA fragments, and such fragments are included in a plurality of droplets. In yet another set of embodiments, a plurality of droplets is provided, each of the droplets including anchor oligonucleotides. As described herein, the anchor oligonucleotides may be designed such that the resulting DNA strands following extension and ligation are iso-Tm or iso-Tc.

Various numbers of copies of a component of interest may be provided in each droplet. For example, in some embodiments, each droplet of a plurality of droplets (e.g., a droplet library) includes a single copy of a component of interest. In other embodiments, each droplet of a plurality of droplets includes 2-5,000 copies of a component of interest (e.g., greater than 2 copies, greater than 10 copies, greater than 50 copies, greater than 100 copies, greater than 200 copies, greater than 500 copies greater than 700 copies, greater than 1,000 copies, greater than 2,000 copies, or greater than 4,000 copies of a component of interest). The component of interest may be those described herein (e.g., DNA fragments, primer pairs, etc.). In some embodiments, each droplet contains on average ~2-1000 genome copies to enable formation of heteroduplexes during COLD-PCR cycling. Other numbers of copies of components of interest are also possible.

In some embodiments a plurality of droplets containing different components of interest (e.g., a droplet library) is provided, the plurality of droplets comprising greater than 2 droplets, greater than 10 droplets, greater than 100 droplets, greater than 500 droplets, greater than 1,000 droplets, greater than 5,000 droplets, greater than 10,000 droplets, greater than 50,000, greater than 100,000, greater than 500,000, or greater than 1,000,000 droplets. As described in more detail herein, a plurality of droplets containing components of interest can be manipulated substantially simultaneously to perform a plurality of reactions in parallel. In certain embodiments, greater than 2 droplets, greater than 10 droplets, greater than 100 droplets, greater than 500 droplets, greater than 1,000 droplets, greater than 5,000 droplets, greater than 10,000 droplets, greater than 50,000, greater than 100,000, greater than 500,000, greater than 1,000,000 droplets can be manipulated substantially simultaneously to perform a plurality of reactions in parallel.

A plurality of droplets containing different components of interest (e.g., a droplet library) may be formed by any suitable method. In some embodiments, a method of forming droplets containing different components of interest involves providing a subject fluid containing the components of interest (e.g., fragmented DNA and reagents for PCR, beads, etc.), and using a flow focusing technique or any other suitable technique to form the droplets. The number of components of interest in each droplet can be controlled by, for example, varying the concentration of the components in the subject fluid prior to droplet formation, by varying the flow rate of the subject fluid and continuous fluid during droplet formation, and/or by using other methods known to those of ordinary skill in the art. Non-limiting examples of methods for producing droplet libraries are described in more detail in U.S. Publication No. 2010/00022414, filed Jul. 17, 2009, entitled "Droplet Libraries" [Raindance™], which is incorporated herein by reference in its entirety for all purposes.

Methods for Merging Droplets

In some embodiments, a droplet of a first type (e.g., a droplet containing a first reagent, which may optionally be a member of a first droplet library) is combined with a droplet of a second type (e.g., a droplet containing a second reagent, which may optionally be a member of a second droplet library). For example, a droplet of a first type may include a first set of components for performing PCR (e.g., COLD-PCR or ice-COLD-PCR, such as fragmented DNA, dNTPs, enzymes such as polymerase and/or buffer components, and a droplet of a second type may include a second set of components for performing PCR (e.g., COLD-PCR or ice-COLD-PCR, such as primers for specific regions). The combined droplet may contain DNA fragments, a specific primer pair and PCR reagents in amounts suitable for a full amplification or enrichment. Optionally, three or more droplets (e.g., droplet containing components for performing PCR) may be combined to form a single droplet in some embodiments. Merging (i.e., fusing) of droplets can be performed by any suitable method. In some embodiments, merging of droplets is performed using an electric field. For example, two streams of droplets in a microfluidic system may combine at an intersection (e.g., in a "Y" configuration) or other suitable configuration, and electrodes that can produce an electric field at or near the intersection may be used to reduce the surface tension of the two droplets. Reduction of the surface tension of the droplets can allow the droplets to merge when the droplets are brought in close proximity to one another. In another embodiment, a heating element can be used to merge droplets. In other embodiments, merging of droplets can be performed by draining the continuous fluid between the two droplets and bringing the two droplets close together. For example, for a device that is fabricated in a polymer such as PDMS, an oil separating the droplets may dissolve into the bulk of the polymer device over time. This can cause the droplets to merge in certain embodiments (e.g., if the droplets or the continuous fluid do not include a surfactant, the droplets are more likely to merge).

In some embodiments, additional regents can be introduced into droplets without the merging of droplets. For instance, a droplet including a fluid of a first type (e.g., a droplet containing a first reagent, which may optionally be a member of a first droplet library) may be combined with a stream of fluid of a second type (e.g., a fluid containing a second reagent).

Other methods for merging droplets or introducing reagents into droplets can also be used. Non-limiting examples of methods for merging droplets and introducing reagents into droplets are described in International Publication No. WO/2007/133710, filed May 11, 2007, entitled "Microfluidic Devices and Methods of Use Thereof" [Raindance™], and Teh et al., "Droplet microfluidics", Lab Chip, 2008, 8, 198-220, each of which is incorporated herein by reference in its entirety for all purposes.

Additives

A variety of different additives can be included in the droplets described herein. In some embodiments, one or more surfactants or detergents may be added to the droplets, and/or to a continuous fluid surrounding the droplets, to stabilize the droplets against coalescence. The type of surfactant chosen may depend on factors such as the type of continuous fluid being used, the contents inside the droplet, and the material containing the emulsion. For example, if the emulsion is contained in a microfluidic device fabricated in a certain material, the surfactant may be chosen such that it stabilizes an aqueous droplet, does not denature the contents inside the droplet, and is compatible with a carrier fluid that does not dissolve in the material used to form the device. Any suitable surfactant, including anionic, non-ionic, or cationic surfactants, may be used. In one set of embodiments, suitable surfactants may include the non-ionic surfactants sorbitan-based carboxylic acid esters ("Span"), including sorbitan monolaurate (Span 20), sorbitan monopalmitate (Span 40), sorbitan monostearate (Span 60) and sorbitan monooleate (Span 80), and perfhiorinated polyethers. Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used.

In some embodiments, the droplets include one or more labels. For example, a single droplet may contain a single label in some instances. The label may be attached to an entity inside the droplet such as a chemical or biological material (e.g., fragmented DNA, a primer, a capture sequence) or a non-chemical or biological material (e.g., a bead). In other embodiments, the label is free-floating in the droplet. Any suitable label may be used. Non-limiting examples of labels include optical labels, enzymatic labels and radioactive labels, including but limited to proteins, DNA tags, dyes, quantum dots, radio frequency identification tags, or combinations thereof. The label may be detected by any suitable method such as by fluorescence polarization, fluorescence intensity, fluorescence lifetime, fluorescence energy transfer, pH, ionic content, temperature or combinations thereof.

Wells

In some embodiments, one or more isolated regions of fluid are positioned in one or more wells (e.g., micro-, nano-, or pico-liter sized wells) or reservoirs. As described herein, the isolated regions of fluids may be in the form of droplets, or simply isolated fluids inside the wells. The wells may be configured as a micro-, nano-, or pico-titer plate, positioned in a microfluidic system, or have any other suitable configuration.

A device (e.g., a titer plate, or a microfluidic device) can include any suitable number of wells. For instance, a device can include greater than 1, great than 5, greater than 10, greater than 100, greater than 1,000, greater than 10,000, greater than 50,000, greater than 100,000, greater than 500,000, or greater than 1,000,000 wells that may be used to hold a fluid (e.g., a droplet or other isolated fluid).

The wells may have any suitable size, volume, shape, and/or configuration. For example, a well may have at least one cross-sectional dimension (e.g., a length, width or height) of less than 250 µm, less than 200 µm, less than 150 µm, less than 100 µm, less than 75 µm, less than 50 µm, less than 25 µm, less than 10 µm, or less than 1 µm. In some embodiments, a well can have a volume of less than 50 µL, less than 10 µL, less than 1 µL, less than 100 nL, less than 10 nL, less than 1 nL, less than 100 pL, or less than 10 pL. Other sizes and volumes are also possible.

A well can have any suitable shape for holding a fluid. For example, one well may have a cross-section in the shape of a square, another may be rectangular, and another may have a triangular shape. If the wells are used to contain droplets, different shapes of wells may allow droplets to have different surface energies while positioned in the well, and can cause a droplet to favor one shape over another. Different shapes of microwells can also be used in combination with droplets of different size, such that droplets of certain sizes favor particular shapes of microwells.

In some cases, the size of the well is approximately the same size as the droplet. For instance, the volume of the well can be less than approximately twice the volume of the droplet. This is particularly useful for positioning a single droplet within a single well. In other cases, however, more than one droplet can be positioned in a well. Having more than one droplet in a well can be useful for applications that require the merging of two droplets into one larger droplet, and for applications that include allowing a component to pass (e.g., diffuse) from one droplet to another adjacent droplet. Non-limiting examples of methods for positioning droplets in wells are provided in U.S. Pat. No. 7,556,776, filed Sep. 8, 2005, entitled "Microfluidic Manipulation of Fluids and Reactions" [Brandeis/Harvard]; U.S. Publication No. 2010/0163109, filed Aug. 4, 2009, entitled "Manipulation of Fluids and Reactions in Microfluidic Systems" [Brandeis/Harvard], each of which is incorporated herein by reference in its entirety for all purposes.

It should be understood, however, that in other embodiments, droplets need not be positioned in wells of a microfluidic device. For example, droplets can be aligned side by side one another in a channel or a reservoir of a microfluidic system, each of the droplets separated by a continuous fluid. In another example, a plurality of droplets are positioned (e.g., randomly) in a large reservoir of a microfluidic device. Other configurations are also possible.

Microfluidic Channels

Droplets or other isolated regions of fluid may be positioned in regions of a microfluidic device having any suitable cross-sectional dimension. Typically, fluid channels in a microfluidic system have maximum cross-sectional dimensions of less than 2 mm, and in some cases, less than 1 mm. In some embodiments, all fluid channels of a device have a largest cross sectional dimension of no more than 2 mm or 1 mm. However, larger regions such as reservoirs having a largest cross-sectional dimension of, for example, between 2 mm and 50 mm, may be used to contain droplets or other entities. In one set of embodiments, the maximum cross-sectional dimension of the channel(s) of a microfluidic device are less than 500 microns, less than 200 microns, less than 100 microns, less than 50 microns, or less than 25 microns. The channel can have any suitable cross-sectional shape (circular, oval, triangular, irregular, square or rectangular, or the like), any suitable configuration (e.g., serpentine, straight), and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channels of the device may be hydrophilic or hydrophobic in order to minimize the surface free energy at the interface between a material that flows within the channel and the walls of the channel. For instance, if the formation of aqueous droplets in an oil is desired, the walls of the channel may be made hydrophobic. If the formation of oil droplets in an aqueous fluid is desired, the walls of the channels may be made hydrophilic. Other configurations are also possible.

Methods Involving Microfluidics

As described herein, certain aspects of the invention are directed to methods for enriching simultaneously several low abundance alleles (target sequences) from a sample via COLD-PCR or ice-COLD-PCR. In some cases, the target sequences are mutations at the 1-10% level. A method may involve, for example, introducing a first subject fluid in a dispersed phase in a first channel of a microfluidic device, and introducing a continuous phase fluid in a second channel of the device. The device may include components such as heating and cooling regions for performing PCR. The first subject fluid may include one or more target sequences to be enriched and optionally other components for performing COLD-PCR or ice-COLD-PCR (e.g., dNTPs, enzymes such as polymerase and/or buffer components). The channels of the microfluidic device may be configured to form droplets of the subject fluid (e.g., a first set of droplets); for instance, the channels may be arranged in a flow focusing configuration to allow droplet formation. The method may involve forming a plurality of droplets of the subject fluid (each of the droplets containing fragments of the target sequence to be enriched), the droplets optionally being monodisperse. In some embodiments, the method may involve introducing a second subject fluid containing a second set of components for performing PCR (e.g., primers for specific regions) into the device. The second subject fluid may also be formed into droplets (e.g., a second set of droplets) in some embodiments. In some instances, a droplet from the first set is merged with a droplet from the second set to form combined droplets, each of which contain all of the reagents necessary for performing COLD-PCR or ice-COLD-PCR. The method may involve performing COLD-PCR or ice-COLD-PCR on the plurality of (combined) droplets simultaneously in the microfluidic device to allow simultaneous enrichment of several low abundance alleles (mutant sequences) from the sample.

As a result of performing one or more methods described herein, in some embodiments, a plurality of droplets may be provided, each of the droplets containing enriched fragments of target sequences, wherein the target sequences comprise mutations at the 1-10% level.

The massively parallel COLD-PCR amplification in droplets can be performed by utilizing a micro-fluidic device from RainDance™ Inc. that can dispense DNA and PCR reagents within individual droplets prior to performing amplification on million of droplets in parallel to enrich mutation-containing sequences. To combine COLD-PCR with RainDance™ technology, the following modifications on the existing Raindance™ technology can be applied:

(a) the amount of input DNA can be adjusted so that each nano-droplet contains at average of ~2-1000 genome copies (instead of an average of 1 genome copy currently applied). In this manner, the formation of heteroduplexes during COLD-PCR cycling will be enabled.

(b) Because RainDance™ amplifies genomic DNA regions with a 10-fold variance from droplet-to-droplet, the total number of droplets formed per experiment can be increased by 5-10-fold. This amounts to increasing the total input DNA used and the total time of droplet formation, e.g. from the current 6-10 minutes to ~60 minutes. In this manner, the probability of capturing low-level events (mutations) in droplets will not be affected by inter-droplet variability, while in the subsequent COLD-PCR step the mutations will be enriched.

COLD-PCR/ice-COLD-PCR on Solid Support

In some embodiments, the method is performed on a solid support. For example, the reaction mixture is captured on magnetic beads. This could be achieved by hybridizing the DNA fragments with biotinylated capture oligos followed by incubating the oligo-DNA hybrids with steptavidin-coated magnetic beads. The beads are then washed to remove unbound DNA. Alternatively, a reference sequence (RS) is attached to a magnetic microbead by steptavidin-biotin binding. The RS is then used to capture the reaction mixture by incubating the RS-bound beads with the reaction mixture. Following incubation and washing, each bead contains several copies of mutant sequences and wild type sequences hybridized to bead-bound RS.

Each bead is then encompassed within an emulsion that contains single bead with captured mutant and wild type sequences and sequence-specific reverse primer bound to it plus common forward primer and PCR mix in solution within emulsion. Conventional PCR is then performed to allow formation of iso-Tm DNA fragments, followed by COLD-PCR reactions within emulsion. In some embodiments, both primers may be common to all target sequences following ligation of common 'tails' to the target sequences, and both primers may be bound to the bead.

In some embodiments, several individual conventional PCR reactions are performed in solution using biotinylated primers with common primer tails. The primer pairs are designed such that all resulting amplicons are iso-Tm (i.e., upon amplification, the resulting amplicons have the same melting temperature) or iso-Tc. Each PCR product (iso-Tm amplicon or iso-Tc amplicon) is then incubated with steptavidin-coated magnetic beads. The unbound DNA is removed by washing. This results in several copies of target sequences bound to the surface of the bead (i.e. several groups of ice-COLD-PCR beads with targets bounds to their surface are obtained). All groups of beads are then mixed in a single tube. Each bead is then encompassed within an emulsion so that at most a single bead is enclosed within each emulsion together with PCR components. Using the common primers, COLD-PCR is then performed on all beads simultaneously as described herein.

COLD-PCR/ice-COLD-PCR Bead Compositions

According to some aspects of the invention, a composition comprising streptavidin-coated magnetic microbeads having primer pairs attached to the bead surface are provided. The beads may be 1-3 μm in size. One or both primers specific for the mutant and wild type sequences can be bound to the bead surface. In some embodiments, a sequence-specific primer is attached to the bead, while the common primer is added to the emulsion during amplification. In some embodiments, specially-designed primers that upon amplification result in iso-Tm or iso-Tc DNA amplicons are bound to the bead surface.

According to some aspects of the invention, streptavidin-coated magnetic beads having a reference sequence (RS) bound to the bead surface are provided. The reference sequence is specific for the intended DNA target, and may be bound to the bead via a biotinylated nucleotide. Preferably the RS contains a 3'-end di-deoxy-nucleotide with a double biotin held by a carbon-chain spacer. Thus, the RS is 3'-blocked from polymerase extension, and designed according to the methods described in Milbury C A, et al. (Ice-COLD-PCR enables rapid amplification and robust enrichment for low-abundance unknown DNA mutations. Nucleic Acids Res; 39:e2).

The RS can be synthesized by standard oligonucleotide synthesizers. This mode of synthesis has the added advantage that modified nucleotides such as peptide nucleic acid (PNA) or locked nucleic acid (LNA) or uracil (U) can be inserted at will at any position desired on the RS sequence. Use of PNA at position of the sequence where 'hot-spot' mutations are known to concentrate in clinical cancer samples may boost the ability to enrich these particular mutations. Alternatively, RS can be synthesized via PCR reaction of the appropriate sequence from a wild-type DNA sample. PCR can be conducted with a 5'-biotinylated primer if immobilization to the beads from the 5'-end of the RS is desired. Following PCR, the 3'-end of the synthesized amplicon is blocked from polymerase extension, e.g. by adding a di-deoxy-nucleotide (ddNTP) which prevents further extension. Optionally, the ddNTP is also biotinylated or doubly-biotinylated when it is desirable to enable binding of the synthesized RS to the streptavidin beads from the 3'-end. Another yet way to block the 3'-end is via a —PO4 group, via a C-3 group at the 3'-end of the sequence, or via any other method known to skilled artisans of oligonucleotide synthesis and nucleic acid biochemistry.

Figure 2:
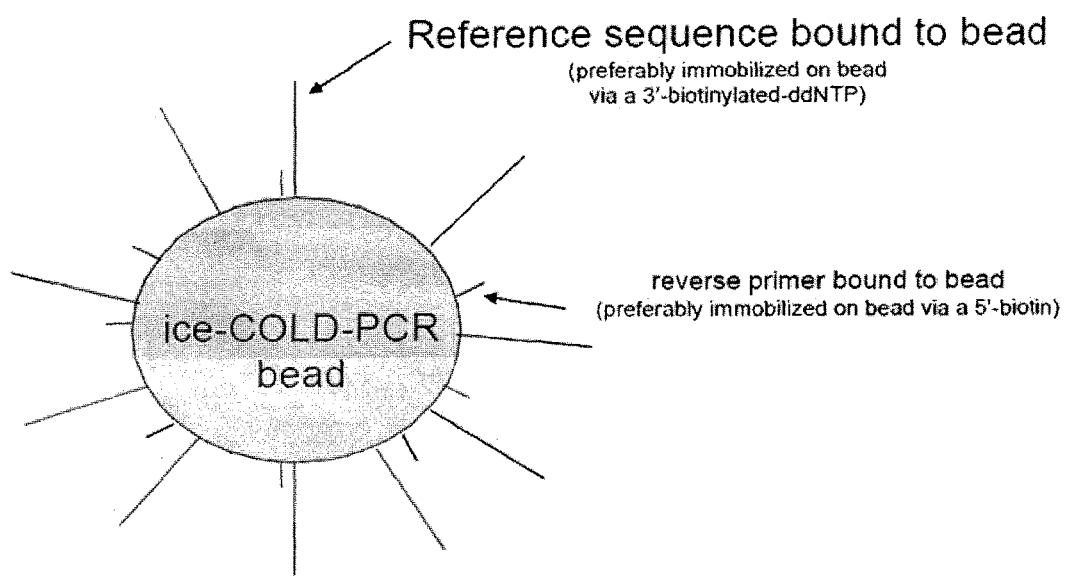
FIG. 2 shows the design of ice-COLD-PCR solid support (bead).

RS is complementary to the wild-type DNA target sequence, but 5-20 bp shorter in length so that it does not allow primer binding either to the RS or to the double stranded structure consisting of RS plus a target sequence hybridized to the RS. In some embodiments, the bead also contains on its surface one 5'-biotinylated, bound primer (e.g. a reverse primer) corresponding to one end of the intended DNA target (FIG. 2). The primer has only partial overlap with the RS, and can be designed per the methods described in Milbury C A, et al. (Ice-COLD-PCR enables rapid amplification and robust enrichment for low-abundance unknown DNA mutations. Nucleic Acids Res; 39:e2). The relative amounts of primer-to-RS bound to the surface can be varied, but preferably are in the region of 0.01-100 primer-to-RS ratio; or 0.1-10; or 0.5-2.0. In another embodiment of the invention, a pair of nucleic acid primers corresponding to the ends of the intended DNA target are bound to the ice-COLD-PCR bead.

The RS-bound beads described herein perform several functions:

(i) The beads enable sequence-specific capturing and hybridization of target sequences to the corresponding RS on the bead surface when incubated with genomic DNA fragments at an appropriate temperature, e.g. 60-70° C. Following repeated washing of the magnetic beads, each RS-bound bead contains only the target sequences complementary to the capture sequence bound to it. These sequences can be either wild type or mutant sequences, since at hybridization temperatures of 60-70° C. there is little discrimination between wild type and single point mutation-containing target sequences, and both are expected to bind to the RS. Thus, each bead can capture numerous target sequences including both wild type and mutant sequences on its surface, all of which hybridize to the bead-bound RS. In this manner, hundreds or thousands of diverse target sequences can be hybridized simultaneously with their respective RS on the bead surface, hence each RS serves as a 'magnet' for its own complementary target sequence.

Figure 3:
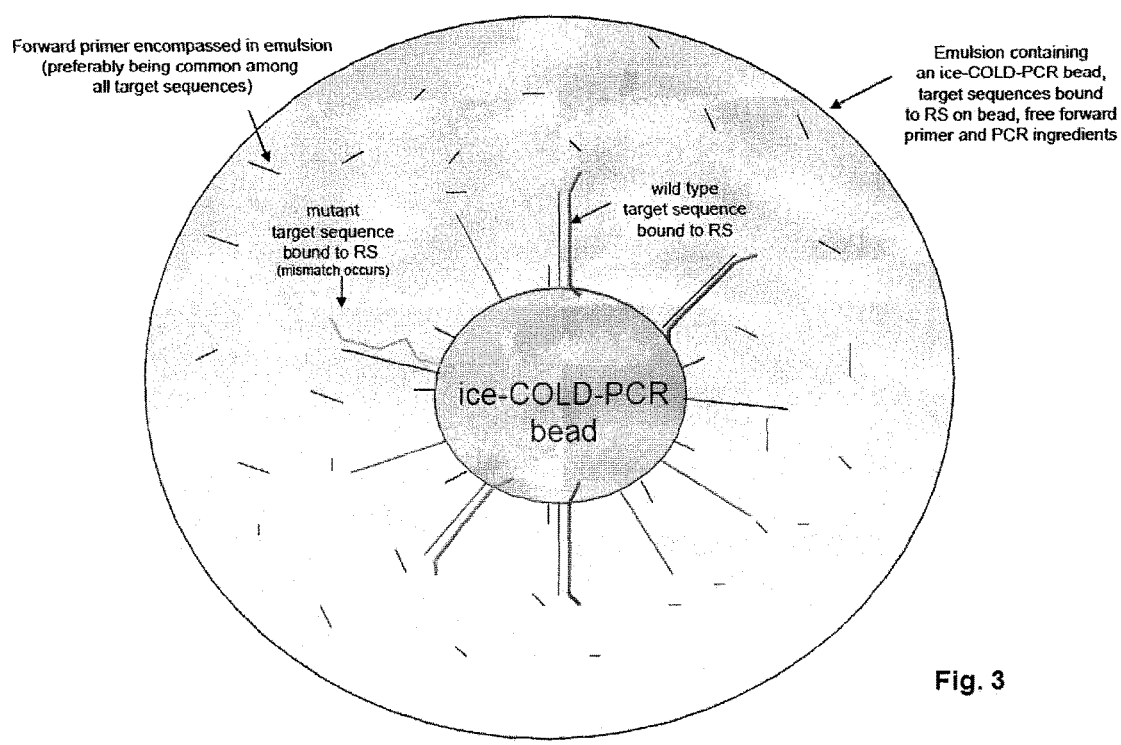
FIG. 3 shows an emulsion containing ice-COLD-PCR bead, captured target sequences, free forward primer and PCR ingredients (polymerase, dNTP, etc.) before ice-COLD-PCR amplification.

(ii) The beads enable performing the subsequent COLD-PCR in emulsion. In some embodiments, following incubation of the RS-bound beads with target sequences and capturing of each group of target sequences on the corresponding bead-bound RS, a forward (common to all target sequences) primer and PCR components are added to the bead solution and the beads are encompassed in emulsion, according to the general protocols described in Diehl F, Li M, He Y, et al. BEAMing: single-molecule PCR on microparticles in water-in-oil emulsions. Nat Methods 2006; 3(7):551-9; Li M, Diehl F, Dressman D, et al. BEAMing up for detection and quantification of rare sequence variants. Nat Methods 2006; 3(2):95-7; and Dressman D, Yan H, Traverso G, et al. Transforming single DNA molecules into fluorescent magnetic particles for detection and enumeration of genetic variations. Proc Natl Acad Sci USA 2003; 100 (15):8817-22. Each emulsion encompasses a RS-bound bead. Following this, the beads contain several copies of captured mutant and wild type sequences, as well as reverse primer bound to their surface, and forward primer in solution within emulsion (FIG. 3). During the subsequent COLD-PCR amplification, captured target sequences that are wild type remain bound to RS; while captured mutant sequences become denatured at the correct Tc and become selectively amplified within the emulsion. After amplification the beads contain mainly mutated target sequences, some of which are bound to the bead surface while others are free-floating within the emulsions (FIG. 4). Due to the proximity of DNA strands achieved by performing COLD-PCR within emulsion, high enrichment of mutations at any position of the captured target sequences will be achieved in a multiplex fashion.

Temperature-Independent COLD-PCR

According to some aspects of the invention, instead of generating iso-Tm DNA amplicons prior to initiating COLD-PCR, temperature-independent COLD-PCR is performed. This modification removes the requirement that the user isolates iso-Tm or iso-Tc fragments prior to initiating COLD-PCR, and provides a one-step, one-tube procedure for all genomic DNA fragments or fractions thereof. Therefore the described modification enables multiplex COLD-PCR/ice-COLD-PCR on DNA targets with diverse denaturation temperatures, simultaneously. The approach can be used to perform temperature-independent COLD-PCR (TI-COLD-PCR) either in solution, in droplets or on solid support.

In some embodiments, the reaction mixture is dispensed into droplets which are then merged with droplets containing primers for intended DNA targets. TI-COLD-PCR is performed by ramping the denaturation temperatures from lower to higher values so that the entire range of all possible denaturation temperatures is gradually covered. In some embodiments, conventional PCR is performed prior to TI-COLD PCR to enrich the low-abundance mutations prior to TI-COLD PCR.

Assume that for a given sequence the correct Tc is 84.7° C. TI-COLD-PCR is performed for 10 cycles at 80° C., then 10 cycles at 80.3, 10 cycles at 80.6, and so on until a denaturation temperature of 95° C. is reached where all sequences would have been denatured at some stage. At temperature below 84.7° C. none of the target sequences would be denatured and hence no target would amplify. At 84.7° C. the mutated sequences would selectively amplify using the sequence specific primers present in the PCR reaction. Above 84.7° C., all sequences would amplify equally, i.e. the already-enriched mutated sequences plus the wild type sequences would have equal amplification at denaturation temperatures higher than 84.7° C. At the final denaturation temperature of 95° C. the mutated, amplified target sequences would be enriched over wild type sequences. Similarly, for all other target sequences with different Tc, the same scenario would apply: at denaturation temperature below their Tc they would not amplify, at Tc they would amplify only if they are mutated, while above Tc all would amplify equally. Hence overall, at the final denaturation temperature of 95° C. the mutated, amplified target sequences would be enriched over wild type sequences, for all DNA targets present in the reaction.

TI-COLD PCR can be performed in solution in a tube. This requires that for each target sequence there is a separate primer pair and all primers are added together in the reaction. Thus, the primer pair specific to a given sequence would not be used until the denaturation temperature is high enough to reach the critical denaturation temperature Tc where mutant target sequences amplify preferentially over wild-type sequences. At denaturation temperature Tc the primers specific for the target sequence would be substantially consumed in synthesizing mainly the mutant amplicons. At temperature above Tc any remaining primers would be used equally for amplifying the (enriched) mutant sequences plus the wild-type, until completely consumed.

However, a problem with this approach is that the primers would tend to react with each other and form primer-dimers and by-products. This unwanted effect can be avoided by limiting the primer concentration to lowest possible (e.g., in the region of 0.01-0.2 μm), attaching to all target sequences the same primer on one end, and a sequence-specific primer on the other end, or attaching common primers to both ends of all target sequences. Alternatively, TI-COLD PCR can performed in a space constrained manner in droplets as performed by Raindance™ or on solid support as described herein. For example, by using RS-bound beads that have a target-specific primer bound to their surface and a generic forward primer in solution, each emulsion would contain primers specific to the target sequence captured on the RS, therefore avoiding unwanted primer interactions. Therefore ramping of the temperature from lower to higher values would amplify the target sequences selectively in all emulsions simultaneously, without the need to isolate iso-Tc DNA targets or to know a-priori the required Tc for COLD- PCR. In some embodiments, conventional PCR is performed prior to TI-COLD PCR to enrich the low-abundance mutations prior to TI-COLD PCR.

Temperature-Independent COLD-PCR on Solid Support

Beads are encompassed in an emulsion, each bead containing immobilized on its surface (a) reference sequence 1 for target 1, (b) forward primer 1 for target 1. The emulsion also contains (c) reverse primer 1 for target 1, polymerase, dNTP and PCR buffers. Additionally, emulsions 2, 3, 4, etc. similarly contain components for targets 2, 3, 4, etc. The primers are provided within each emulsion in limited quantity, and the primers may be exhausted after about 20-25 cycles. Assume that target 1 has a Tc=84.0° C., target 2 has Tc=85.0° C. and target 3 has a Tc=86°, etc. ice-COLD-PCR is first applied for 20 cycles at Tc for target 1 (Tc=84.0° C.), during which mutation-containing sequences in emulsion containing target 1 are amplified, while wild-type sequences are not amplified. At the same time, none of the targets 2, 3, 4, etc will amplify in other emulsions, as neither wild type nor mutant sequences denature at this denaturation temperature. Following the 20 cycles of ice-COLD-PCR, the primers are exhausted and the reaction within emulsion containing target 1 stops. If additional targets within different emulsions have a Tc similar to that of target 1 (Tc=84.0° C.) then they will also amplify at this temperature, similar to target 1. In this way, all Iso-Tm/iso Tc fragments co-amplify at Tc=84° C. for the initial 20 cycles.

The cycling is then switched for another 20 cycles at Tc for target 2 (Tc=85° C.), during which mutation-containing sequences in emulsion containing target 2 are amplified, while wild-type sequences are practically not amplified. Similarly, following the 20 cycles of ice-COLD-PCR, the primers are exhausted and the reaction within emulsion containing target 2 stops. Targets that also happen to have Tc=85.0° C. co-amplify with target 2. By following the same scheme, denaturation temperatures spanning the entire region of temperatures (e.g. 80-92° C.) are covered in a single tube, single COLD-PCR reaction. Reactions in individual emulsions start whenever the correct Tc is reached and stop whenever the primers are exhausted. This approach ensure that the primers are not be prone to create primer dimmers within emulsions. In some embodiments, all targets have common primers on one or both ends. Because many cycles of PCR are applied in this approach, polymerase that does not get easily inactivated at high temperatures can be used (e.g. Phusion).

The major advantage of this approach is that one does not need to isolate iso-Tm fragments from genomic DNA, or even to know what is the Tm and Tc of the targets. Because the temperature is ramped over all possible denaturation temperatures, starting from lower to higher temperatures, mutation enrichment occurs always until primers are exhausted within all emulsions. Reactions in individual emulsions start whenever the correct Tc is reached and stop whenever the primers are exhausted.

Temperature-Independent COLD-PCR Using Incorporation of Modified Deoxynucleotides During Amplification.

In some embodiments, temperature independent COLD-PCR of multiple DNA fragments having different Tm and Tc is performed in the presence of modified deoxynucleotide triphosphates in the reaction. For example, triphosphates containing modified bases such as: 2'-deoxy-inosine; diamino-purine; iso-guanine; iso-cytosine; methyl-cytosine; 7-(2-thienyl)imidazo[4,5-b]pyridine; 2-nitro-4-propynylpyrrole; aminoallyl-uridine; xanthine; diaminopyrimidine; metal-coordinated bases such as 2,6-bis(ethylthiomethyl)pyridine with silver ion, or a mondentate pyridine with a copper ion; nitroazole analogues; or any other modified nucleotide triphosphate that can be incorporated into DNA by the polymerase during PCR may be used. By incorporating modified bases into DNA during PCR, the Tm of the various DNA fragments becomes more uniform, thus making it easier for TI-COLD-PCR to amplify and enrich mutant sequences in multiple fragments simultaneously.

For example, assume that a given DNA fragment has a 60% GC content and a corresponding high Tm of 90° C., while a second fragment has a 40% GC content and a corresponding Tm of 85° C. If 2'-deoxy-inosine is incorporated in the amplification reaction, this will replace most guanines in both DNA fragments resulting in the formation of inosine:cytosine bonds instead of G:C bonds. Accordingly, the effect of the GC content on the Tm will be reduced or eliminated and both sequences will end up having similar Tm. In the same way, the opposite approach can also be applied. By incorporating 2' amino-purine in the place of adenine, the Tm of all sequences will increase, thus making a uniform high Tm for all fragments.

Such approaches that utilize modified DNA bases will make easier the operation of TI-COLD-PCR, as the Tm of numerous DNA fragments can be brought closer to each other. Thus, the temperature window chosen for TI-COLD-PCR can be narrow and easy to accomplish.

Electrophoretic Techniques to Separate DNA Fragments According to their Tm

In some embodiments, instead of specially-designed primer pairs and PCR amplification to generate iso-Tm DNA fragments, electrophoretic techniques are used to separate DNA fragments according to their Tm. Diverse DNA targets with a range of different Tm (and Tc) are physically separated by gel or capillary electrophoresis and collected in different fractions, each fraction having diverse DNA targets that have essentially the same Tm/Tc. For example, in CDCE (constant denaturant capillary electrophoresis, Khrapko et al. Nucleic Acids Res. 1994 Feb. 11, 22(3):364-369) double stranded DNA fragments are injected through a capillary subjected to a gradient of temperatures. DNA that denatures at a certain Tm1 travels at a different rate through the capillary from non-denatured DNA and therefore separates from double stranded DNA and can be collected as fraction 1. Similarly, DNA that denatures at Tm2 is collected at fraction 2, etc. Each fraction contains DNA targets with diverse sequences, all of which have the same (or very similar) Tm/Tc.

In some embodiments, common adapters are added at the ends of all DNA targets so that they can all be amplified in a single PCR reaction. Following collection, the DNA fragments contained within each fraction can be amplified in a single tube and under the same COLD-PCR program using the common adapters. Accordingly, each fraction requires a different COLD-PCR reaction. Thus, for example, if 20 separate fractions are collected that represent all possible Tm in the region 80-90° C., within 0.5° C. 'bins', one can amplify a substantial part of the human genome and enrich for mutations within each bin. Following 20 separate COLD-PCR amplifications, the amplicons are then mixed and sequenced in a single next generation sequencing run.

Other approaches for physical separation of iso-Tm/iso-Tc diverse DNA fragments include gel electrophoretic means, such as denaturing gradient gel electrophoresis (DGGE), constant denaturant gel electrophoresis (CDGE), temperature gradient gel electrophoresis (TGGE) and temperature gradient capillary electrophoresis (TGCE).

Analyzing the COLD-PCR-Amplified Sequences
Sequencing:

Following enrichment of mutation-containing target sequences via the multiplex COLD-PCR-based approaches and compositions described herein, the amplified DNA fragments can be pooled together by dissolving the emulsion (or by simple purification if the reaction was performed in solution without emulsion) and processed for sequencing by any one of the next generation sequencing (NGS) approaches available, including second and third (single molecule) sequencing technologies. Several NGS approaches incorporate a PCR step as part of the sequencing. Accordingly, one approach is to take advantage of this PCR step and incorporate the COLD-PCR process within the sequencing itself.

Incorporation of COLD-PCR within the 'PCR-Colony' Amplification Step Used in Next Generation Sequencing:

This approach, integrates COLD-PCR within the actual sequencing itself, as opposed to the previous examples that describe iso-Tc COLD-PCR or TI-COLD-PCR that is performed as an independent procedure prior to NGS.

During next generation sequencing, the target DNA is immobilized on solid support and PCR-amplified clonally to form PCR-Colonies (also known as 'Polonies'), following which sequencing on solid support takes place. The present invention enables the simultaneous amplification of numerous iso-Tm fragments on solid support using COLD-PCR. Because of the proximity of targets immobilized on solid support, COLD-PCR is expected to be highly efficient, essentially amplifying only mutation-containing sequences which are then directly sequenced. Thereby the efficiency of next generation sequencing is predicted to increase by several orders of magnitude since essentially ONLY mutation containing sequences are read. Essentially this provides next generation sequencing of mutant-only DNA.

Iso-Tm or iso-Tc COLD-PCR on Solid Support, as Part of Polony-Formation Step within Next Generation Sequencing.
A. Aimed Towards the Illumina Platform
1. iso-Tm or iso-Tc fragments are made from genomic DNA, using one of the methods described herein. Fragmentation is not performed randomly, and the result is single-stranded targets with common adaptors.
2. Target DNA is bound randomly to the inside surface of the flow cell channels.
3. Nucleotides and polymerase is added to initiate solid-phase bridge full-COLD-PCR amplification of iso-Tm/iso-Tc fragments.
4. Full-COLD-PCR on solid support will allow denaturation of mismatch-containing sequences formed by hybridization of immobilized mutant sequences with adjacent immobilized wild-type sequences, while non-mismatched sequences (wild type) will be effectively suppressed.
5. Denatured sequences contain a high percent of mutation-containing sequences
6. Dense clusters of double-stranded DNA enriched in mutation-containing sequences are generated in each channel of the Illumina flow-cell.
7. This is followed by sequencing-by-synthesis, according to the Illumina platform.
B. Aimed Towards the Roche-454 Platform, or the Ion Torrent System (PCR in Emulsion)
1. Make iso-Tm or iso-Tc fragments from genomic DNA, using one of the methods described herein. Fragmentation is not performed randomly, and the result is single-stranded DNA targets. In some embodiments, the targets contain common adaptors.
2. Bind target DNA to beads containing dense primers on their surface, each primer specific for a different target. In some embodiments, the primers recognize the common adaptors.
3. Mix targets with beads at a ratio of less than 1 target per bead, then enclose beads in emulsion together with nucleotides, polymerase and one of the two primers that are also immobilized on the bead as per the Roche-454 protocol.
4. Initiate emulsion-based full-COLD-PCR amplification of iso-Tm fragments. Full-COLD-PCR immobilized on beads enclosed in nano-reactors (emulsion) enables rapid hybridization of mutant with wild type sequences that allows denaturation of adjacent immobilized wild-type sequences.

BEAM and Flow-Cytometry:

It may be desirable to isolate beads/emulsions that contain mutated sequences that have been amplified during COLD-PCR, and discard beads that contain only wild type sequences, in order to make subsequent sequencing even more efficient. In the case where iso-Tc sequences have been first isolated from genomic DNA prior to COLD-PCR, one expects that the only emulsions containing copious DNA amounts are those that include mutated sequences, since in the emulsions with wild-type sequences there will be little amplification. In this case, beads with amplified DNA can be sorted via high throughput flow-cytometry in the presence of DNA-binding dye, in an approach similar to BEAM technology (see Li M, Diehl F, Dressman D, et al. BEAMing up for detection and quantification of rare sequence variants. Nat Methods 2006; 3(2):95-7). The population of beads that produce strong fluorescence signals is the one that contains amplified mutated sequences and can be sorted and sequenced.

REpeated DNA-Strand SEparation at Critical Denaturation Temperatures (RE.SE.CT)

According to one aspect of the invention, a method that enables identification of variant-sequence alleles (mutant target sequences) in the presence of a large excess of non-variant alleles (wild type target sequences) in nucleic acids without the complication of polymerase-introduced errors or other primer-introduced artifacts is provided. The enrichment that can be obtained via PCR-based methods has a limit, since after several cycles of synthesis the polymerase unavoidably introduces mis-incorporations (PCR errors) that are subsequently scored as mutations. Repeated PCR/COLD-PCR can also introduce mis-priming that results to amplification of unwanted non-target sequences. Furthermore, there are powerful genetic analysis methods currently emerging ('third generation sequencing') that may obviate the use of PCR altogether.

Figure 11:
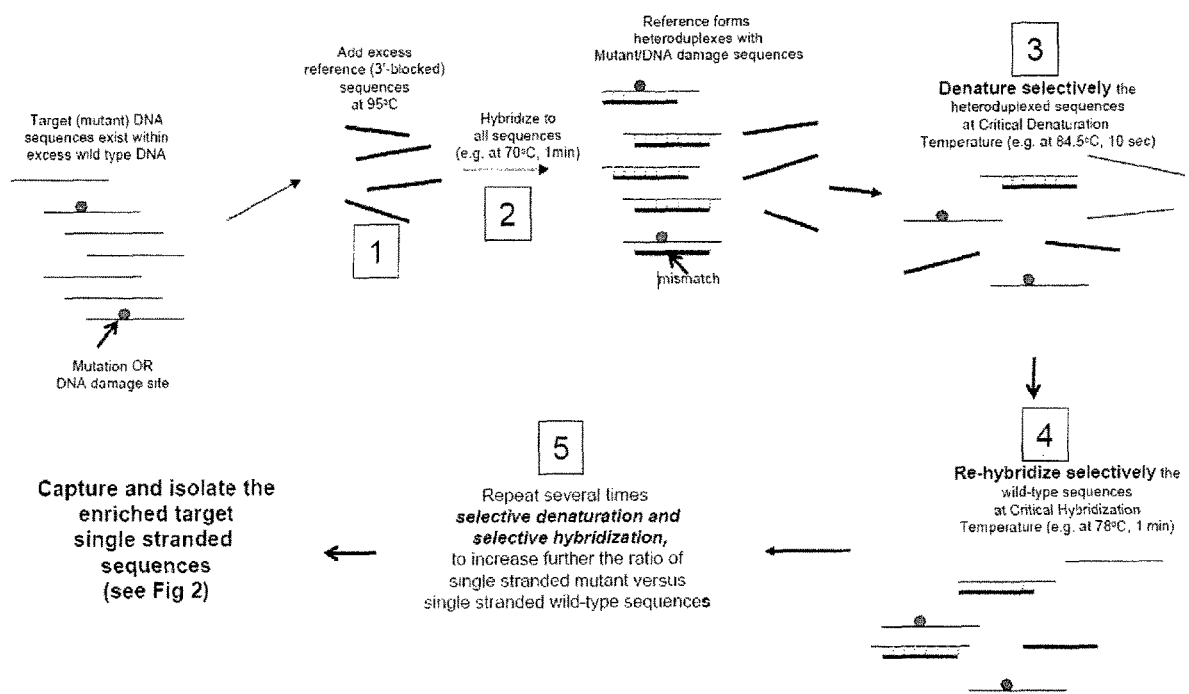
FIG. 11 shows the isolation of target DNA regions via repeated denaturation and hybridization.

RE.SE.CT allows the enrichment of mutant target sequences without introducing mis-incorporations, and amplifies preferentially minority alleles from mixtures of wild type and mutation-containing sequences, irrespective where the mutation lies, thereby providing a high enrichment of the mutated sequences without PCR and without introducing any artifacts. RE.SE.CT exploits the observation that double stranded DNA sequences containing one or more single base mismatches denature fast and re-associate slowly relative to fully-matched sequences (FIG. 11). By fixing the denaturation temperature to Tc, mutations at any position along the sequence are enriched during RE.SE.CT. Subsequently the enriched sequences can be screened with any of the currently available methods for detecting mutations, including Sanger Sequencing, high resolution melting (HRM), SSCP, next generation sequencing, and MALDI-TOF.

The method can be used for multiplexed detection of DNA methylation, and for enriching mutant DNA strands, and damaged DNA strands, such as DNA containing abasic sites that result from exposure to DNA damaging agents. The abasic site position would create a mismatch upon hybridization to the reference sequence, thus enabling its selective denaturation upon RE.SE.CT. Unlike with ice-COLD-PCR-based applications that require DNA polymerase to operate, in RE.SE.CT the 3' end of RS does not need to be blocked, as long as no polymerase is used in the mutation enrichment process. One advantage of this approach is that it is easy to synthesize the reference sequence using a simple PCR reaction rather than synthesis on oligonucleotide synthesizers which is expensive. This allows also larger reference sequences to be used, e.g. 200 bp RS. This is a substantial advantage over COLD-PCR.

In one embodiment, a method for preparing a single stranded mutant target sequence from a mixture of target sequences suspected of containing both the mutant target sequence and a wild type target sequence is provided. The method comprises: heating target sequences suspected of containing both mutant target sequences and wild type target sequences to a denaturing temperature that is above the melting temperature of the target sequences. This allows the formation of a mixture containing single stranded mutant sequences and single stranded wild type sequences. The mixture is then contacted with an excess references sequence that is complementary to the wild type sequence, and a complete hybridization steps is performed, i.e., the temperature is reduced to permit formation of target strand/reference strand duplexes, wherein the duplexes include mutant strand/reference strand duplexes and wild type strand/reference strand duplexes. Next, a selective denaturation step is performed, i.e., the temperature is raised to a critical denaturation temperature that is below the melting temperature of the wild type strand/reference strand duplexes to permit selective denaturation of mutant strand/reference strand duplexes, whereby the ratio of single stranded mutant target sequences relative to single stranded wild type target sequences is increased.

In some embodiments, the wild type strand/reference strand duplexes formed by selective denaturation are removed. Optionally, in some embodiments, the complete hybridization step, the selective denaturation step, and the removal of the wild type strand/reference strand duplexes formed by selective denaturation are repeated at least 1, 2, 3, 5, 10, 50, 75, 100, 200, 300, 400, 500, 600, 700, 800, 900, or 1000 times. In some embodiments, additional excess of reference sequence is added after the removal of the wild type strand/reference strand duplexes.

Optionally, in some embodiments, the method further comprises performing a selective hybridization step, i.e., the temperature is reduced to a critical hybridization temperature to permit selective formation of wild-type target sequence/reference sequence duplexes relative to formation of mutant sequence/reference sequence duplexes. In some embodiments, the selective denaturation and selective hybridization steps are repeated at least 1, 2, 3, 5, 10, 50, 75, 100, 200, 300, 400, 500, 600, 700, 800, 900, or 1000 times to further enrich for the single stranded mutant target sequences.

Optionally, in any of the foregoing embodiments, the reference sequences are attached to particles. Optionally, in any of the foregoing embodiments, the reference sequences are attached to magnetic particles.

Optionally, in some embodiments, the target sequences are contacted with an excess of at least two different reference sequences, each different reference sequence being complementary to a different wild-type target sequence, and the duplexes formed by the wild type sequences/reference sequences having substantially the same melting temperature, or substantially the same critical denaturation temperature (Tc). In some embodiments, the target sequences are contacted with an excess of at least 10, 15, 20, 30, 40, 50, 100, 200, 500, or 1000 different reference sequences.

Optionally, in some embodiments, the method further comprises detecting the single stranded mutant target sequences. Optionally, in some embodiments, the method further comprises isolating the single stranded mutant target sequences.

Figure 12:
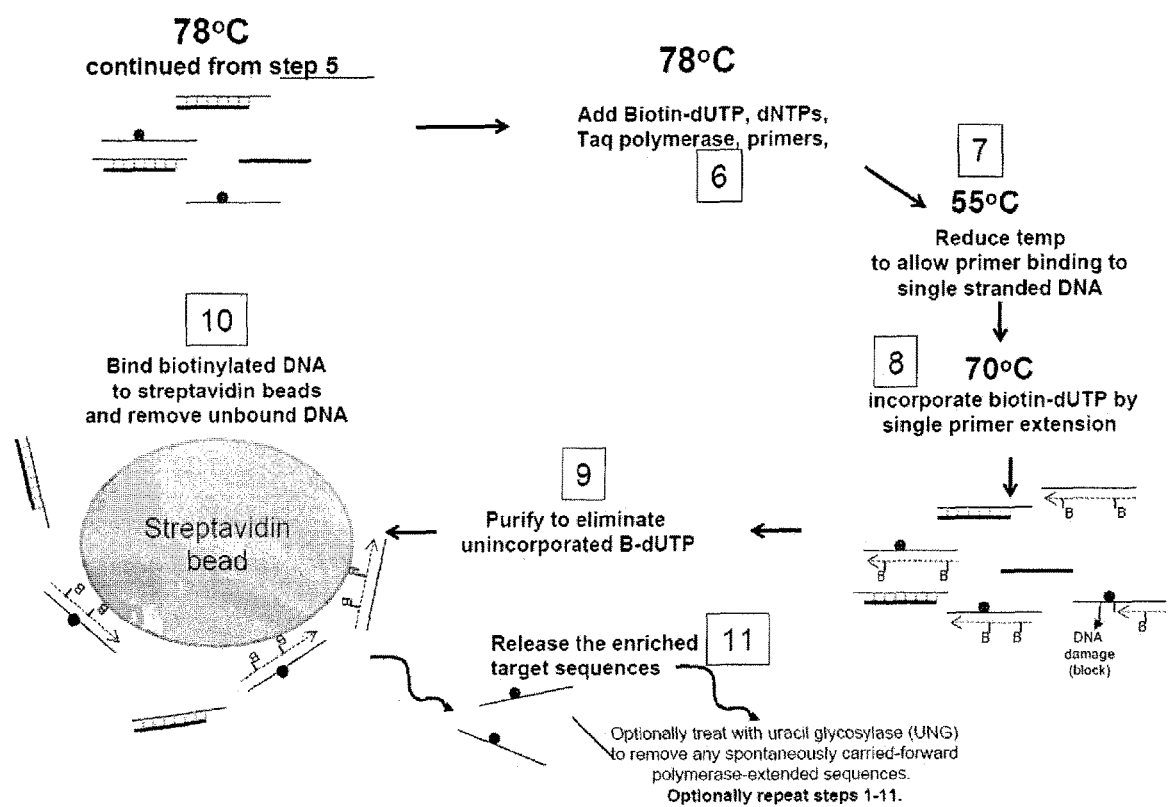
FIG. 12 shows the capture and isolation of mutation (or DNA damaged)-enriched single stranded sequences by primer extension.

In some embodiments, the single stranded mutant target sequences are isolated by contacting the single stranded mutant target sequences with primers (FIG. 12). The temperature is then is rapidly lowered to 50-55° C. to allow binding of primer to those sequences that are single stranded. The temperature is raised to 65-70° C. to enable single primer extension via a polymerase, in the presence of tagged dNTPS. The result is that mutant sequences selectively obtain a tagged complementary sequence. Following this, the tagged sequences are immobilized on solid support coated with a capture moeity, and the non-tagged DNA (which is mainly wild-type DNA) is removed. The single-stranded, mutated sequences are then recovered from the solid support, for example, by thermal denaturation at 95° C. The mutated sequences that are recovered represent the original DNA target template, not the template generated via the polymerase extension—which is tagged and stays bound to the solid support after denaturation. In some embodiments, the tag moiety is biotin, and the capture moiety is avidin, or vice versa.

Alternatively, in order to selectively tag the single stranded mutant sequences, one could use a tagged primer, instead of adding tagged dNTP to the solution. In some embodiments, the tag moiety is biotin, and the capture moiety is avidin, or vice versa.

Figure 13:
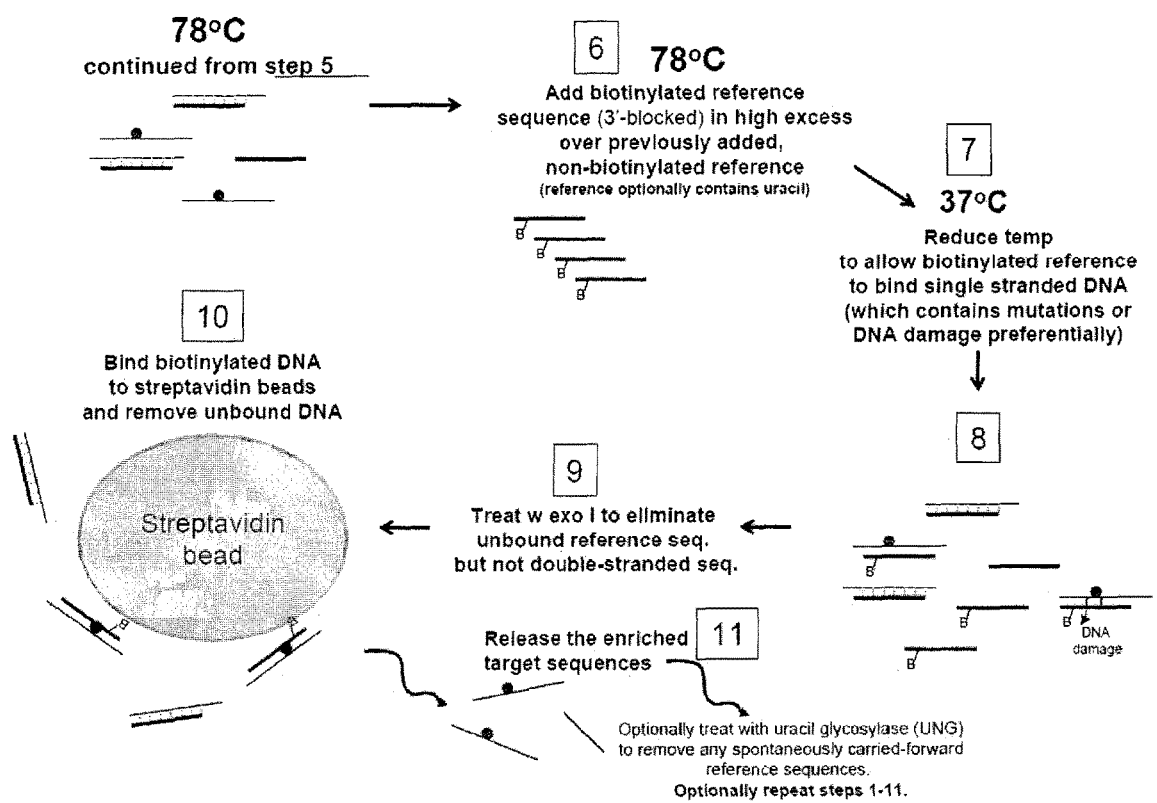
FIG. 13 shows the capture and isolation of mutation (or DNA damaged)-enriched single stranded sequences by hybridization to excess biotinylated reference.

In some embodiments, the single stranded mutant target sequences are isolated by adding an excess of tagged reference sequences (FIG. 13). The temperature is then rapidly reduced to below 50° C. to permit formation of single stranded mutant target sequence/tagged reference sequence duplexes. In the next step the excess reference probe is eliminated, for example, by exonuclease treatment, and the tagged sequences are captured on a support coated with a capture moiety. The single-stranded, mutated sequences are then recovered from the solid support, for example, by thermal denaturation at 95° C. In some embodiments, the tag moiety is biotin, and the capture moiety is avidin, or vice versa.

Figure 14:
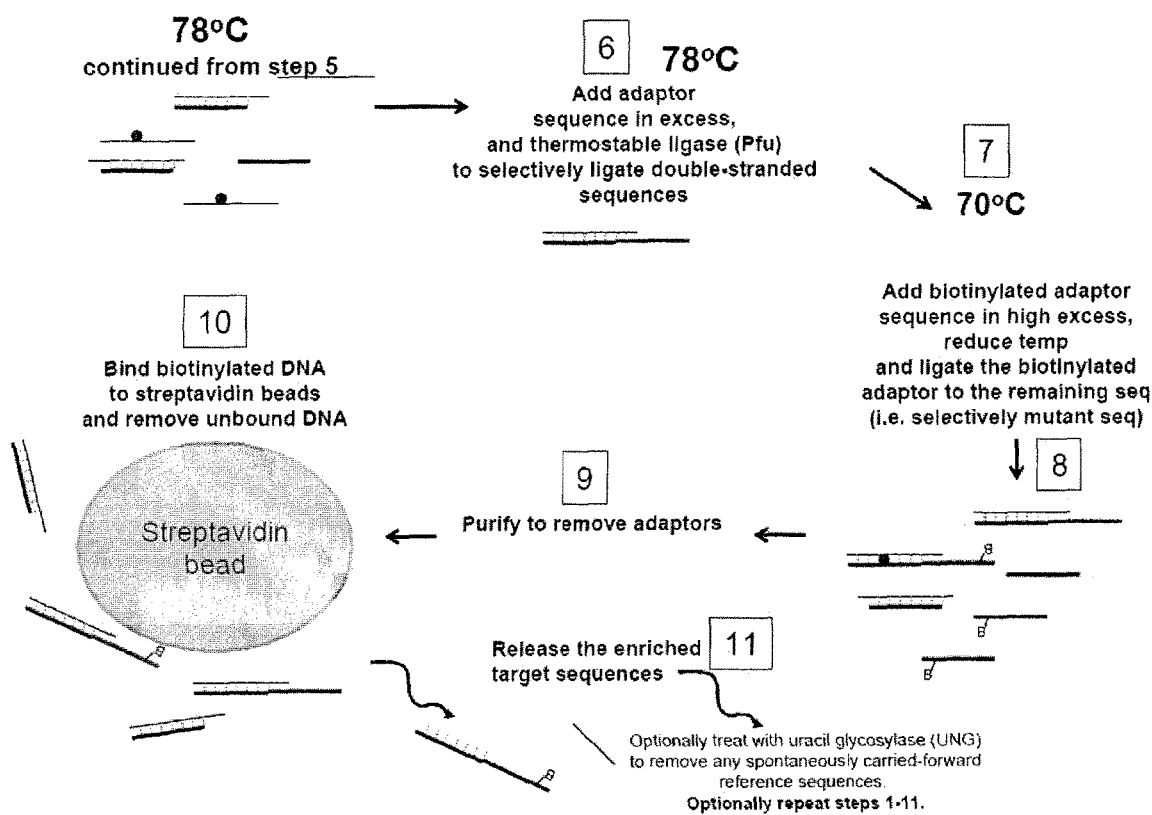
FIG. 14 shows the capture and selective biotinylation of single stranded sequences via selective ligation at critical denaturation temperatures.

In some embodiments, the single stranded mutant target sequences are isolated by contacting the formed duplexes with an excess of non-tagged adaptor and thermostable ligase at critical hybridization temperature (e.g. 78° C.). The non-tagged adaptor preferentially ligates to double-stranded templates. In this way, the non-tagged adaptor will ligate selectively to the wild type alleles, since these are in duplexes with the reference sequences (FIG. 14), but not to mutant alleles since these are mainly single-stranded. Next, a tagged adaptor that is in high excess over the previously added, non-tagged adaptor is used and the temperature is reduced rapidly so that the target DNA binds to reference sequence and tagged adaptor ligates to all remaining double stranded sequences (that would be expected to be mainly mutant sequences, since the majority of wild type sequences was ligated to a non-tagged adaptor). Subsequently tagged sequences are captured on support coated with a capture moiety. The single-stranded, mutated sequences are then recovered from the solid support, for example, by thermal denaturation at 95° C. In some embodiments, the tag moiety is biotin, and the capture moiety is avidin, or vice versa.

In some embodiments, the single stranded mutant target sequences are isolated by using tagged reference sequences. The duplexes formed by wild type sequence/tagged reference sequence are removed by capture on solid surface coated with a capture moiety, thereby leaving an enriched population of single-stranded mutant target sequences. In some embodiments, the tag moiety is biotin, and the capture moiety is avidin, or vice versa.

Figure 15:
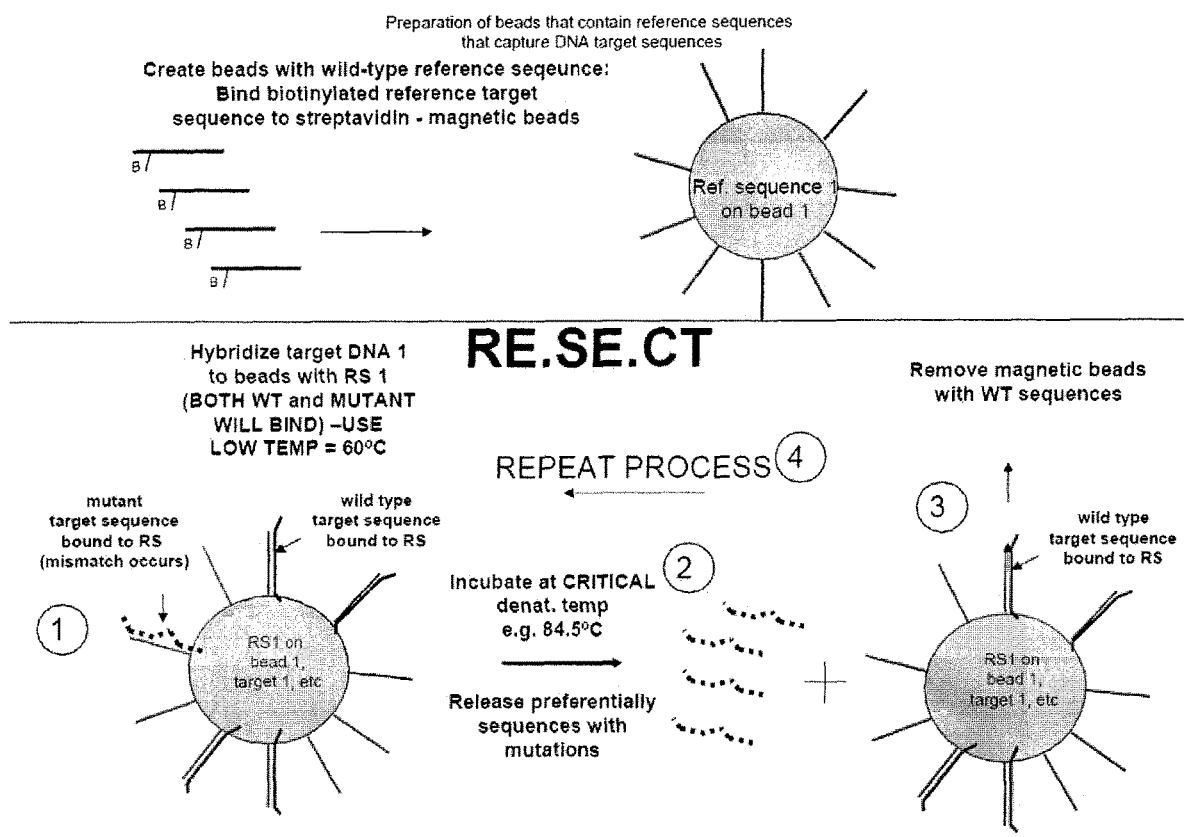
FIG. 15 shows an illustration of the RE.SE.CT concept.

In some embodiments, the single stranded mutant target sequences are isolated by using reference sequences attached to magnetic beads. After performing the selective denaturation step, that permits selective denaturation of mutant strand/reference strand duplexes, but not the wild type strand/reference strand duplexes, the magnetic beads are removed, thereby resulting in the removal of all reference sequences plus any duplexes formed with the reference sequences. In some embodiments, additional excess reference sequence attached to magnetic beads is added, and the process is repeated at least 1, 2, 3, 5, 10, 50, 75, 100, 200, 300, 400, 500, 600, 700, 800, 900, or 1000 times. The reference sequence can be bound through the 5' or the 3' end on magnetic beads, and magnets can be turned on and off to enable repeated removal of magnetic beads from the reaction, following selective denaturation of mutated sequences. Size of reference-sequence-bound-beads (RS-beads) can vary from large (5 micrometers) to small (nanometers diameter). (FIG. 15)

As an alternative to using magnetic beads, the reference sequences can be immobilized on any other kind of solid support (e.g. within capillaries made of glass, polymers or other compounds; or within micro-fluidic devices or micro-fluidics 'chips' in very small volumes). Alternatively, the solution of DNA target sequences can be driven through the solid support (e.g. forced to go through the capillaries through pressure or capillary movement) to generate exchanges between micro-chambers. By regulating the temperature along the capillaries/micro-fluidics appropriately, one can enable binding of both mutation-containing and WT sequences to the reference sequence, as well as selective denaturation of mutation-containing sequences, that will then move through the capillaries as an enriched population of molecules. Thus the mutation-containing sequences will remain in solution and can be recovered for downstream assays.

In some embodiments, the target sequences are pre-amplified using asymmetric PCR prior to contacting with the reference sequences. Asymmetric PCR preferentially amplifies one DNA strand in a double-stranded DNA template, and is routinely used in sequencing and hybridization probing where amplification of only one of the two complementary strands is required. PCR is carried out as usual, but with a great excess of the primer for the strand targeted for amplification. Because of the slow (arithmetic) amplification later in the reaction after the limiting primer has been used up, extra cycles of PCR are required.

In some embodiments, the target sequences are contacted to the reference sequences in the presence of an organic solvent. Organic solvents present during the binding of interrogated target sequences to the reference sequences can have beneficial effects. For example, solvents like betaine, DMSO, formamide and others enhance the hybridization fidelity of nucleic acids. As a result, the temperature-difference between a perfectly matched wild-type sequence and a mutation-containing sequence is exaggerated in the presence of organic solvents. In addition, the melting temperature (Tm) is reduced when organic solvents are present, thus enabling RE.SE.CT to operate at lower temperature that are easier to achieve and that avoid potential temperature-caused damage to the DNA strands. At the same time, DNA fragments with substantially different DNA melting temperatures in regular aqueous buffer end up with melting temperatures that are closer to each other when organic solvents are used, thus making multiplexing easier. Organic solvents as much as 50% or higher can be used during RE.SE.CT since there is no enzyme involved in the process and as a result the organic solvent does not inhibit any part of the process.

RE.SE.CT can be used in conjunction with COLD-PCR, in order to increase even further the mutation enrichment obtained via COLD-PCR. Therefore one may envision COLD-PCR to enrich mutated sequences by 10-fold; then the sample is used for RE.SE.CT to enrich mutated sequences by another 10-fold; and so on. In this way COLD-PCR and RE.SE.CT act synergistically to increase the mutation enrichment. RE.SE.CT may also be used in conjunction with different amplification methods, e.g. with isothermal amplification well known in the art, such as LAMP, SPIE, etc.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

Materials and Methods

Source of Genomic DNA

Reference human male genomic DNA was purchased from Promega and used as wild-type DNA in dilution experiments. Genomic DNA from human cell line SW480 (containing TP53 exon 8 mutation c.818 G>A, TP53 exon 9 c.925 C>T), and T47D (containing TP53 exon 6 c.580 C>T) were purchased from ATCC. Primers and anchors were synthesized by Integrated DNA Technologies.

TP53 Exons 8-9 Target Isolation by Streptavidin Coated Magnetic Beads

Genomic DNA was first digested with restriction endonuclease EcoO109I to release a 336-bp fragment containing TP53 exons 8-9. Reactions were incubated at 37° C. for 3.5 hr, consisting of 5014 DNA, 100 units EcoO109I, 1×NEB buffer 4, and 100 µg/ml BSA. Digested DNA was purified through Microcon YM-30 columns, and eluted in water. To capture the 336-bp fragments, purified DNA was hybridized to a 5'-biotinylated probe (5'-biotin-GAA TCT GAG GCA TAA CTG CAC C-3'; SEQ ID NO: 1), which is complementary to the sense-strand sequence of the intron region between exons 8-9. Hybridization reactions were conducted in 6×SSPE buffer (American Bioanalytical) with 2-5 µg purified genomic DNA and 33 nM biotinylated probe, and incubated at 42° C. for 2 hr in a thermocycler. The hybridized reactions were then purified through Microcon YM-30 column to remove excess probe, and eluted in 20 µl water. Capture of ssDNA targets by Dynabeads were performed essentially as described by Li, et al. Briefly, 20 µl probe- DNA hybrids were mixed with 20 µl pre-washed Dynabeads M-270 Streptavidin (Invitrogen) at room temperature for 1 hr, followed by three washes with 1× binding and washing buffer (5 mM Tris-HCl, pH7.5, 0.5 mM EDTA, and 1 M NaCl) supplemented with 0.1% Tween 20, twice with 1× binding and washing buffer, and once with water. The beads were resuspended in 20 µl water, and ssDNA target was released by denaturation at 95° C. for 5 min followed by immediate placement of the tubes on the DynaMag magnets (Invitrogen). The suspension was recovered for further analysis.

Quantification of Isolated TP53 Target

Enrichment of target capture was estimated by measuring the relative abundance of TP53 exon 8 to GAPDH gene before and after beads pull-down using real time PCR, which is at least 1000 fold. Quantification of isolated TP53 target was achieved by real-time quantitative PCR using a standard curve generated with EcoO109I-digested, column-purified genomic DNA. PCR reactions were performed in 1× Phusion high-fidelity (HF) buffer (Finnzymes), 0.2 mM dNTPs (each), 0.2 µM (each) of forward and reverse primer, 1×LCGreen$^{Plus+}$ (Idaho Technology) and 0.5 U Phusion DNA polymerase (Finnzymes) in 25 µl volume. The primers used were: 5'-CCTGACCTGCCGTCTAGAAAA-3' (SEQ ID NO: 2; GAPDH-forward); 5'-CTCCGACGCCTGCTT-CAC-3' (SEQ ID NO: 3; GAPDH-reverse); 5'-TGCCTCTTGCTTCTCTTTTC-3' (SEQ ID NO: 4; TP53-exon 8-forward); and 5'-CTTTCTTGCGGAGAT-TCTCTTC-3' (SEQ ID NO: 5; TP53-exon 8-reverse). The PCR cycling programs were 98° C. for 30 s; 50 cycles of 98° C. 10 s, $T_a$ 20 s (fluorescence reading on), 72° C. 10 s; hold at 72° C. for 600 s; DNA melting from 60° C. to 95° C. at 0.2° C./s with fluorescence reading on. The annealing temperature ($T_a$) for GAPDH and TP53-exon 8 were 68° C. and 65° C., respectively.

Conventional and Fast-COLD-PCR Using Bead-Isolated ssDNA

Conventional or fast-COLD-PCR reactions for TP53 exon 8 were performed using 7 ng genomic DNA or 2,100 copies of purified ssDNA in 25 µl reaction volume on a Cepheid SmartCycler™ machine. The final concentrations of other reagents and conventional PCR cycling were as described in section 5.3. Thermocycling conditions of fast-COLD-PCR for genomic DNA and bead-isolated ssDNA were defined in Table 1. The difference between the two strategies is reflected by the number of conventional PCR cycles performed before switching to COLD-PCR, i.e. 26 cycles using genomic DNA vs. 18 cycles using bead isolated ssDNA. The critical denaturation temperature ($T_c$) was defined as $T_m-1$; The $T_c$ was 88.7° C. for this study. PCR products were digested using Exonuclease I (New England Biolabs) and Shrimp Alkaline Phosphatase (USB) [15], and sequenced with a nested forward primer (5'-TTGCTTCTCTTTTCCTAT-3'; SEQ ID NO: 6) at the Molecular Biology Core Facility (Dana Farber Cancer Institute).

TABLE 1

COLD-PCR thermocycling conditions for genomic DNA and bead-isolated ssDNA.

| Template | Step | Conditions |
|---|---|---|
| Genomic DNA | Initial denaturation | 98° C. for 30 s |
| | Stage 1 cycling: 35 cycles* | 98° C. for 10 s |
| | | 65° C. for 20 s, fluorescent reading |
| | | 72° C. for 10 s |

TABLE 1-continued

COLD-PCR thermocycling conditions for genomic DNA and bead-isolated ssDNA.

| Template | Step | Conditions |
|---|---|---|
| | Stage 2 cycling: 25 cycles | 87.7° C. for 10 s |
| | | 65° C. for 20 s, fluorescent reading |
| | | 72° C. for 10 s |
| | Extension | 72° C. for 600 s |
| | Melting Curve | Ramping 0.2° C./s, 60° C. to 90° C. |
| Bead-isolated ssDNA | Initial denaturation | 98° C. for 30 s |
| | Stage 1 cycling: 18 cycles | 98° C. for 10 s |
| | | 65° C. for 20 s, fluorescent reading |
| | | 72° C. for 10 s |
| | Stage 2 cycling: 52 cycles* | 87.7° C. for 10 s |
| | | 65° C. for 20 s, fluorescent reading |
| | | 72° C. for 10 s |
| | Stage 3 cycling: 25 cycles | 87.7° C. for 10 s |
| | | 65° C. for 20 s, fluorescent reading |
| | | 72° C. for 10 s |
| | Extension | 72° C. for 600 s |
| | Melting Curve | Ramping 0.2° C./s, 60° C. to 90° C. |

*For this stage, 35 and 52 cycles are the maximum number of cycles that can be completed before advancing to the next stage; however, this program is designed to automatically proceed to the next thermocycling stage when the fluorescence reaches the PCR threshold ($C_t$ set to 30 fluorescence units).

Long-Range PCR to Amplify TP53 Exon 5-9

To amplify TP53 exons 5 to 9, a conventional long-range PCR reaction was performed directly with 20 ng genomic DNA from cell lines diluted into human male genome DNA in a 20 µl volume. The final concentrations of other reagents were as in section 5.3 with the following forward primer (5'-ACTTCAATGCCTGGCCGTAT-3' SEQ ID NO: 7) and reverse primer (5'-Biotin-GCCCCAAT-TGCAGGTAAAAC-3' SEQ ID NO: 8). The size of the PCR amplicon is 2522 bp in length. The PCR cycling was performed on an Eppendorf machine as follows: 98° C. for 30 s and 30 cycles of 98° C. for 10 s, 65° C. for 20 s, 72° C. for 1 min, followed with 72° C. for 5 min. PCR products were purified with the QIAquick PCR purification kit (Qiagen Inc.) to remove free biotinylated primers, followed by magnetic bead isolation as described herein.

Anchor Annealing and Gap-Filling

Beads linked with ssDNA were resuspended in 1× Ampligase reaction buffer (Epicentre Inc.), followed by adding 0.16 pmol of anchor primers for each targeted region (Table 2). The mixture was denatured at 100° C. for 1 min and immediately cooled down on ice for 5 min, followed with incubation at 60° C. for 15 min in a hybridization oven. A 2 µl mixture containing 1× Ampligase reaction buffer, 0.2 mmol/L of each deoxynucleotide triphosphate, 2 units of AmpliTaq DNA polymerase, Stoffel Fragment (Applied Biosystems), 2.5 units of Ampligase (Epicentre) was added, and the reaction was incubated at 60° C. for 1 hr in a hybridization oven. The beads were then washed with 2 times of 1× Binding and Washing Buffer and 3 times of water, followed by resuspension in 15 µl water. Beads were denatured at 95° C. for 2 min, followed by immediately placing on the DynaMag magnates. A 12 µl supernatant was collected and stored at 4° C.

TABLE 2

Sequence of anchor primers

| Anchors * | | PCR Size | $T_c$ |
|---|---|---|---|
| TP53 exon 6 | Left: GCCTCCCTCGCGCCATCAGAGGG TCCCCAGGCCTCTGA (SEQ ID NO: 9) Right: Phosphate-TTGGATGACAGAA ACACTTTTCGCTGAGCGGGCTGGCAAGGC (SEQ ID NO: 10) | 157 bp | 85° C. |
| TP53 exon 8 | Left: GCCTCCCTCGCGCCATCAGTGCC TCTTGCTTCTCTTTTCCT (SEQ ID NO: 11) Right: Phosphate-CCGCAAGAAAGG GGAGCCTCTGAGCGGGCTGGCAAGGC (SEQ ID NO: 12) | 174 bp | 86° C. |
| TP53 exon 9 | Left: GCCTCCCTCGCGCCATCAGTCAC CTTTCCTTGCCTCTTTCC (SEQ ID NO: 13) Right: Phosphate- TGGATGGAGAAT ATTTCACCCTTCTGAGCGGGCTGGCAAGGC (SEQ ID NO: 14) | 134 bp | 84.5° C. |

* 454 primer A and B are underlined. Note that the sequences of right anchors are complementary to primer B, while those of left anchors are identical to primer A.

Conventional and COLD-PCR with Generic Primers

Conventional or COLD-PCR reactions were performed directly with 2 μl purified ssDNA in a 25 μl volume. The final concentration of other reagents were as follows: 1×GoTaq Flexi Buffer (Promega), 0.63 U of GoTaq Flexi DNA polymerase (Promega), 0.2 mmol/L of each deoxynucleotide triphosphate, 0.2 μmol/L (each) primer 454-A and B, 2.5 mmol/L MgCl$_2$ and 0.1×LCGreen$^{Plus+}$. The conventional PCR cycling was as follows: 95° C. for 120 s and 35 cycles of 95° C. for 15 s, 53° C. for (fluorescence reading on) 30 s and 72° C. for 30 s. PCR cycling conditions for simplex- and duplex-COLD PCR are summarized in Table 3.

Simplex PCR was sequenced with 454-A primer or 454-B primer, and duplex PCR was sequenced after a nested conventional PCR (Table 4).

TABLE 3

Thermocycling conditions for simplex- and duplex-COLD-PCR

| PCR format | Step | Conditions |
|---|---|---|
| Simplex-COLD* Duplex-COLD (1 $T_c$) | Initial denaturation Stage 1 cycling: 5 cycles | 95° C. for 120 s 95° C. for 15 s 53° C. for 30 s, fluorescent reading 72° C. for 30 s |
| | Stage 2 cycling: 25 cycles | $T_c$ for 15 s 53° C. for 30 s, fluorescent reading 72° C. for 30 s |
| | Melting Curve | Ramping 0.2° C./s, 60° C. to 90° C. |
| Duplex-COLD (2 $T_c$s) | Initial denaturation Stage 1 cycling: 5 cycles | 95° C. for 120 s 95° C. for 15 s 53° C. for 30 s, fluorescent reading 72° C. for 30 s |
| | Stage 2 cycling: 12 cycles | 84.5° C. for 15 s 53° C. for 30 s, fluorescent reading 72° C. for 30 s |
| | Stage 3 cycling: 12 cycles | 85° C. for 15 s 53° C. for 30 s, fluorescent reading 72° C. for 30 s |
| | Melting Curve | Ramping 0.2° C./s, 60° C. to 90° C. |

*$T_c$ for simplex- and duplex-cold (1 $T_c$) is 86 and 84.7° C., respectively.

TABLE 4

Sequence of nested PCR primers

Nested Primers

TP53 exon 6 forward:
gtaaaacgacggccagtAGGGTCCCCAGGCCTCTGA (SEQ ID NO: 15)
reverse: tcccgcgaaattaatacgacCGAAAAGTGTTTCTGTCATCCAA (SEQ ID NO: 16)

TP53 exon 9 forward:
gtaaaacgacggccagtTCACCTTTCCTTGCCTCTTTCC (SEQ ID NO: 17)
reverse: tcccgcgaaattaatacgacAAGGGTGAAATATTCTCCATCCA (SEQ ID NO: 18)

Tags (underlined) i.e. M13 and tag1 sequence were added to the 5' end of gene-specific nested primers in order to improve the sequencing of short amplicons.

Results and Discussion fast-COLD-PCR Using ssDNA Template Isolated by Magnetic Beads It has been previously demonstrated that sensitivity of mutation detection is significantly improved by performing two successive rounds of COLD-PCR, as opposed to a single COLD-PCR (Li J, Milbury C A, Li C, Makrigiorgos G M. Two-round coamplification at lower denaturation temperature-PCR(COLD-PCR)-based sanger sequencing identifies a novel spectrum of low-level mutations in lung adenocarcinoma. Hum Mutat 2009; 30:1583-90). However, performing multiple rounds of COLD-PCR increases the chance of DNA polymerase-introduced PCR errors which would be subsequently enriched concurrently along with genuine mutations during COLD-PCR.

Described herein is an approach to enhance the mutation enrichment enabled by COLD-PCR, while also limiting the number of required PCR cycles. To evaluate this concept, we isolated target DNA fragments from genomic DNA using a biotinylated probe which was hybridized to the target DNA, followed by streptavidin-coated magnetic bead isolation. This step provides preliminary enrichment of target sequences, eliminating the need to perform PCR. Performing real-time PCR on a target region (GAPDH gene) that was not captured on beads, versus performing real-time PCR on the captured target region (TP53 exons 8-9), we demonstrated that enrichment of the target versus non-target regions via magnetic bead isolation is at least 1.000-fold. The copy number of bead-isolated TP53 target was measured using quantitative real-time PCR, and approximately 2,100 copies of isolated target was then used in fast-COLD-PCR reactions. Genomic DNA containing the equivalent number of copies of TP53 as starting material was also examined in order to compare the performance of COLD-PCR when applied using bead-enriched target versus genomic DNA (non-enriched).

Figure 5:
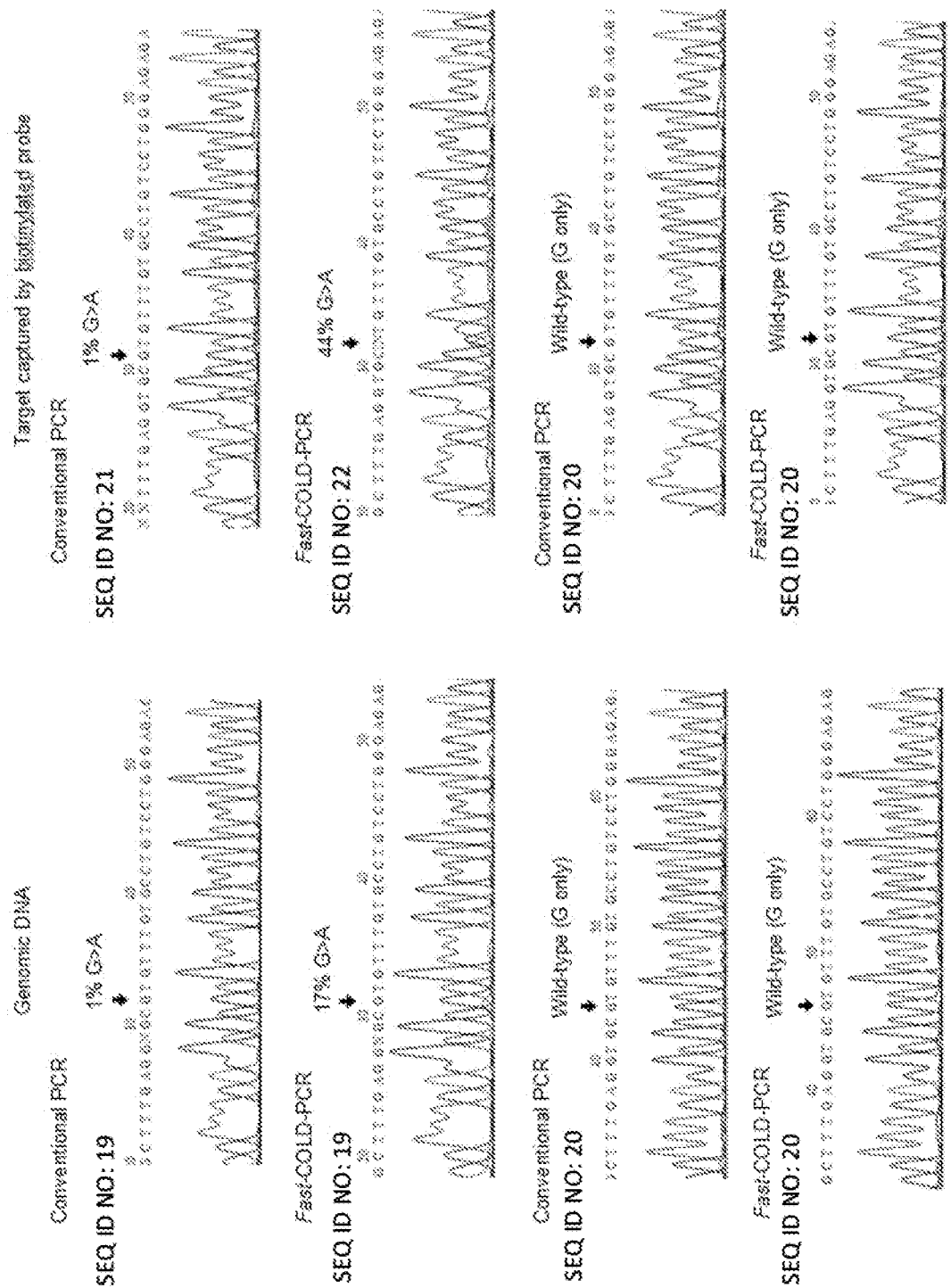
FIG. 5 demonstrates that the sensitivity of mutation detection by fast-COLD-PCR was significantly enhanced following target isolation by biotinylated probe. The cell line used was SW480, which contains TP53 exon 8 c.818 G>A mutation. A wild-type DNA was processed as a control, in parallel. The arrows indicate the position of the mutation.
Figure 6:
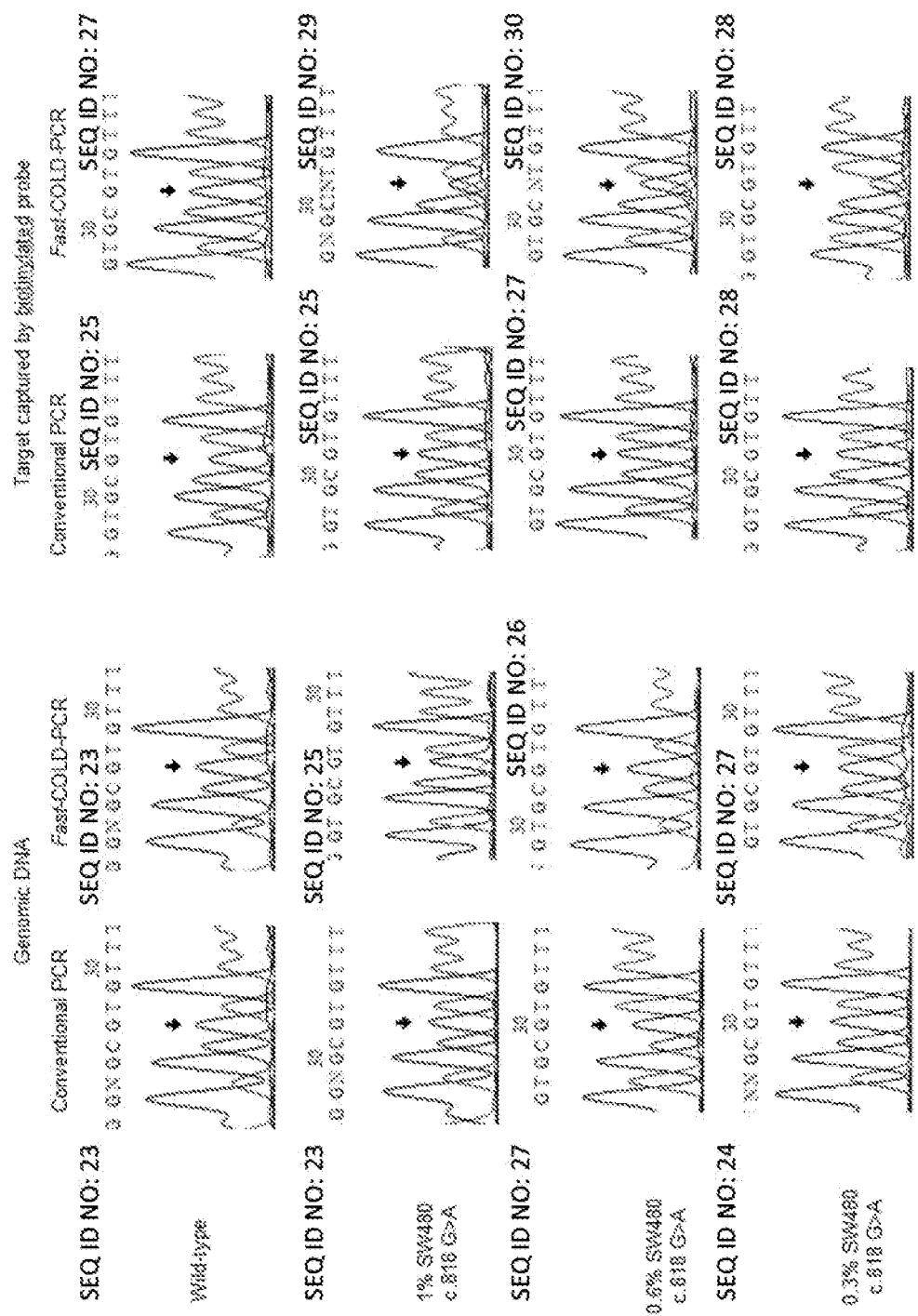
FIG. 6 demonstrates that the lowest mutation abundance detectable was ~0.3% abundance using bead-isolated DNA, while the detection limit for reactions using genomic DNA was 1% mutant abundance.

The data indicate that the mutant allele was amplified preferentially when COLD-PCR was performed both directly from genomic DNA or using bead-isolated DNA, albeit to a different extent (FIG. 5). Using genomic DNA as template, the 1% c.818 G>A mutation in TP53 exon 8 was enriched to ~17%, corresponding to ~17-fold mutant enrichment. However, when probe-isolated ssDNA was used as template, the 1% c.818 G>A mutation was enriched to 40%: i.e. the enrichment by COLD-PCR was more than doubled. Furthermore, the lowest mutation abundance detectable was ~0.3% abundance using bead-isolated DNA, while the detection limit for reactions using genomic DNA was 1% mutant abundance (FIG. 6).

Principle of Multiplexing Fast-COLD-PCR Using Bead-Isolated DNA

An alternative way to apply COLD-PCR involves fast-COLD-PCR wherein amplicons resulting from G:C>A:T or G:C>T:A mutations tend to have lower melting temperature. These amplicons can thus be preferentially denatured over wild type amplicons at $T_c$, with no need for the formation of heteroduplexes during PCR cycling.

Figure 7:
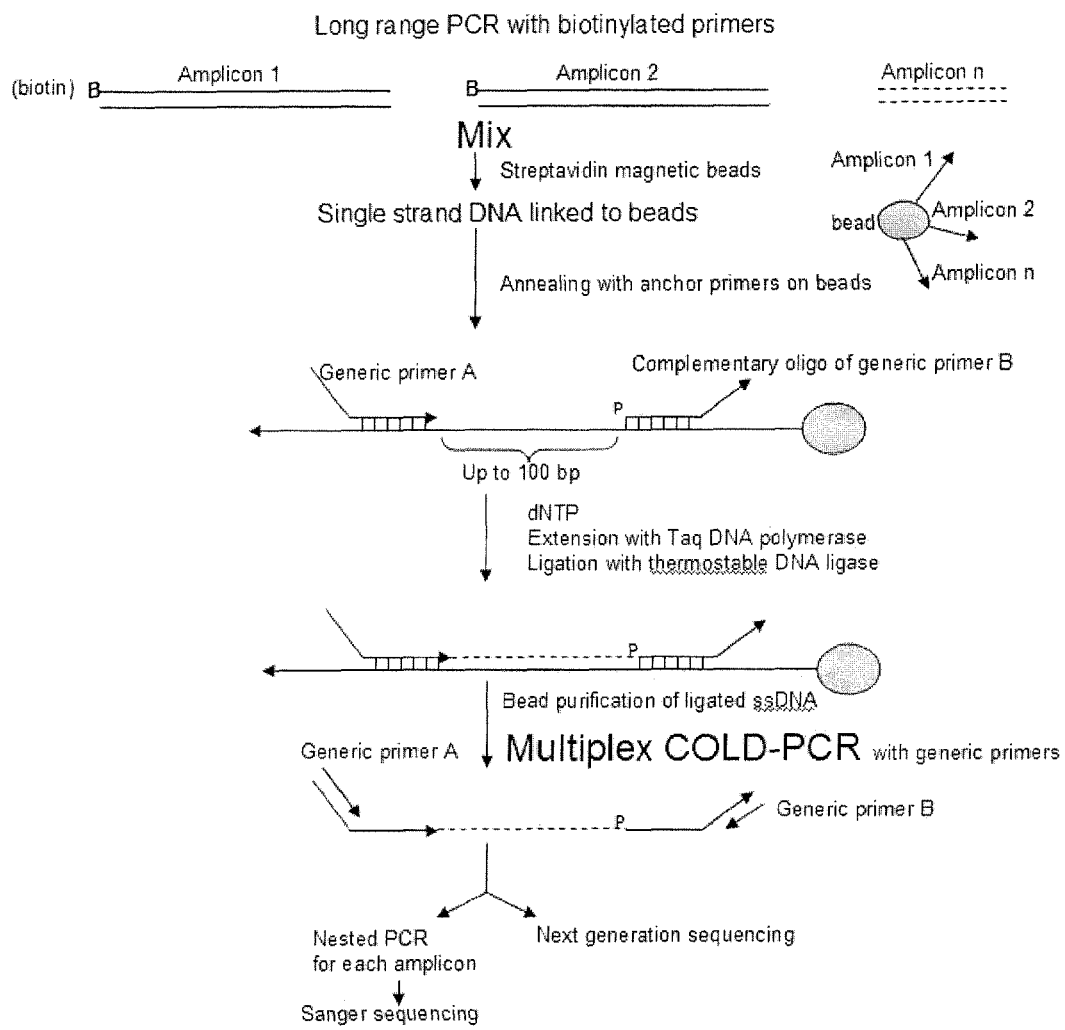
FIG. 7 shows one approach to apply multiplex COLD-PCR. Multiple targeted genes were amplified by long-range PCR with high-fidelity polymerase with one of the primer labeled with biotin at its 5' end in each amplicon. The 5' labeled single strand DNA were immobilized onto streptavidin magnetic beads and annealed to anchor primers consisting of generic regions and a targeted gene sequence. Ligation mediation amplification was performed followed by conventional PCR or COLD-PCR using generic primer A and B, to generate copies of target regions that have the same Tc and hence can be amplified in a single COLD-PCR reaction.

To date, COLD-PCR has improved the mutation-detection sensitivity of many techniques including Sanger sequencing, pyrosequencing, TaqMan real-time PCR, RFLP, dHPLC and high-resolution melting. However, each COLD-PCR reaction is performed in a simplex fashion, and multiplexing COLD-PCR is limited, because each individual amplicon requires a different $T_c$. To demonstrate the feasibility of multiplex COLD-PCR, and because bead capture improves the performance of COLD-PCR, we designed a multiplex fast-COLD-PCR strategy following DNA target isolation on magnetic beads, which allows for mutation identification by downstream Sanger sequencing or, potentially, next-generation sequencing (FIG. 7). Long-range PCR with 5'-biotinylated primers was carried out using high-fidelity DNA polymerase from genomic DNA to selectively amplify target sequences. The purpose of performing long-range PCR was to simplify the genome and to cover multiple exons in one amplicon (e.g. TP53 exons 5-9 within a single 2.5 kb amplicon in this study). However, potentially, the same protocol can also be adjusted to start directly from genomic DNA in future applications.

As shown in FIG. 7, the amplified products were mixed, followed by isolation of 5' biotinylated ssDNA using streptavidin-coated magnetic beads. A pair of anchor primers complimentary to the same strand was designed to include up to 100 bp from the gene region of interest. Both anchor primers consist of a gene specific region tailed with a universal sequence, which can be generic primers used in next-generation sequencing. In this study primers A and B used by 454 sequencing system (Roche Inc) were employed. The left anchor primer includes the 454 primer A sequence at the 5' end, and the right anchor primer is 5'-phosphorylated and includes the complementary sequence of the 454 primer B at the 3' end. After annealing to isolated ssDNA that has been immobilized on the beads, the left anchor was extended by AmpliTaq DNA polymerase, Stoffel Fragment, and dNTPs, followed by ligation to the right anchor by a thermostable DNA ligase, Ampli DNA ligase. It is important to use a DNA polymerase without 5'→3' exonuclease activity like AmpliTaq for this assay, because the 5'→3' exonuclease activity would digest the down stream anchor. Multiple target regions can be gap-filled and ligated using this strategy. The ligated ssDNA, containing a left-anchor at the 5' end, a right-anchor at the 3' end and a target region in the middle, was then released from the magnetic beads by brief heat denaturation. Fast-COLD-PCR was then applied on the purified DNA with generic primers A and B. Following this, nested conventional PCR was performed to amplify each target region individually, followed by Sanger sequencing. Alternatively, if a highly-multiplexed reaction is performed, next-generation sequencing can be used to screen for mutations in a highly-parallel manner.

Simplex and Duplex COLD-PCR from Ligated ssDNA

Figure 8:
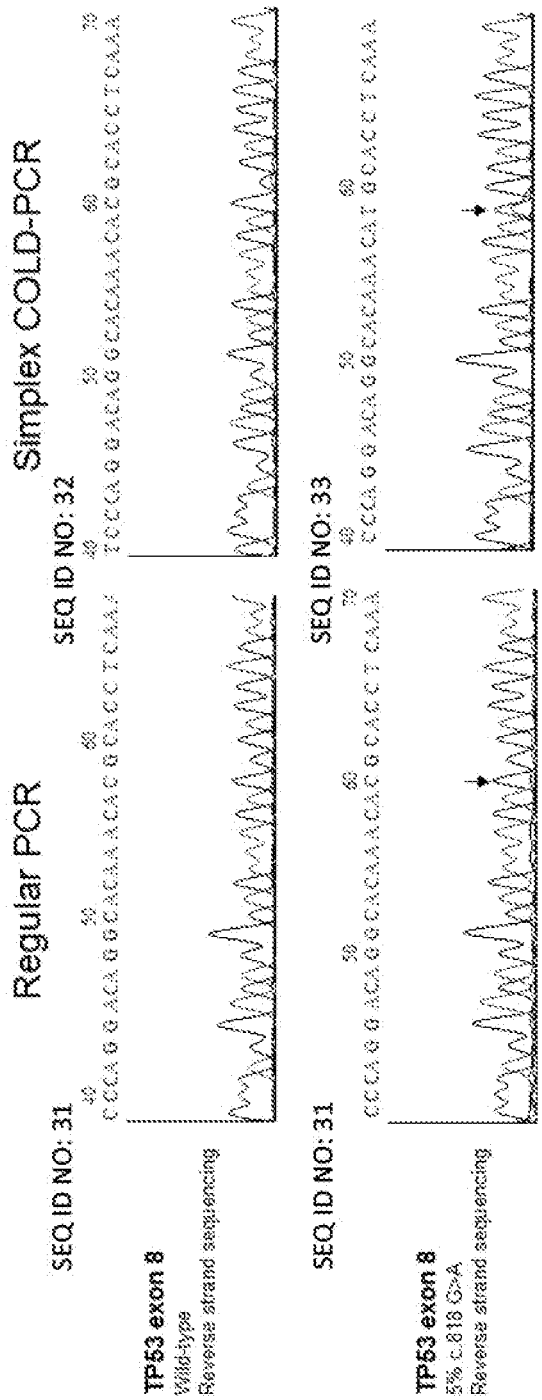
FIG. 8 demonstrates simplex conventional and COLD-PCR detection of a TP53 exon 8 mutation. A 5% TP53 exon 8 c.818 G>A mutation diluted into wild-type DNA was processed with the ligation-based approach followed by conventional PCR or COLD-PCR with $T_c$ at 86° C. Reverse strand was sequenced. A wild-type DNA was processed as a control, in parallel. The arrows indicate the position of the mutation.

As a proof of principle, we first followed the scheme of FIG. 7 to perform a simplex COLD-PCR from a single target region, TP53 exon 8 containing a c.818 G>A mutation diluted in wild-type DNA at a mutant-to-wild type ratio of 5%. ssDNA composed of anchors and TP53 exon 8 was isolated and processed with conventional PCR or COLD-PCR at a $T_c$ of 86° C. using generic primers as described above. Sanger sequencing (FIG. 8 showed that the 5% mutation abundance was not visible after conventional PCR, but could be clearly detected as a 70% mutation abundance following enrichment with COLD-PCR. Sequencing of similarly-treated wild-type DNA after COLD-PCR did not show any indication of enrichment of PCR errors when compared to conventional PCR.

Next, we followed the scheme of FIG. 7 to design a duplex COLD-PCR to enrich mutations from TP53 exon 6 and exon 9 simultaneously. Ideally, all of the amplicons in a multiplex COLD-PCR should have a similar $T_c$ so that enrichment occurs on all targets simultaneously. The targeted regions within exons 6 and 9 were thus designed to have a $T_c$ very similar to each other, 85° C. and 84.5° C. respectively. COLD-PCR was performed using two different approaches, i.e. either using a single $T_c$ of 84.7° C. (average of 84.5° C. and 85° C.), or using a two-temperature format including 12 cycles of COLD-PCR at $T_c$ of 84.5° C. followed by 12 cycles of COLD-PCR at $T_c$ of 85° C. This graded increase of the $T_c$ during fast-COLD-PCR has been previously shown to be tolerant to small temperature differences between reactions that are caused by the inherent well-to-well variation of thermocyclers. This strategy was adapted here to amplify two amplicons that have somewhat different $T_c$.

Figure 9:
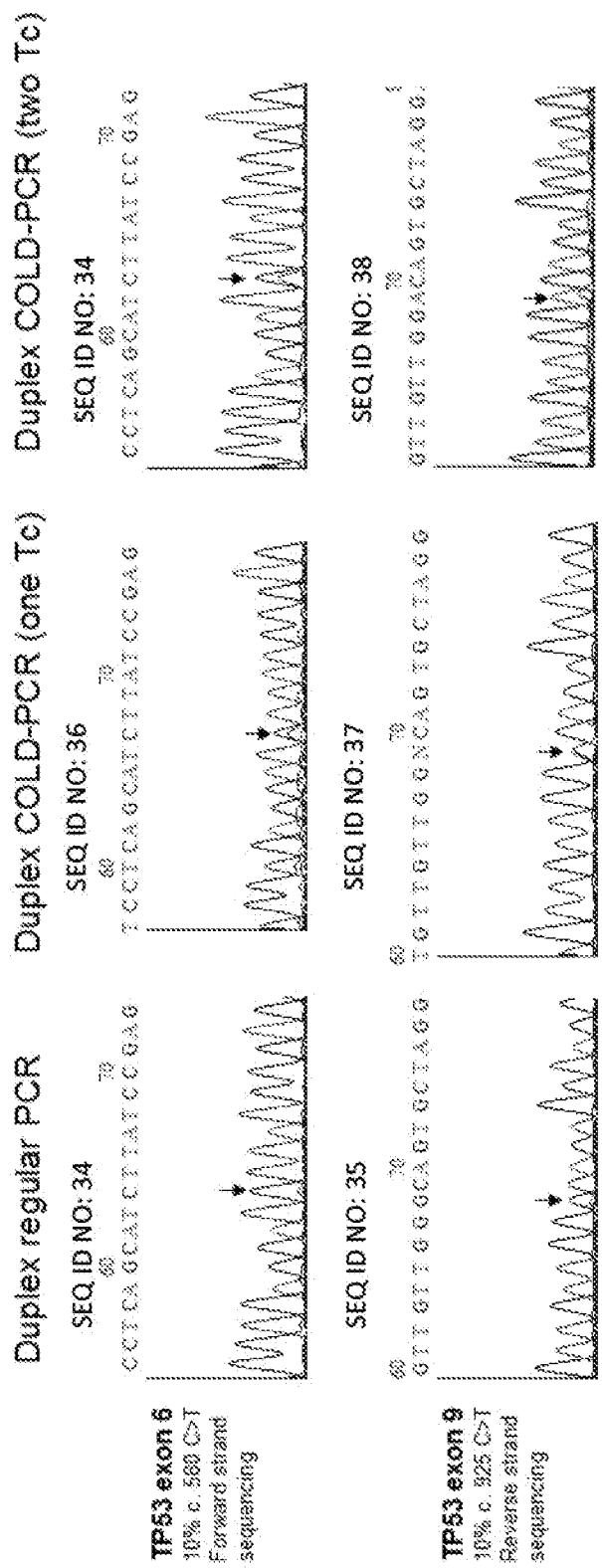
FIG. 9 shows duplex conventional and COLD-PCR detection of a TP53 exon 6 and exon 9 mutation. A mixture of 10% TP53 exon 6 c.580 C>T mutation and 10% TP53 exon 9 c.925 C>T mutation diluted into wild-type DNA was processed with the ligation based approach followed by conventional PCR or COLD-PCR with single $T_c$ at 84.7° C. or two-temperature $T_c$, a first $T_c$ at 84.5° C. followed by $T_c$ at 85° C. Nested PCR were performed to isolate the target exons to allow Sanger sequencing. The arrows indicate the position of the mutation.

The 10% c.580 C>T mutation in TP53 exon 6 was not detectable by conventional PCR-sequencing, but was enriched and became clearly visible following one—$T_c$ and two—$T_c$ COLD-PCR as a 30-40% mutation (FIG. 9). Similarly, the 10% c.925 C>T mutation in TP53 exon 9 was not detectable after conventional PCR, but was clearly detected following one—$T_c$ and two—$T_c$ COLD-PCR as a 50% and 80% mutation, respectively (FIG. 9).

Temperature-Independent TI-COLD-PCR

Figure 10:
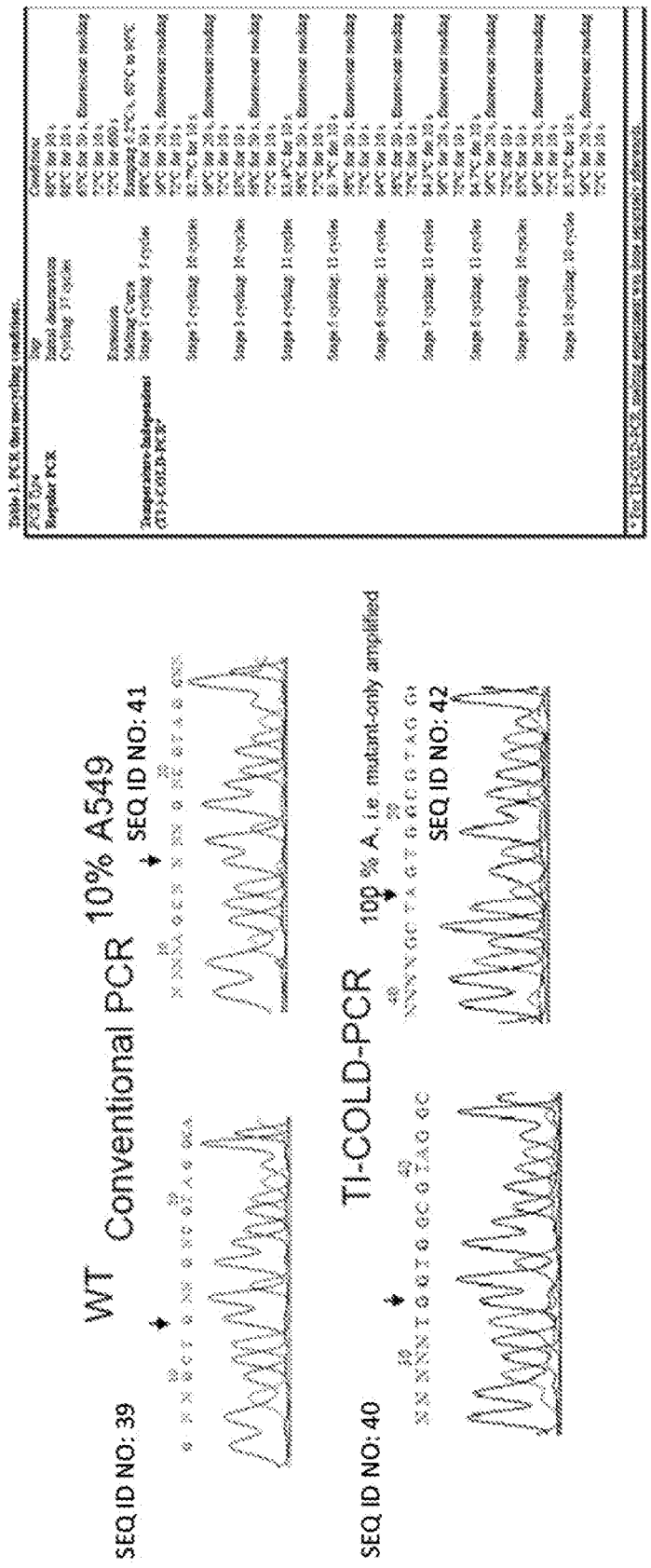
FIG. 10 shows temperature-independent COLD-PCR for a KRAS codon 12 sequence in solution. The mutation containing sequences are preferentially amplified during TI-COLD-PCR and are clearly sequenced. In contrast, sequencing from conventional PCR only shows amplification when a denaturation temperature of 84.7° C. is used.

We have obtained proof of principle for temperature-independent TI-COLD-PCR in solution, when run in a fast COLD-PCR mode (i.e. without the intermediate heteroduplex-ing step), for a single target sequence. The thermocycler was programmed as disclosed in FIG. 10, for a wild-type Kras sequence or, alternatively, for a 10% mixture of mutant-to-wild type sequence. The resulting chromatographs in FIG. 10 demonstrate that, by ramping the denaturation temperature from lower to higher values and without knowledge of the exact critical denaturation temperature (Tc) of this Kras sequence it was still possible to perform mutation enrichment successfully. The chromatogram demonstrates that the 10% G>A mutation became 100% mutation following TI-COLD-PCR (fast mode). Of note, the fast COLD-PCR program of FIG. 16 will only enrich temperature-reducing mutations (G:C>A:T, or G:C>T:A), which comprise about 70% of the mutations encountered in clinical samples.

Target isolation is critical for both basic and translational research, as well as in molecular diagnostics of human diseases. It allows the characterization of specific cell type, protein, nucleic acid and investigation of their functions; in clinics, target isolation provides direct evidence for disease diagnosis. Among all separation techniques used today, magnetic beads coated with different biomolecules have received much attention due to its diversity, high performance, low cost, and ease of use. They have successfully been used in many preclinical and clinical applications, including isolation of rare circulating tumor cells, pathogen detection, and T cell activation/expansion for treating HIV infection and other human diseases. In addition, magnetic beads are often integrated into a broad range of in vitro diagnostic tools such as human exome capture for next generation sequencing and the Illumina GoldenGate™ genotyping assay. In this study, we integrated magnetic beads in COLD-PCR applications, and showed that following target isolation using beads, sensitivity of mutation detection by COLD-PCR is significantly enhanced, and multiplexing COLD-PCR is feasible.

Previous studies have shown that the sensitivity of mutation detection was significantly improved by performing two rounds of COLD-PCR, which allowed the enrichment and sequencing of low level mutations in lung adenocarcinoma samples that would otherwise have been missed by conventional methodologies (Li J, Milbury C A, Li C, Makrigiorgos G M. Two-round coamplification at lower denaturation temperature-PCR(COLD-PCR)-based sanger sequencing identifies a novel spectrum of low-level mutations in lung adenocarcinoma. Hum Mutat 2009; 30:1583-90). Although polymerase-introduced errors were not evident following two rounds of COLD-PCR that employed a high fidelity (Phusion) polymerase, there remains potential concern due to the number of PCR cycles conducted. Target isolation using magnetic beads has been shown to significantly enhance mutation detection. Indeed, the present combination of magnetic bead-based isolation with fast-COLD-PCR showed that the sensitivity of mutation detection by COLD-PCR was greatly enhanced, allowing as low as 0.3% mutant abundance to be detected with a single COLD-PCR reaction. This level of sensitivity is similar to that obtained with two rounds fast-COLD-PCR.

The improvement in mutation enrichment obtained by COLD-PCR is likely due to the number of COLD-PCR cycles performed prior to the amplification reaction reaching saturation. All COLD-PCR reactions include an initial number of cycles of conventional PCR for an initial build-up of the PCR product, immediately followed by direct switching to COLD-PCR cycling to selectively amplify mutation-containing amplicons. If the conventional PCR cycling is omitted, or if COLD-PCR cycling occurs too early, then excessive primer-dimer formation can occur because the $T_p$, is lower for these molecules than for the intended target amplicons. On the other hand, performing too many cycles in the conventional PCR mode, prior to switching to COLD-PCR, can reduce the overall enrichment of mutation-containing amplicons. The present data indicate that, compared to reactions performed on genomic DNA, COLD-PCR using bead-isolated DNA could be initiated ~8 cycles earlier without introducing significant primer-dimer problems, thus allowing more COLD-PCR cycles that enrich amplicons with mutations.

Regarding multiplexed-COLD-PCR, in principle it would have been possible to adapt conventional multiplex PCR to COLD-PCR by designing amplicons that possess the same $T_c$. However, this strategy would suffer from the formation of primer-dimer and mispriming. The multiplex COLD-PCR assay designed in this work (FIG. 7) employs generic primers for all of the amplicons to eliminate the issue of primer dimers, while still retaining similar $T_c$ for the amplicons. This approach has been previously used for high-throughput expression profiling and methylation detection, using either padlock probes or pairs of separate oligonucleotides. The protocol adopted includes a ligation step to generate amplifiable probes. Although the ligation step is not absolutely necessary in the present protocol, it provides added specificity and flexibility to select amplicons containing desired single nucleotide polymorphisms, as demonstrated for the Illumina GoldenGate™ genotyping assay (Fan J B, Chee M S, Gunderson K L. Highly parallel genomic assays. Nat Rev Genet. 2006; 7:632-44). Thereby one can potentially perform COLD-PCR on a given allele following the protocol of FIG. 7, by performing SNP-specific ligation. It is envisioned that the current protocol can lead to large-scale COLD-PCR amplification and mutation enrichment within numerous iso-$T_c$ amplicons following genomic DNA capture, an approach similar to applications performing exon capture and target isolation for resequencing using next generation sequencing technologies.

Our data showed that mutation enrichment via COLD-PCR is enhanced by target isolation using magnetic beads. Furthermore, we developed a multiplex COLD-PCR assay using DNA that was isolated and immobilized on magnetic beads. These approaches provide a platform that can be developed further to screen for a panel of mutations that are critical for decision making in personalized cancer treatment, without the risk of missing low-level mutations in clinical samples.

RE.SE.CT

Figure 16:
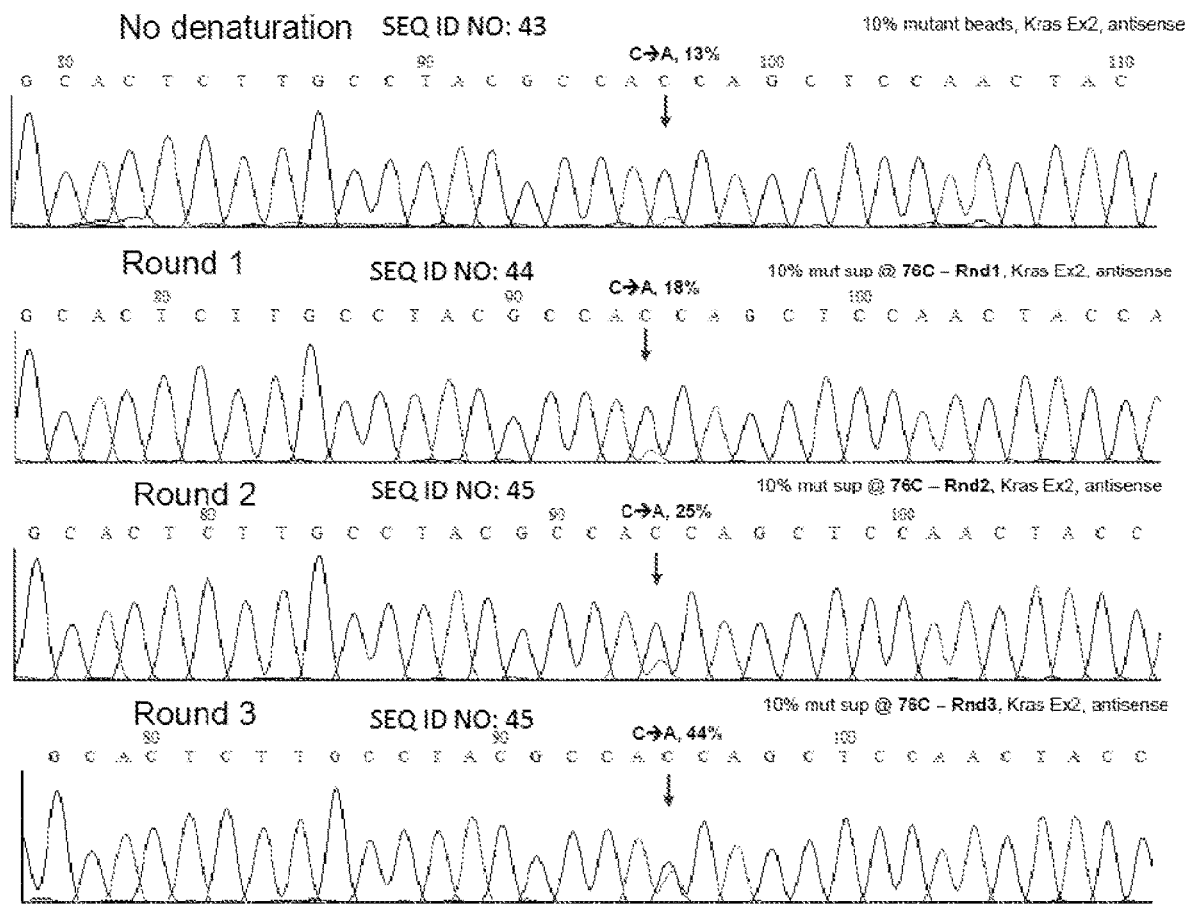
FIG. 16 shows RE.SE.CT enrichment for a KRAS point mutation C>A. At each round, the mutated sequence was enriched.
Figure 18:
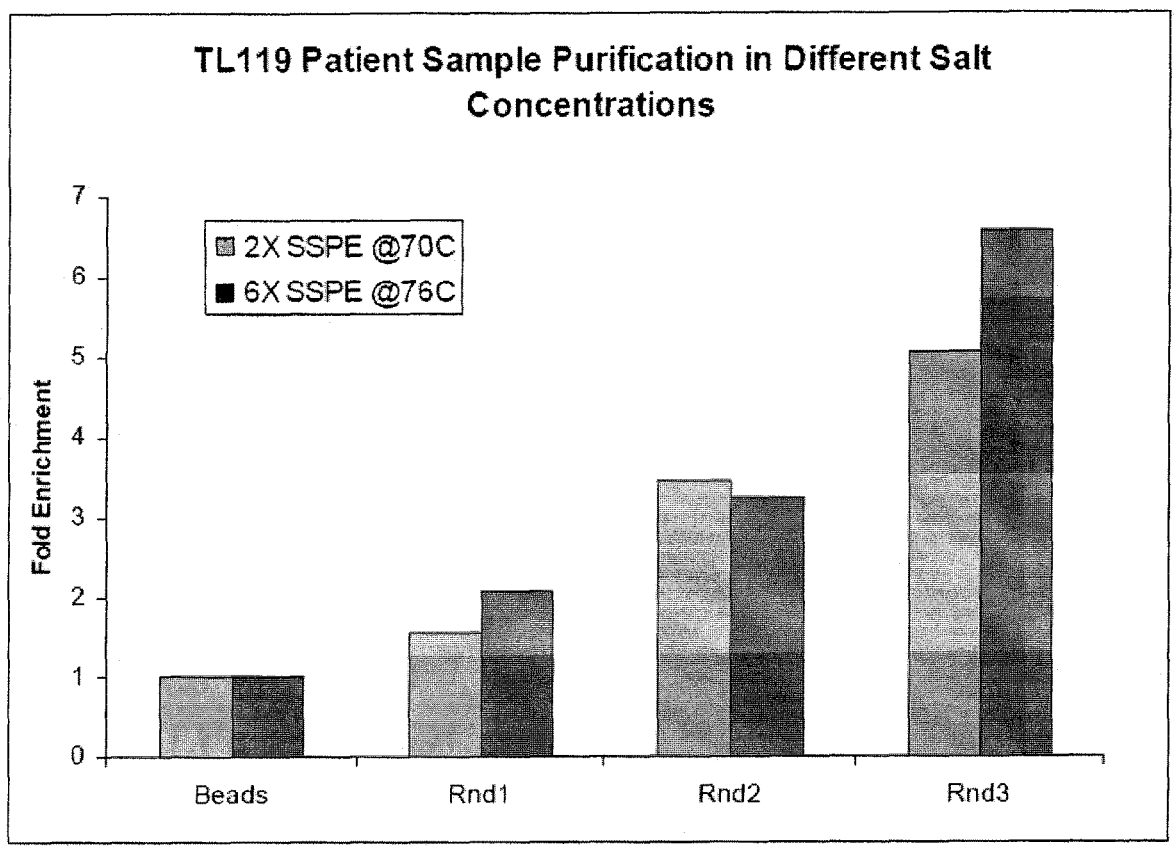
FIG. 18 shows bead purification of KRAS double mutation (CC>AA) from TL119 patients.
Figure 19:
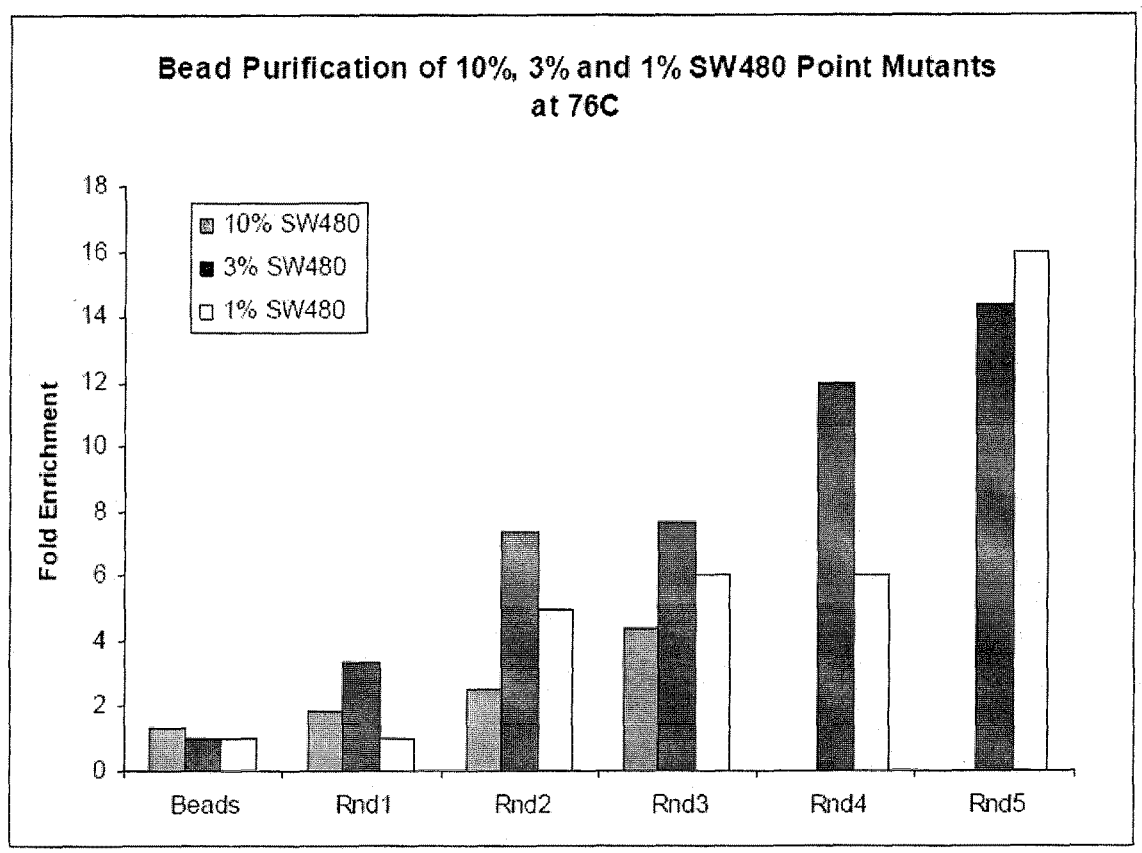
FIG. 19 shows the enrichment of KRAS single point mutation (C>A) from SW480 mutant DNA mixtures.
Figure 20:
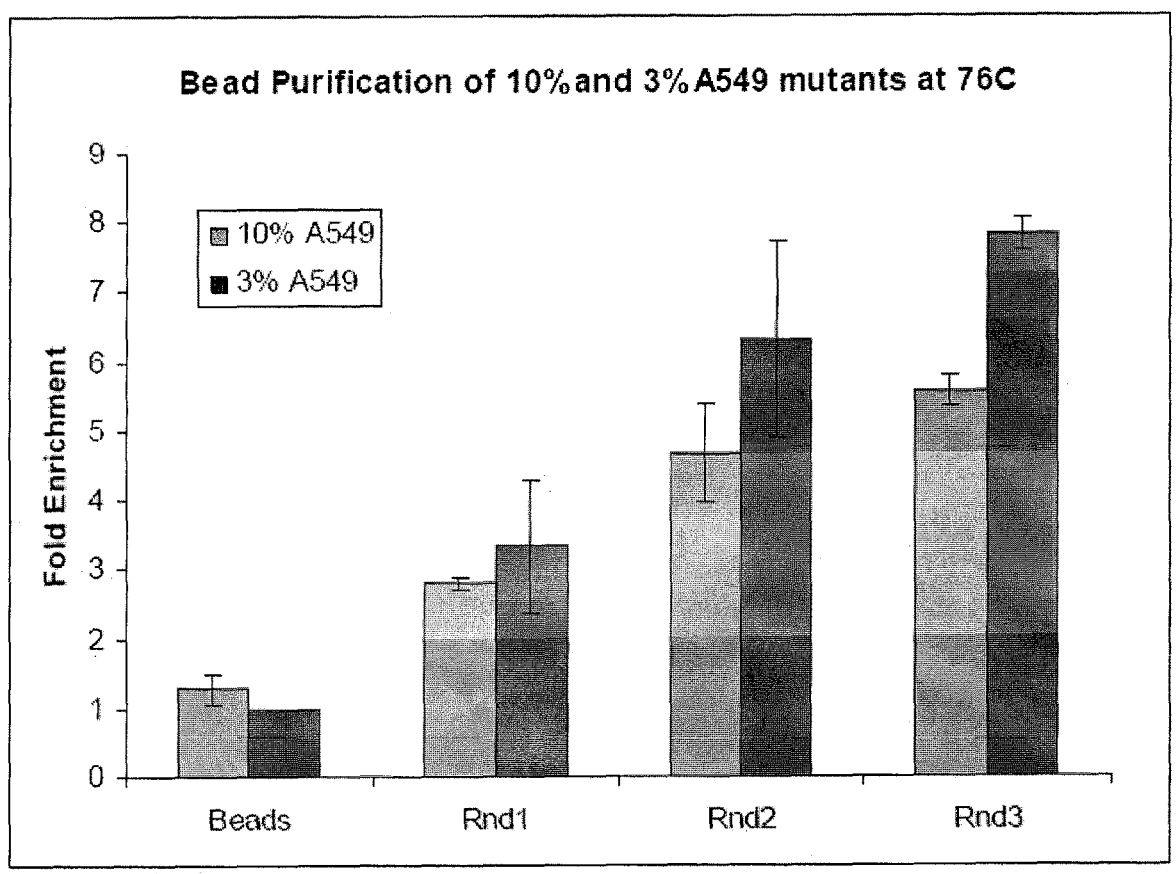
FIG. 20 shows the enrichment of KRAS Single point mutant (C>T) from A549 mutant DNA mixtures.
Figure 21:
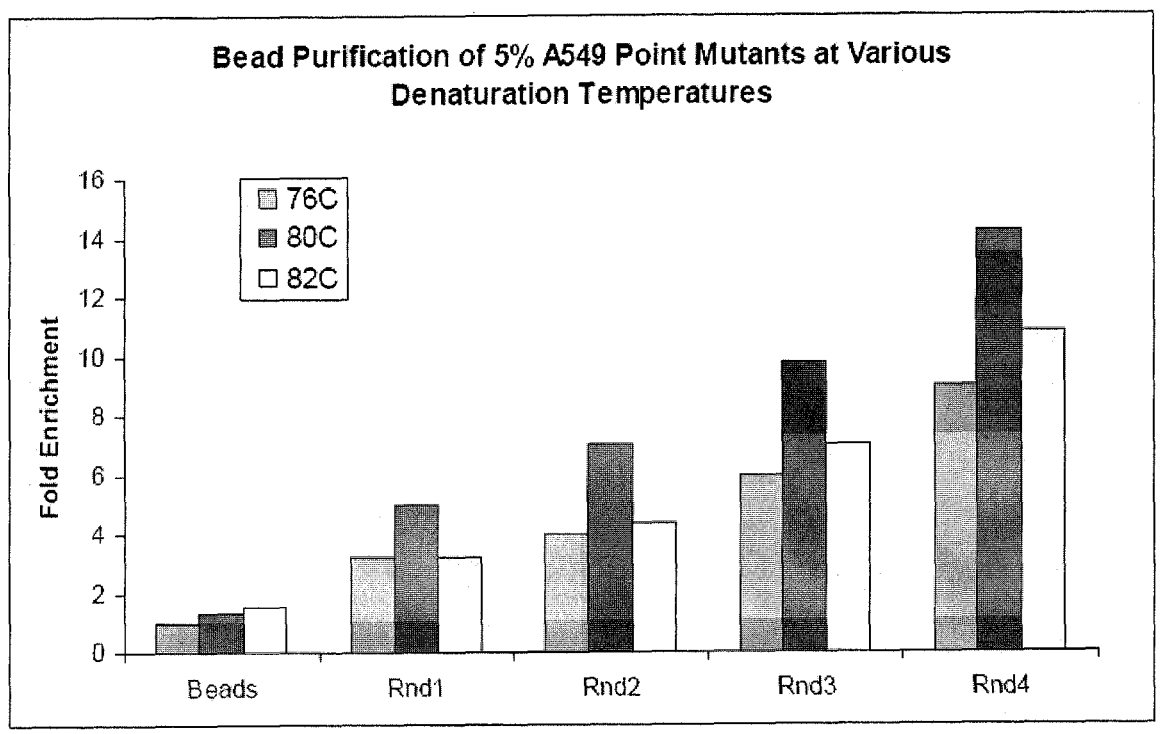
FIG. 21 shows the enrichment of KRAS Single point mutant (C>T) at various denaturation temperatures

Validation has been performed for DNA containing mutations in the Kras exon 2 sequence. FIG. 16 demonstrates 3 cycles of the process, applied to DNA originally containing a 10-13% mutant-to-wild type sequence for a C>A Kras mutation. Following each cycle of the process, the resulting sample was tested via PCR-sequencing. It can be seen that following each cycle the mutation (peaks in the chromatograph indicating A) increases relative to wild type. A similar progressive enrichment of mutated sequences is shown in FIG. 17 for a different Kras mutation (CC>AA). FIGS. 18-21 demonstrate the enrichment obtained progressively by repeated cycles of RE.SE.CT for several examples of Kras mutations. In each example, the enrichment was obtained by performing PCR-sequencing after each cycle of RE.SE.CT.

I claim:

1. A method for enriching for a plurality of mutant target sequences in a single reaction mixture comprising:
   (a) providing a nucleic acid sample containing multiple target sequences suspected of being made up of both mutant target sequences and wild-type target sequences, wherein the mutant target sequences comprise at least a first mutant target sequence and a second mutant target sequence, and wherein the wild-type target sequences comprise at least a first wild-type target sequence and a second wild-type target sequence;
   providing reference sequences that are complementary to the wild-type target sequences and can form duplexes with wild-type target sequences and mutant target sequences, wherein the reference sequences comprise at least a first reference sequence complementary to the first wild-type target sequence and a second reference sequence complementary to the second wild-type target sequence; and
   providing pairs of nucleic acid primers, wherein each pair of primers generates under nucleic acid amplification conditions an amplicon that is a copy of one of the target sequences and its corresponding reference sequence, and wherein the amplicon generated by one pair of primers is different from the amplicon generated by each other pair of primers,
   (b) forming a reaction mixture, wherein the reaction mixture is a single reaction mixture containing the nucleic acid sample, the reference sequences and the pairs of nucleic acid primers,
   (c) subjecting the target sequences and the reference sequences in the single reaction mixture to a denaturing temperature that is above the melting temperature of the target sequences and the reference sequences,
   (d) reducing the temperature of the single reaction mixture to permit the formation of target strand/reference strand duplexes, wherein the temperature is above the primer annealing/extension temperature,
   (e) subjecting any duplexes in the single reaction mixture to a first critical denaturation temperature, the first critical denaturation temperature being below the lowest melting temperature of the duplex formed by the at least first wild-type target sequence and the at least first reference sequence, to permit selective denaturation of the duplexes containing the at least first mutant target sequence, without denaturation of the duplexes formed by the at least first wild-type target sequence with the at least first reference sequence,
   (f) reducing the temperature of the single reaction mixture in the presence of pairs of nucleic acid primers and permitting the primers to anneal to the target sequences,
   (g) extending the primers to enrich the target sequences,
   (h) repeating steps (e) to (g) at least once at a second critical denaturation temperature, the second critical denaturation temperature being above the first critical denaturation temperature and below the lowest melting temperature of the duplex formed by the at least second wild-type target sequence and the at least second reference sequence to permit selective denaturation of duplexes containing the at least second mutant target sequence, without denaturation of the duplexes formed by the at least second wild-type target sequence with the at least second reference sequence, to ensure selective amplification of the mutant target sequences over the wild-type target sequences.

2. A method for enriching for a plurality of mutant target sequences in a single reaction mixture comprising:
   (a) providing a nucleic acid sample containing multiple target sequences suspected of being made up of both mutant target sequences and wild-type target sequences, wherein the mutant target sequences comprise at least a first mutant target sequence and a second mutant target sequence, and wherein the wild-type target sequences comprise at least a first wild-type target sequence and a second wild-type target sequence;
   providing reference sequences that are complementary to the wild-type target sequences and can form duplexes with wild-type target sequences and mutant target sequences, wherein the reference sequences comprise at least a first reference sequence complementary to the first wild-type target sequence and a second reference sequence complementary to the second wild-type target sequence; and
   providing pairs of nucleic acid primers, wherein each pair of primers generates under nucleic acid amplification conditions an amplicon that is a copy of one of the target sequences and its corresponding reference sequence, and wherein the amplicon generated by one pair of primers is different from the amplicon generated by each other pair of primers,
   (b) forming a reaction mixture, wherein the reaction mixture is a single reaction mixture containing the nucleic acid sample, the reference sequences and the pairs of nucleic acid primers,
   (c) subjecting the target sequences and the reference sequences in the single reaction mixture to a denaturing temperature that is above the melting temperature of the target sequences and the reference sequences,
   (d) reducing the temperature of the single reaction mixture in the presence of pairs of nucleic acid primers and permitting the primers to anneal to the target sequences,
   (e) extending the primers to enrich the target sequences,
   (f) subjecting the target sequences and the reference sequences in the single reaction mixture to a denaturing temperature that is above the melting temperature of the target sequences and the reference sequences,
   (g) reducing the temperature of the single reaction mixture to permit the formation of target strand/reference strand duplexes, wherein the temperature is above the primer annealing/extension temperature,
   (h) subjecting any duplexes in the single reaction mixture to a first critical denaturation temperature, the first critical denaturation temperature being below the lowest melting temperature of the duplex formed by the at least first wild-type target sequence and the at least first reference sequence, to permit selective denaturation of the duplexes containing the at least first mutant target sequence, without denaturation of the duplexes formed by the at least first wild-type target sequence with the at least first reference sequence,
(i) reducing the temperature of the single reaction mixture in the presence of pairs of nucleic acid primers and permitting the primers to anneal to the target sequences,
(j) extending the primers to enrich the target sequences,
(k) repeating steps (h) (j) at least once at a second critical denaturation temperature, the second critical denaturation temperature being above the first critical denaturation temperature and below the lowest melting temperature of the duplex formed by the at least second wild-type target sequence and the at least second reference sequence to permit selective denaturation of duplexes containing the at least second mutant target sequence, without denaturation of the duplexes formed by the at least second wild-type target sequence with the at least second reference sequence, to ensure selective amplification of the mutant target sequences over the wild-type target sequences.

3. The method of claim 1, wherein steps (e) to (g) are repeated at least 2 times at successively increasing critical denaturation temperatures.

4. The method of claim 1, wherein steps (e) to (g) are repeated at least 3 times at successively increasing critical denaturation temperatures.

5. The method of claim 1, wherein steps (e) to (g) are repeated at least 4 times at successively increasing critical denaturation temperatures.

6. The method of claim 1, wherein at each critical denaturation temperature, steps (e) to (g) are repeated for two or more cycles.

7. The method of claim 2, wherein one or more deoxynucleotide triphosphates containing modified DNA bases are included in the single reaction mixture.

8. A method for preparing a single stranded mutant target sequence from a mixture of target sequences suspected of containing both the mutant target sequence and a wild-type target sequence, the method comprising:
(i) providing a sample suspected of containing mutant target sequences and wild-type target sequences,
(ii) providing a solution of reference sequences, wherein the reference sequences are complementary to the wild-type target sequences and can form duplexes with wild-type target sequences and mutant target sequences,
(iii) subjecting the target sequences to a denaturing temperature that is above the melting temperature of the target sequences, thereby forming a mixture containing the single stranded mutant target sequence and single stranded wild-type target sequences,
(iv) combining the mixture with the solution of reference sequences
(v) reducing the temperature to permit formation of target strand/reference strand duplexes, wherein the duplexes include mutant target strand/reference strand duplexes and wild-type target strand/reference strand duplexes,
(vi) subjecting the target strand/reference strand duplexes to a critical denaturation temperature that is below the melting temperature of the wild-type target strand/reference strand duplexes, to permit selective denaturation of mutant target strand/reference strand duplexes, whereby the single stranded mutant target sequences are enriched relative to the single stranded wild-type target sequences,
further comprising
(vii) after (vi), removing wild-type target strand/reference strand duplexes,
(viii) repeating steps (v)-(vii) at least 1 time to further enrich for the single stranded mutant target sequences, wherein the method does not comprise performing PCR between step (i) and step (viii).

9. The method of claim 8, wherein steps (v)-(vii) are repeated at least 2 times to further enrich for the single stranded mutant target sequences.

10. A method for preparing a single stranded mutant target sequence from a mixture of target sequences suspected of containing both the mutant target sequence and a wild-type target sequence, the method comprising:
(i) providing a sample suspected of containing mutant target sequences and wild-type target sequences,
(ii) providing a solution of reference sequences, wherein the reference sequences are complementary to the wild-type target sequences and can form duplexes with wild-type target sequences and mutant target sequences,
(iii) subjecting the target sequences to a denaturing temperature that is above the melting temperature of the target sequences, thereby forming a mixture containing the single stranded mutant target sequence and single stranded wild-type target sequences,
(iv) combining the mixture of (iii) with the solution of reference sequences,
(v) reducing the temperature to permit formation of target strand/reference strand duplexes, wherein the duplexes include mutant target strand/reference strand duplexes and wild-type target strand/reference strand duplexes,
(vi) subjecting the target strand/reference strand duplexes to a critical denaturation temperature that is below the melting temperature of the wild-type target strand/reference strand duplexes, to permit selective denaturation of mutant target strand/reference strand duplexes, whereby the single stranded mutant target sequences are enriched relative to the single stranded wild-type target sequences,
further comprising
(vii) after (vi), removing reference sequences,
(viii) adding additional excess of reference sequences,
(ix) repeating steps (v)-(vi) at least 1 time to further enrich for the single stranded mutant target sequences, wherein the method does not comprise performing PCR between step (i) and step (ix).

11. The method of claim 10, wherein steps (v)-(vi) are repeated at least two times to further enrich for the single stranded mutant target sequences.

12. The method of claim 10, wherein the reference sequences are attached to particles.

13. The method of claim 10, wherein the reference sequences are attached to magnetic particles.

* * * * *

SEQUENCE LISTING

<160> NUMBER OF SEQ ID NOS: 46

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotinylated

<400> SEQUENCE: 1
gaatctgagg cataactgca cc                                               22

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
cctgacctgc cgtctagaaa a                                                21

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3
ctccgacgcc tgcttcac                                                    18

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tgcctcttgc ttctcttttc                                                  20

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
ctttcttgcg gagattctct tc                                               22

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
ttgcttctct tttcctat                                                    18

```
<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
acttcaatgc ctggccgtat                                                  20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotinylated

<400> SEQUENCE: 8
gccccaattg caggtaaaac                                                  20

<210> SEQ ID NO 9
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 9
gcctccctcg cgccatcaga gggtccccag gcctctga                              38

<210> SEQ ID NO 10
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 10
ttggatgaca gaaacacttt tcgctgagcg ggctggcaag gc                         42

<210> SEQ ID NO 11
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 11
gcctccctcg cgccatcagt gcctcttgct tctcttttcc t                          41

<210> SEQ ID NO 12
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 12
ccgcaagaaa ggggagcctc tgagcgggct ggcaaggc                              38

<210> SEQ ID NO 13
<211> LENGTH: 41
<212> TYPE: DNA
```

```
<213> ORGANISM: Artificial sequence
<220> FEATURE:
<223> OTHER INFORMATION: Synthetic oligonucleotide

<400> SEQUENCE: 13
gcctccctcg cgccatcagt cacctttcct tgcctctttc c                    41

<210> SEQ ID NO 14
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 14
tggatggaga atatttcacc cttctgagcg ggctggcaag gc                   42

<210> SEQ ID NO 15
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 15
gtaaaacgac ggccagtagg gtccccaggc ctctga                          36

<210> SEQ ID NO 16
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 16
tcccgcgaaa ttaatacgac cgaaaagtgt ttctgtcatc caa                  43

<210> SEQ ID NO 17
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 17
gtaaaacgac ggccagttca cctttccttg cctctttcc                       39

<210> SEQ ID NO 18
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 18
tcccgcgaaa ttaatacgac aagggtgaaa tattctccat cca                  43

<210> SEQ ID NO 19
<211> LENGTH: 36
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t
```

<400> SEQUENCE: 19
gctttgaggn gcgtgtttgt gcctgtcctg ggagag                              36

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 20
gctttgaggt gcgtgtttgt gcctgtcctg ggagag                              36

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t

<400> SEQUENCE: 21
nntttgaggt gcgtgtttgt gcctgtcctg ggagaga                             37

<210> SEQ ID NO 22
<211> LENGTH: 37
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: n is a, c, g, or t

<400> SEQUENCE: 22
gctttgaggt gcntgtttgt gcctgtcctg ggagaga                             37

<210> SEQ ID NO 23
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t

<400> SEQUENCE: 23
ggngcgtgtt t                                                         11

<210> SEQ ID NO 24
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t

<400> SEQUENCE: 24

-continued nngcgtgttt                                                               10

<210> SEQ ID NO 25
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 25
ggtgcgtgtt t                                                             11

<210> SEQ ID NO 26
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t

<400> SEQUENCE: 26 ngtgcgtgtt                                                               10

<210> SEQ ID NO 27
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 27
gtgcgtgttt                                                               10

<210> SEQ ID NO 28
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 28
ggtgcgtgtt                                                               10

<210> SEQ ID NO 29
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 29 gngcntgttt                                                               10

<210> SEQ ID NO 30
<211> LENGTH: 10
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t

<400> SEQUENCE: 30 gtgcntgttt                                                                 10

<210> SEQ ID NO 31
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 31
cccaggacag gcacaaacac gcacctcaaa                                           30

<210> SEQ ID NO 32
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 32
tcccaggaca ggcacaaaca cgcacctcaa a                                         31

<210> SEQ ID NO 33
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 33
cccaggacag gcacaaacat gcacctcaaa                                           30

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 34
cctcagcatc ttatccgag                                                       19

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 35
gttgttgggc agtgctagg                                                       19

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 36
tcctcagcat cttatccgag                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t

<400> SEQUENCE: 37
tgttgttggn cagtgctagg                                               20

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 38
gttgttggac agtgctagg                                                19

<210> SEQ ID NO 39
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 39
gnngctgnng ncgtaggca                                                19

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n is a, c, g, or t

<400> SEQUENCE: 40
nnnnntggtg gcgtaggc                                                 18

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (8)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t

<400> SEQUENCE: 41
nnnnagcnnn ngncgtaggn n                                               21

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: n is a, c, g, or t

<400> SEQUENCE: 42
nnnngctagt ggcgtagg                                                   18

<210> SEQ ID NO 43
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 43
gcactcttgc ctacgccacc agctccaact ac                                   32

<210> SEQ ID NO 44
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 44
gcactcttgc ctacgccacc agctccaact acca                                 34

<210> SEQ ID NO 45
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 45
gcactcttgc ctacgccacc agctccaact acc                                  33

<210> SEQ ID NO 46
<211> LENGTH: 34
<212> TYPE: DNA
<213> ORGANISM: Artificial Sequence
<220> FEATURE:
```

```
<223> OTHER INFORMATION: Synthetic oligonucleotide

<400> SEQUENCE: 46
gcactcttgc ctacgccaaa agctccaact acca                                    34
```